United States Patent [19]

Jasys et al.

[11] Patent Number: 4,457,924
[45] Date of Patent: Jul. 3, 1984

[54] 1,1-ALKANEDIOL DICARBOXYLATE LINKED ANTIBACTERIAL AGENTS

[75] Inventors: Vytautas J. Jasys, New London; Michael S. Kellogg, Waterford, both of Conn.

[73] Assignee: Pfizer, Inc., New York, N.Y.

[21] Appl. No.: 429,915

[22] Filed: Sep. 30, 1982

Related U.S. Application Data

[63] Continuation-in-part of Ser. No. 334,022, Dec. 22, 1981, abandoned.

[51] Int. Cl.³ .................. A61K 31/655; A61K 31/43; C07D 499/32; C07D 263/00
[52] U.S. Cl. .................. 424/226; 260/239.1; 260/245.2 R; 260/245.3; 424/250; 424/263; 424/270; 424/271; 424/272
[58] Field of Search ...................... 260/239.1, 245.2 R, 260/245.3; 424/226, 271, 270, 272, 263, 250

[56] References Cited

U.S. PATENT DOCUMENTS

| | | | |
|---|---|---|---|
| 2,985,648 | 5/1961 | Doyle et al. | 260/239.1 |
| 3,192,198 | 6/1965 | Naylor et al. | 260/239.1 |
| 3,520,876 | 7/1970 | Alburn et al. | 260/239.1 |
| 4,053,360 | 10/1977 | Bouzard | 195/29 |
| 4,234,579 | 11/1980 | Barth | 424/246 |
| 4,244,951 | 1/1981 | Bigham | 424/250 |

FOREIGN PATENT DOCUMENTS 2044255 10/1980 United Kingdom .

Primary Examiner—Natalie Trousof
Assistant Examiner—Vera C. Clarke

Attorney, Agent, or Firm—Charles J. Knuth; Albert E. Frost; Paul D. Thomas

[57] ABSTRACT

Useful antibacterial agents in which a penicillin and/or a beta-lactamase inhibitor are linked via 1,1-alkanediol dicarboxylates are of the formula

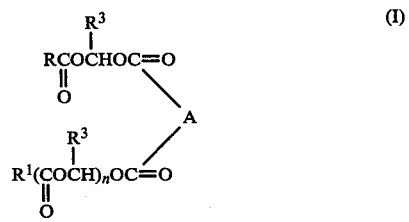

where A is the residue of certain dicarboxyic acids, $R^3$ is H or $(C_1-C_3)$, n is zero or 1 such that when n is zero R is P or B and $R^1$ is the residue of certain esters, H or a salt thereof; and when n is 1, one of R and $R^1$ is P and the other is B, and P is

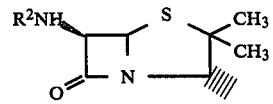

where $R^2$ is H or certain acyl groups, and B is the residue of a beta-lactamase inhibiting carboxylic acid; a method for their use, pharmaceutical compositions thereof and intermediates useful in their production.

52 Claims, No Drawings

1,1-ALKANEDIOL DICARBOXYLATE LINKED ANTIBACTERIAL AGENTS

CROSS-REFERENCE TO RELATED APPLICATION

This application is a continuation-in-part of copending application Ser. No. 334,022; filed Dec. 22, 1981 and now abandoned.

BACKGROUND OF THE INVENTION

1. Field of the Invention

This invention relates to new chemical compounds of value as antibacterial agents. More particularly it relates to monoesters and diesters of certain 1,1-alkanediol dicarboxylates in which a penicillin carboxyl group and/or the carboxyl group of certain beta-lactamase inhibitors are esterified.

2. Description of the Prior Art

Penicillanic acid 1,1-dioxide (sulbactam) is known from U.S. Pat. No. 4,234,579 to be an effective beta-lactamase inhibitor and antibacterial agent.

In U.S. Pat. No. 4,244,951 bis-esters of formula (IX) are disclosed in which sulbactam is coupled to known antibacterial penicillins via methanediol.

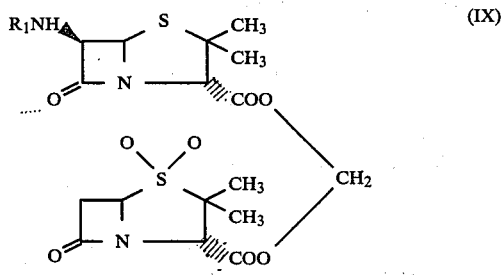

In the above formula $R_1$ represents certain acyl groups of known antibacterial penicillins. For example, $R_1$ can represent 2-amino-2-phenylacetyl or 2-amino-2-(p-hydroxyphenyl)acetyl.

In U.S. Pat. No. 4,342,772 issued Aug. 3, 1982, analogous compounds are disclosed in which penicillins and beta-lactamase inhibitors such as penicillanic acid 1,1-dioxide, clavulanic acid and 6-beta-halopenicillanic acids are linked via 1,1-alkanediol groups.

In copending application Ser. No. 300,421, filed Sept. 9, 1981, now abandoned, and assigned to the same assignee, compounds of formula (IX) are disclosed wherein $R_1$ is

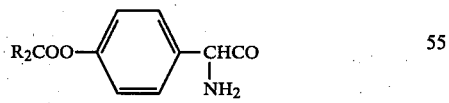

and $R_2$ is certain alkyl or alkoxy groups.

Ampicillin, 6-[D-(2-amino-2-phenylacetamido)]-penicillanic acid is disclosed in U.S. Pat. No. 2,985,648. Amoxicillin, 6-[D-(2-amino-2-[p-hydroxyphenyl-]acetamide)]penicillanic acid is known from U.S. Pat. No. 3,192,198 and U.S. Pat. No. Re. 28,744. p-Acyl derivatives of amoxicillin are disclosed in U.S. Pat. Nos. 2,985,648, 3,520,876 and 4,053,360.

2-beta-Acetoxymethyl-2-alpha-methyl-penam-3-alpha-carboxylic acid 1,1-dioxide is disclosed as being a useful beta-lactamase inhibitor in U.S. Pat. No. 4,256,733.

2-beta-Chloromethyl-2-alpha-methyl-penam-3-alpha-carboxylic acid 1,1-dioxide is disclosed as a beta-lactamase inhibitor in British Patent Application No. 2,070,592.

Bis-Esters of 1,1-alkanediols with 6-beta-hydroxymethylpenicillanic acid 1,1-dioxide are disclosed in U.S. Pat. No. 4,342,768. The corresponding derivatives of 6-alpha-hydroxymethylpenicillanic acid 1,1-dioxide are disclosed in copending application Ser. No. 338,794, filed Jan. 11, 1982, assigned to the same assignee. 6-Aminoalkyl penicillanic acid 1,1-dioxide beta-lactamase inhibitors are disclosed in copending application Ser. No. 388,324, filed June 14, 1982 now abandoned and assigned to the same assignee.

SUMMARY OF THE INVENTION

The present invention provides compounds of the formula (I) which are antibacterial agents and certain intermediates therefore. The antibacterial compounds of formula (I) are efficiently absorbed from the mammalian gastrointestinal tract and are then rapidly transformed into the component penicillin, PCOOH, and/or beta-lactamase inhibitor, BCOOH, or salts of the respective components. Said invention compounds are of the formula

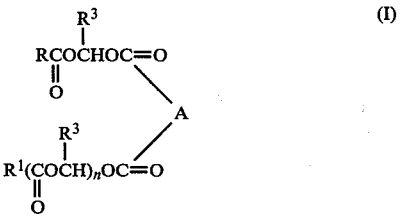

or a pharmaceutically acceptable cationic or acid addition salt thereof wherein A is $(C_1-C_{12})$alkylene, $(C_1-C_{12})$alkylidene. $(C_3-C_7)$cycloalkylene, phenylene, naphthalene,

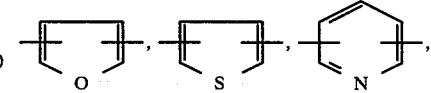

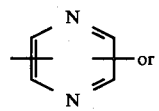 or said alkylene or alkylidene substituted by phenyl or carboxy;

$R^3$ is H or $(C_1-C_3)$alkyl, n is zero or 1,

R and $R^1$ are different and

R is P or B, when n is zero, $R^1$ is H, $(C_1-C_4)$alkyl, benzyl, $CH(R^3)Cl$, $CH(R^3)I$ or tetrabutylammonium, and when n is 1, $R^1$ is P or B;

P is

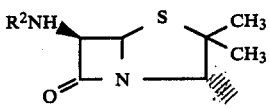

where R² is H,

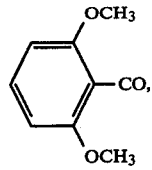

$C_6H_5OCH_2CO$,

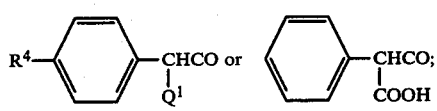

Q¹ is H, $NH_2$, $N_3$, benzyloxycarbonylamino, 4-nitrobenzyloxycarbonylamino or 1-methyl-2-methoxycarbonylvinylamino; R⁴ is H, OH, ($C_2$-$C_7$)alkanoyloxy, ($C_2$-$C_7$)alkoxycarbonyloxy or $R^5C_6H_4COO$, and R⁵ is H, ($C_1$-$C_4$)alkyl, ($C_1$-$C_4$)alkoxy, F, Cl, Br or CN; and B is

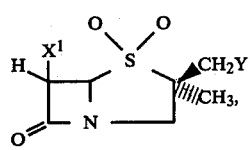

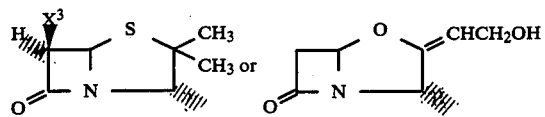

where,
when Y is H, X¹ is H, $CH_2OH$ or $CH(R^8)$—$NH_2$ where R⁸ is H or $CH_8$;
when Y is Cl or $CH_3COO$, X¹ is H; and
X³ is Cl Br or I.

The pharmaceutically active compounds and salts of formula (I) are those wherein a. when n is zero, R¹ is ($C_1$-$C_4$)alkyl, H or an alkali metal salt thereof, preferred such salts are the sodium and potassium salts; and b. when n is 1, one of R and R¹ is B and the other is P where R² and R⁴ are defined above and Q¹ is H or $NH_2$.

Particularly preferred such antibacterial agents are those wherein when n is zero, R¹ is H or a cationic or acid addition salt thereof and when n is 1, R² is

i.e., compound of the formulae (II) or (III) where R¹ is H, and (IV)

(II)

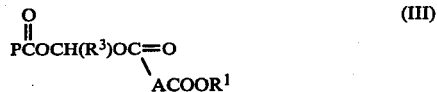

(III)

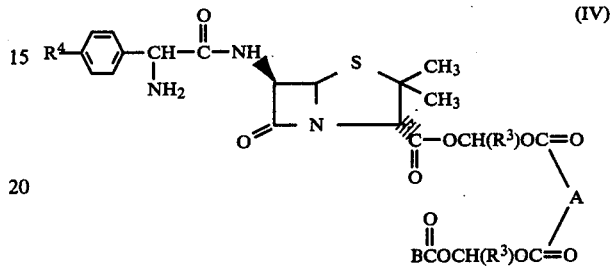

(IV)

Particularly preferred values for A are ($C_1$-$C_{12}$)alkylene, ($C_1$-$C_{12}$)alkylidene, ($C_3$-$C_7$)cycloalkylene or phenylene. More particularly preferred compounds of formula (I) are those wherein A is $(CH_2)_m$,

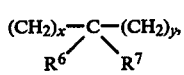

cyclohexylene or phenylene where m is 1-8, x and y are each zero or 1-6, R⁶ is H or ($C_1$-$C_4$)alkyl and R⁷ is ($C_1$-$C_4$)alkyl.

Even more particularly preferred values of A are $(CH_2)_2$, $(CH_2)_3$, $(CH_2)_4$, $(CH_2)_8$, $C(CH_3)_2$, 1,4-phenylene and trans-1,4-cyclohexylene.

Particularly preferred carboxylic acids, BCOOH, from which compounds of the invention are derived, are 6-beta-bromopenicillanic acid, clavulanic acid and the 1,1-dioxo acids of the formula

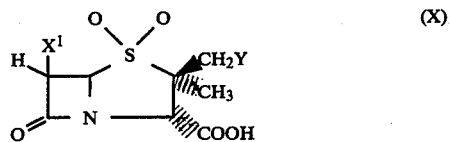

(X)

where Y and X¹ are as previously defined.

More particularly preferred values of B are those derived from the carboxylic acids of formula (X) wherein Y is H and X¹ is H or $CH_2OH$ and most particularly preferred are those wherein Y and X¹ are both H, i.e. those derived from penicillanic acid 1,1-dioxide.

In the invention compounds of the formula (IV), above, and (VI) below, wherein R² is 4-$R^4C_6H_4CH(Q^1)CO$,

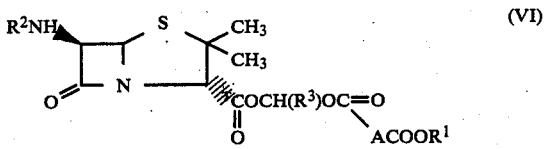

(VI)

particularly preferred values for $R^4$ include H, OH, acetoxy, t-butylcarbonyloxy or isobutoxycarbonyloxy.

Particularly preferred values for $Q^1$ in the compounds of the invention containing this variable are H, $NH_2$, $N_3$, benzyloxycarbonylamino and 1-methyl-2-methoxycabonylvinylamino, and H or $NH_2$ being especially preferred values in the antibacterial agents of the invention.

Other particularly preferred compounds provided herein are of the formulae (V) and (VII)

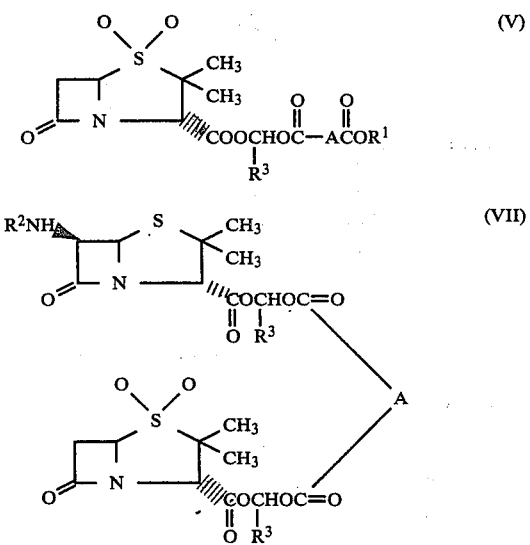

where $R^1$ is H, $(C_1-C_4)$alkyl, benzyl, $CH_2Cl$, $CH_2I$ or a carboxylate salt forming cation. Particularly preferred such cations are tetrabutylammonium or an alkali metal cation. Preferred alkali metal cations are sodium and potassium.

Particularly preferred compounds of the invention are those wherein $R^3$ is H.

The invention compounds containing one of the moieties P or B, as defined above, are valuable as intermediates or as active prodrugs for the particular penicillin or beta-lactamase inhibitor contained therein. For example, compounds of formula (V) wherein $R^3$ are as defined above and $R^1$ is $(C_1-C_4)$alkyl, H, or a pharmaceutically acceptable cation are valuable prodrugs for sulbactam; the compounds of formula (VI) wherein $R^2$ is $4-R^4C_6H_4CH(Q^1)CO$ and $R^4$ is H or OH, $Q^1$ is $NH_2$; A and $R^3$ are as previously defined and $R^1$ is $(C_1-C_4)$alkyl or H or pharmaceutically acceptable cationic or acid addition salts thereof, are useful prodrugs for ampicillin ($R^4=H$) or amoxicillin ($R^4=OH$). Those compounds (V) and (VI) wherein $R^1$ is, for example, $CH_2Cl$, benzyl or tetrabutylammonium and compounds (VI) having a $Q^1$ group, that is other than H or $NH_2$, are useful as intermediates.

Likewise, the invention compounds containing both B and P moieties are of value either as intermediates or as antibacterial agents which are efficiently absorbed in the mammalian gastrointestinal tract where they are rapidly transformed into the component penicillin and beta-lactamase inhibitor in substantially equimolar amounts. The invention compounds of formula (I) having a free amino group in one or both of the moieties P and B, as defined above, are capable of forming acid addition salts. Such salts with pharmaceutically acceptable acids are included in the invention. Examples of such acids are hydrochloric, hydrobromic, hydriodic, sulfuric, phosphoric, citric, malic, tartaric, maleic, fumaric, gluconic, saccharic, benzenesulfonic, p-toluenesulfonic, p-chlorobenzenesulfonic and 2-napththalenesulfonic acids.

DETAILED DESCRIPTION OF THE INVENTION

This invention relates to derivatives of penicillanic acid which is represented by the following structural formula:

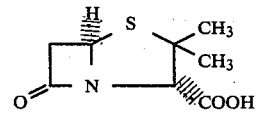

In derivatives of penicillanic acid, broken line attachment ($'''$) of a substituent to the bicyclic nucleus indicates that the substituent is below the plane of the nucleus. Such a substituent is said to be in the alpha-configuration. Conversely, broad line attachment (▶─) of a substituent of the bicyclic nucleus indicates that the substituent is above the plane of the nucleus. This latter configuration is referred to as the beta-configuration. As used herein a solid line attachment (—) of a substituent to the bicyclic nucleus indicates that the substituent can be in either the alpha-configuration or the beta-configuration.

Compounds of the invention of formulae (I)–(IX) are named as diesters of the dicarboxylic acids of formula HOOC-A-COOH where A is as previously defined. For example, the compound of formula (VIII) where $R^4$ is hydrogen, $Q^1$ is $NH_2$ and A is $(CH_2)_2$ is designated as 6-(2-amino-2-phenylacetamido)penicillanoyloxymethyl 1,1-dioxopenicillanoyloxymethyl succinate; the compound (VIII) where $R^4$ is hydroxy, A is $(CH_3)_2C$ and $Q^1$ is azido is designated as 6-[2-azido-2-(p-hydroxyphenyl)acetamido]-penicillanoyloxymethyl 1,1-dioxopenicillanoyloxymethyl dimethylmalonate; and the compound of formula (V) where $R^1$ is benzyl, $R^3$ is H and A is $(CH_2)_3$ is designated benzyl 1,1-dioxopenicillanoyloxymethyl glutarate.

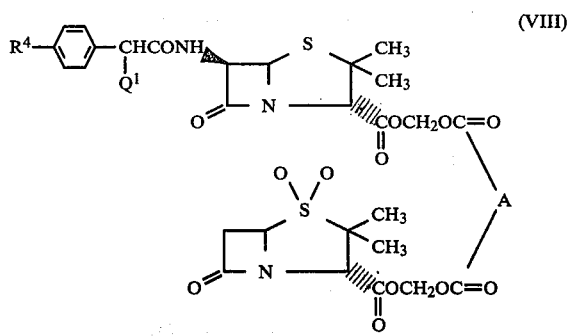

Additionally, throughout this specification, whenever reference is made to compound of the invention having a pencillin moiety, P as defined above wherein $R^2$ is the substituent

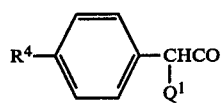

where $R^4$ and $Q^1$ are as defined above (but $Q^1$ is other than H), if not already so indicated, it is understood that this refers to a compound in which said substituent has the D-configuration.

The compounds of formula (I) can be prepared by many of the methods known in the art for synthesis of esters. However, the preferred method involves salt formation by condensation of a carboxylate salt and halomethyl ester wherein "halo" is a leaving group X. Preferred values of X are Cl, Br, I, $CH_3SO_2O$, p-$CH_3C_6H_4SO_2O$. For example, four general methods are outlined below for the case where $R^3$ is H, R is P, $R^1$ is B and P is

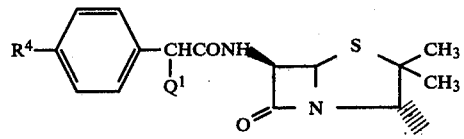

where $Q^1$ is $N_3$, $C_6H_5CH_2OCONH$, p-$NO_2C_6H_4OCONH$ or

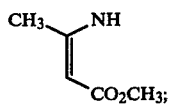

B is

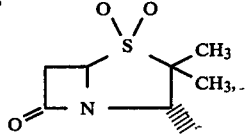

M is a carboxylate salt forming cation, preferably Na, K or $N(C_4H_9)_4$ cations and X is as defined above.

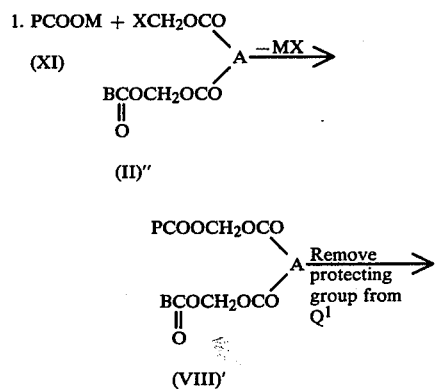

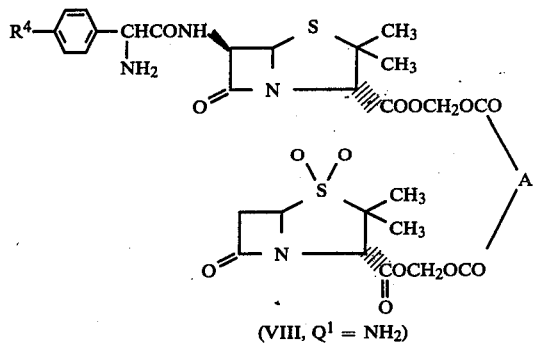

2. $PCOOCH_2X$ + 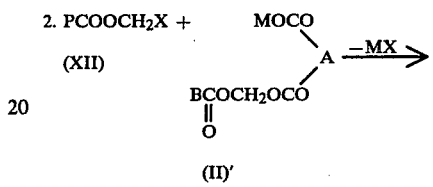

(VIII)' ⟶ (VIII, $Q^1 = NH_2$)

3. 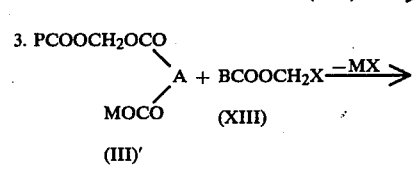

(VIII)' ⟶ (VIII, $Q^1 = NH_2$)

4. 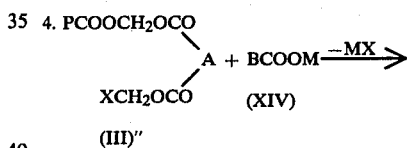

(VIII)' ⟶ (VIII, $Q^1 = NH_2$)

In each of the above reactions to form the amino-protected product of formula (VIII)', the respective carboxylate salt and halomethyl ester are contacted in approximately equimolar amounts in the presence of a polar organic solvent at a temperature of from about 0° to 80° C. and preferably from about 25° to 50° C. While, as stated above, approximately equimolar amounts of reactants are employed, an excess of either the carboxylate salt or halomethyl ester, up to a tenfold molar excess can be employed. A wide variety of solvents can be used for this reaction; however, it is usually advantageous to use a relatively polar organic solvent to minimize the reaction time. Typical solvents which can be employed include N,N-dimethylformamide, N,N-dimethylacetamide, N-methylpyrrolidone, dimethylsulfoxide, ethyl acetate, dichloromethane, acetone and hexamethylphosphoric triamide. The time required for the reaction to reach substantial completion varies according to a number of factors, such as the nature of the reactants, the reaction temperature and solvent. However, at about 25° C. reaction times of from about 10 minutes to about 24 hours are commonly employed.

The desired amino-protected compound of formula (VIII)' is then isolated by methods well known to those of skill in the art. For example, the reaction mixture is taken up in a water immiscible solvent, e.g. ethyl acetate, chloroform or dichloromethane, washed with water, brine and dried. Evaporation of solvent provides the intermediate of formula (VIII)′ which can be purified, if desired, e.g. by chromatography on silica gel.

The removal of the amino-protecting group from the intermediate (VIII)′ is carried out by methods well known in the art, see, e.g. Gross et al. in "The Peptides, Analysis, Synthesis, Biology", Academic Press, New York, N.Y., Vol. 3, 1981, but due regard must be given to the lability of the beta-lactam ring and to the ester linkages. For example, when $Q^1$ is 1-methyl-2-methoxycarbonylvinylamino, the protecting group (1-methyl-2-methoxycarbonylvinyl) can be removed simply by treating the compound of formula (VIII)′ with one equivalent of a strong aqueous acid, e.g. hydrochloric acid, in a reaction inert solvent, at a temperature in the range of from −10° to 30° C. In a typical procedure, the enamine intermediate is treated with one equivalent of hydrochloric acid in aqueous acetone. The reaction is usually complete within a short time, e.g. within one hour. Then the acetone is removed by evaporation in vacuo, and the methyl acetoacetate by-product is removed by extraction with ether. Finally, the compound of formula (VIII, $Q^1=NH_2$) is recovered by lyophilization as its hydrochloride salt.

Intermediate compounds of formula (VIII) wherein $Q^1$ is azido, benzyloxycarbonylamino or 4-nitrobenzyloxycarbonylamino can be converted to the corresponding amino compound (VIII, $Q^1=NH_2$) by subjecting the intermediate compound (VIII) to conditions commonly employed for catalytic hydrogenolysis. The intermediate is stirred or shaken under an atmosphere of hydrogen, or hydrogen, optionally mixed with an inert diluent such as nitrogen or argon, in the presence of a catalytic amount of a hydrogenolysis catalyst. Convenient solvents for this hydrogenolysis are lower-alkanols, such as methanol and isopropanol; ethers, such as tetrahydrofuran and dioxane; low molecular weight esters, such as ethyl acetate and butyl acetate; chlorinated hydrocarbons, such as dichloromethane and chloroform; water; and mixtures of these solvents. However, it is usual to choose conditions under which the starting material is soluble. The hydrogenolysis is usually carried out at a temperature in the range from 0° to 60° C. and at a pressure in the range from 1 to 10 atmospheres, preferably about 3-4 atmospheres. The catalysts used in this hydrogenolysis reaction are the type of agents known in the art for this kind of transformation, and typical examples are nickel and the noble metals, such as palladium, platinum and rhodium. The catalyst is usually used in an amount from 0.5 to 5.0, and preferably about 1.0, times the weight of the intermediate formula (VIII). It is often convenient to suspend the catalyst on an inert support, a particularly convenient catalyst is palladium suspended on an inert support such as carbon.

The remaining invention compounds containing a pencillin moiety, P, such as compounds of formula (III), (VI), (VII) or (VIII), wherein $R^2$ is

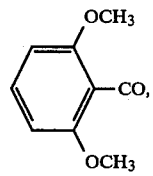

$C_6H_5OCH_2CO$ or

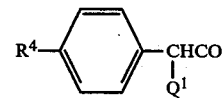

where $Q^1$ is H and not containing an amino group in B, are made, for example, by the same methods described above, except, of course, the last step, removal of the amino-protecting group, is not required.

All of the remaining beta-lactamase containing invention compounds of formula (I) or (II) are also prepared by the above procedures starting from the appropriate precursors, except for those wherein B is of the formula

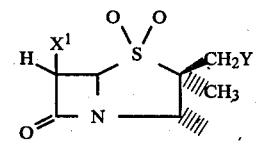

where Y is H and $X^1$ is $CH(R^8)NH_2$ and $R^8$ is H or $CH_3$. A preferred procedure for preparing the compounds (I) or (II) containing the latter beta-lactamase moieties starts with the amino protected beta-lactamase such as e.g. 6-alpha-(benzyloxycarbonylaminomethyl)penicillanate 1,1-dioxide. This is converted into a salt, BCOOM, where M is Na, K or tetrabutylammonium and the salt is then reacted as described above, for example, with an intermediate of formula (III)′ or of the formula $XCH(R^3)OCOA-COOR^1$. The amino-protecting group is subsequently removed, e.g. by hydrogenolysis as described above, to provide the desired pharmaceutically active compound wherein $X^1$ is $CH(R^2)NH_2$. Of course, if the desired product is of the formula

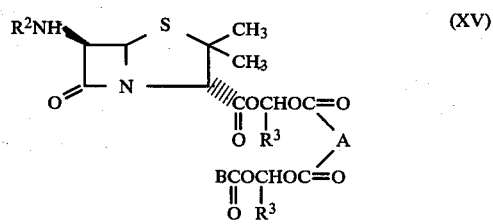

(XV)

where $R^2$ is H or

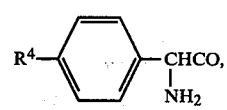

any amino-protecting group present in the penicillin moiety can be removed simultaneously.

An alternate process for preparation of antibacterial compounds of formula (VIII) where $Q^1$ is $NH_2$ employs an intermediate of formula

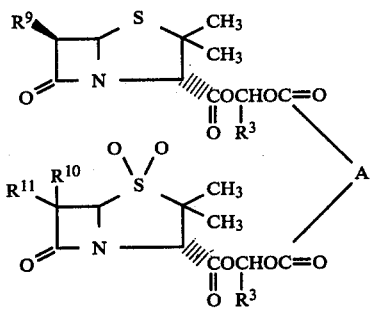

(XVI)

where $R^9$ is $Q^2$ or

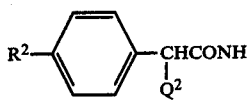

and $Q^2$ is azido, benzyloxycarbonylamino or p-nitrobenzyloxycarbonylamino; $R^{10}$ is H, Cl, Br or I and $R^{11}$ is Cl, Br or I. The intermediate (XVI) upon catalytic hydrogenation, e.g. by the method described above for hydrogenolysis of azido, or benzyloxycarbonylamino compounds of formula (VIII), is simultaneously hydrogenolyzed at the $Q_2$, $R^{10}$ and/or $R^{11}$ substituents to provide invention compounds of formula (VIII), $Q^1=NH_2$.

The intermediates (XVI) are obtained by methods analogous to those described above for preparation of intermediates of formula (VIII)', but employing a $R^{10},R^{11}$-substituted 1,1-dioxopenicillanate in place of the corresponding unsubstituted 1,1-dioxopenicillanic acid, its salts or derivatives of formulae (II)', (II)" or (XIII).

Methods for preparation of the requisite $R^{10}$, $R^{11}$-disubstituted 1,1-dioxopenicillanic acids and salts thereof are taught in U.S. Pat. Nos. 4,234,579, 4,342,772 and Belgian Pat. No. 882,028.

The intermediates of formula (II) can be obtained, for example, as outlined below for the case where $R^3=H$.

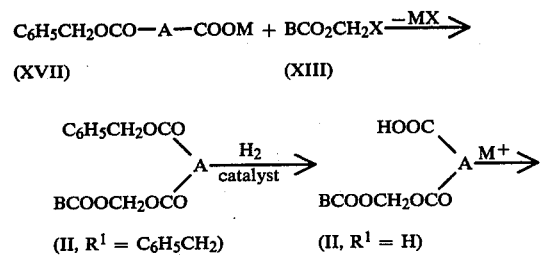

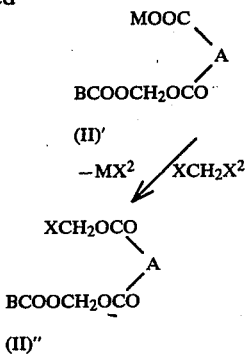

where A, B, M and X are as defined above and $X^2$ is X or a better leaving group than X, e.g., when X is Cl, $X^2$ may be Cl, Br, I, $OSO_2Cl$, $OSO_2CH_3$ or $p-CH_3OC_6H_4SO_2O$. Particularly preferred values for $X^2$ are Br and I.

The first step illustrated above, wherein the salt of the benzyl half ester is reacted with the halomethyl ester of 1,1-dioxopenicillanic acid to form compounds of formula (II), where $R^1$ is benzyl, is carried out as described above for preparation of the intermediates of formula (VIII).

The selective removal of benzyl group is typically carried out by catalytic hydrogenolysis by the same methods and conditions as those described above for the conversion of compounds of formula (VIII) wherein $Q^1$ is azido, benzyloxycarbonylamino or 4-nitrobenzyloxycarbonylamino to the corresponding invention compounds of formula (VIII) where $Q^1=NH_2$. An especially preferred method employs palladium-on-carbon catalyst at 3-4 atmospheres pressure and use of tetrahydrofuran or ethyl acetate as solvent. The carboxylic acid of formula (II, $R^1$ is H) may then be isolated by standard methods or the acid can be conveniently reacted with an appropriate base to form the corresponding salt of formula (II)' where M is a carboxylate salt forming cation as defined above. A preferred method for obtaining the sodium and potassium salts of formula (II)' employs the sodium or potassium salt of 2-ethylhexanoic acid as base. Typically, the carboxylic acid of formula (II) is dissolved in ethyl acetate, an equimolar amount of sodium (or potassium) 2-ethylhexanoate added with stirring and the precipitated salt of formula (II)' collected by filtration and washed.

The salts of formula (II)', wherein M is tetrabutylammonium can be obtained from the corresponding acid, sodium or potassium salt. For example, when a carboxylic acid of formula (II) is employed, it is typically reacted with an equimolar amount of tetrabutylammonium hydroxide in the presence of a water immiscible organic solvent, preferably chloroform. The solvent layer is separated and the product isolated by evaporation of solvent.

The intermediates of formula (II)" are obtained by elimination of the elements of $MX^2$ in the reaction of the corresponding compounds of formula (II)" and $XCH_2X^2$, where M, X and $X^2$ are as defined above. The reaction is carried out employing the same methods and conditions as described above for preparation of intermediates of formula (VIII).

The intermediates of formula (III) can be obtained by employing the same methods and conditions described above for preparation of intermediates of formula (II), but using the analogous pencillin derivatives, PCOOCH(R³)X instead of BCOOCH(R³)X, e.g. as outlined below for the case where R³ is H.

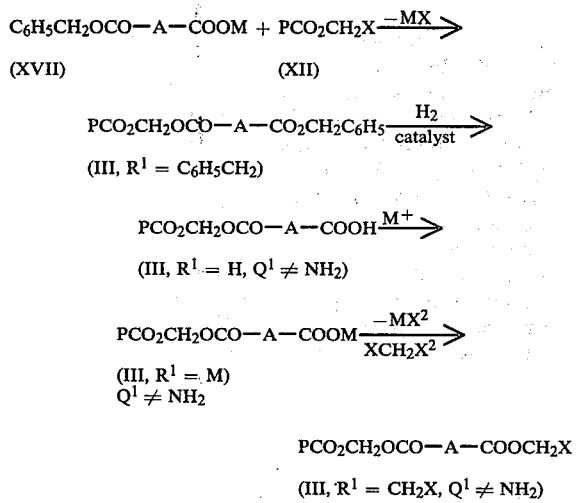

$C_6H_5CH_2OCO—A—COOM + PCO_2CH_2X \xrightarrow{-MX}$ (XVII)    (XII)

$PCO_2CH_2OCO—A—CO_2CH_2C_6H_5 \xrightarrow{H_2}{catalyst}$ (III, $R^1 = C_6H_5CH_2$)

$PCO_2CH_2OCO—A—COOH \xrightarrow{M^+}$ (III, $R^1 = H$, $Q^1 \neq NH_2$)

$PCO_2CH_2OCO—A—COOM \xrightarrow[XCH_2X^2]{-MX^2}$ (III, $R^1 = M$)
$Q^1 \neq NH_2$ $PCO_2CH_2OCO—A—COOCH_2X$ (III, $R^1 = CH_2X$, $Q^1 \neq NH_2$)

where A, M, X and $X^2$ and P are as defined above. The amino-protecting group can be removed as described above for the conversion of intermediate compounds of formula (VIII) to amino compounds of the same formula.

The invention compounds wherein $R^4$ is acyloxy or alkoxycarbonyloxy as defined above can be prepared starting with the appropriate p-acylamoxicillin or p-alkyloxycarbonylamoxicillin prepared, e.g. by acylation of 6-aminopenicillanic acid with the appropriate acid of the formula

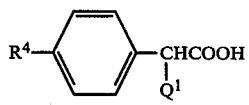

where $Q^1$ is as defined above and $R^4$ is formyloxy, alkanoyloxy or alkoxycarbonyloxy, or a carboxyl activated derivative thereof by methods disclosed in U.S. Pat. No. 4,053,360. Alternatively, the intermediates of formula (VIII)' and their precursors of formula (VI) and (XIII) wherein $R^4$ is hydroxy can be prepared as described above and the intermediate of formula (VIII', $R^4$=OH) subsequently acylated or alkoxycarbonylated to provide the corresponding compound of formula (VIII) wherein $R^4$ is formyloxy, alkylcarbonyloxy, alkoxycarbonyloxy or $R^5C_6H_4COO$ as defined above.

The acylation or alkoxycarbonylation of the intermediate of formula (VIII)' wherein $R^4$ is hydroxy and $Q^1$ is as previously defined can be carried out e.g., by reacting said compound of formula (VIII)' with the appropriate acid chloride or acid anhydride or mixed anhydride. The reaction is ordinarily carried out in the presence of a reaction-inert solvent system. In a typical procedure, from 0.5 to 2.0 molar equivalents, and preferably about 1 molar equivalent, of the appropriate acid chloride or acid anhydride is contacted with the starting compound of formula (VIII) wherein $R^4$ is hydroxy, in a reaction-inert solvent, in the presence of a tertiary amine, at a temperature in the range from $-10°$ to $30°$ C. Reaction-inert solvents which can be used in this acylation are: chlorinated hydrocarbons, such as chloroform and dichloromethane; ethers, such as diethyl ether and tetrahydrofuran; low molecular weight esters, such as ethyl acetate and butyl acetate; low molecular weight aliphatic ketones, such as acetone and methyl ethyl ketone, tertiary amides, such as N,N-dimethylformamide and N-methylpyrrolidone; acetonitrile; and mixtures thereof. The tertiary amine is normally used in an amount equivalent to the starting acid chloride or acid anhydride, and typical tertiary amines which can be used are triethylamine, tributylamine, diisopropylethylamine, pyridine and 4-dimethylaminopyridine.

In addition to being useful intermediates for production of the conjugate antibacterial compounds of formula (I) where n is 1, the carboxylic acids and salts of formula (II) through (VI) wherein $R^1$ is H or an alkali metal cation, e.g. Na or K, are useful prodrug forms of the beta-lactamase inhibitors, BCOOH, or penicillin, PCOOH where B and P are as previously defined. Particularly preferred such beta-lactamase inhibiting compounds are those of the formula (V) where $R^1$ is H, Na or K and A and $R^1$ are as previously defined, which are useful prodrugs of penicillanic acid 1,1-dioxide (sulbactam).

Likewise, the penicillin derivatives of formula (VI) wherein $R^1$ is H, Na or K and $R^2$ is 2,6-$(CH_3O)_2C_6H_3CO$, $C_6H_5OCH_2CO$ or 4-$R^4$-$C_6H_4CH(NH_2)CO$ and the pharmaceutically acceptable acid addition salts of such compounds wherein $R^2$ has the latter value, are useful prodrugs for the corresponding penicillins. Particularly preferred such derivatives are of the formula (VI) where $R^2$ is

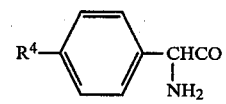

and especially those wherein $R^4$ is H or OH which are useful prodrug forms of the well known antibacterial agents ampicillin and amoxicillin.

The compounds of the formula (I) which contain a free amino group will form acid addition salts, and these acid addition salts are considered to be within the scope and purview of this invention. Said acid addition salts are prepared by standard methods for penicillin compounds, for example by combining a solution of the compound of formula (I) in a suitable solvent (e.g. water, ethyl acetate, acetone, methanol, ethanol or butanol) with a solution containing a stoichiometric equivalent of the appropriate acid. If the salt precipitates, it is recovered by filtration. Alternatively, it can be recovered by evaporation of the solvent, or, in the case of aqueous solutions, by lyophilization. Of particular value are the sulfate, hydrochloride, hydrobromide, nitrate, phosphate, citrate, tartrate, pamoate, perchlorate, sulfosalicylate, benzenesulfonate, 4-toluenesulfonate and 2-naphthylenesulfonate salts.

The compounds of the formula (I), and the salts thereof, can be purified by conventional methods for penicillin compounds, e.g. recrystallization or chromatography, but due regard must be given to the lability of the beta-lactam ring systems and the ester linkages.

Certain of the invention compounds of formula (IV) which contain a beta-lactamase inhibitor residue, B, are not adequately stable to the hydrogenolysis conditions described above, for example, certain of such compounds wherein B is

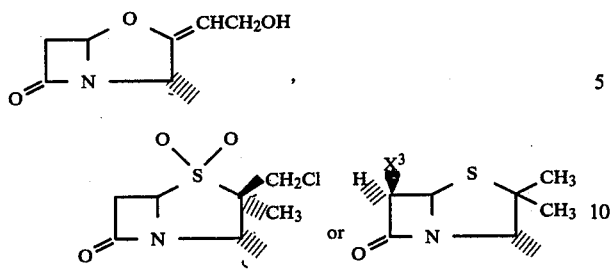

where $X^3$ is Cl, Br, or I. An especially preferred method for preparing invention compounds (IV) containing one of the above B moieties involves the use of a protecting group which is removable by mild hydrolysis or by mild reduction methods, for example as outlined below.

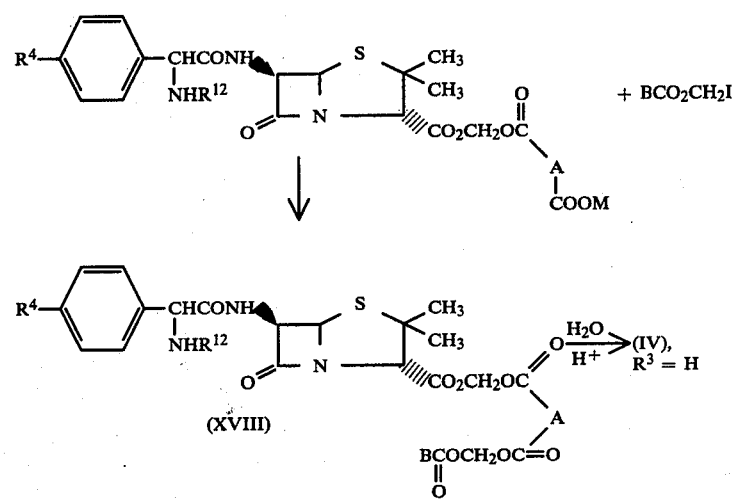

where A, B and $R^4$ are as defined above, M is a cation, preferably sodium, potassium or tetrabutylammonium, and $R^{12}$ is an amino protecting group which is removable by mild hydrolysis or mild reduction methods. Examples of suitable groups are triphenylmethyl and

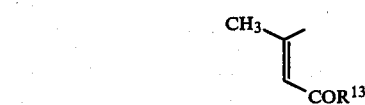

where $R^{13}$ is alkoxy having from one to three carbon atoms or $NH_2$.

Alternatively, the compounds of formula (IV) which are not stable to hydrogenolysis conditions can be prepared by the following method.

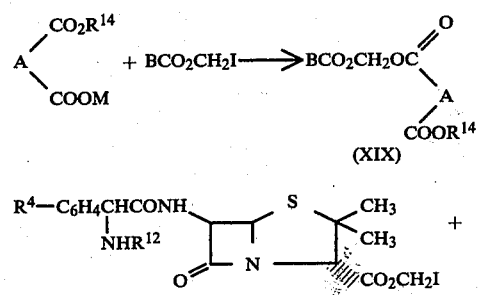

(XIX) → (XVIII) → (IV)

where A, M and $R^{12}$ are as defined above, B is the residue of a beta-lactamase inhibitor as defined above, preferably one which is unstable to hydrogenolysis conditions and $R^{14}$ is a carboxy protecting group removable by mild hydrolysis or reduction such as p-$NO_2C_6H_4CH_2$, $R^aR^bR^cSi$ or $R^aR^bR^cSiCH_2CH_2$ where each of $R^a$, $R^b$ and $R^c$ is alkyl having from one to twelve carbon atoms, aryl or aralkyl having from five to eight carbon atoms.

As set forth above under the Description of the Prior Art, many of the beta-lactamase inhibitors employed as starting material for syntheses of the compounds of the present invention are known in the art. 6-alpha-Hydroxymethylpenicillanic acid 1,1-dioxide is prepared by reaction of benzyl 6,6-dibromopenicillanate in reaction-inert solvent at −70° to −20° C. with t-butyllithium or t-butylmagnesium chloride. The resulting enolate is then treated with formaldehyde and the resulting mixture of benzyl 6-bromo-6-hydroxymethylpenicillanate isomers is isolated. This mixture is oxidized to the corresponding 1,1-dioxide, e.g. employing an organic peracid such as m-chloroperbenzoic acid. The isolated sulfone is hydrogenated in the presence of a palladium-on-calcium carbonate catalyst which results in formation of the desired 6-alpha-hydroxymethylpenicillanic acid sulfone.

As noted above 6-beta-hydroxymethylpenicillanic acid sulfone is provided in U.S. Pat. No. 4,342,768 issued Aug. 3, 1982.

A preferred method for preparing the 6-aminomethyl- and 6-(1-amino)ethyl-penicillanic acid 1,1-dioxides also starts with benzyl 6,6-dibromopenicillanate. This is reacted with one molar equivalent of methylmagnesium bromide in an ether solvent at −100° to −50° C. for a brief of time. The resulting mono-Grignard reagent is contacted with about 0.5 molar equivalents of benzyloxycarboxamidomethyl acetate or 1-benzyloxycarboxamidoethyl acetate at the same temperature for about 0.5 to 2 hours to afford a mixture of epimers of, e.g. benzyl 6-bromo-6-benzyloxycarbonylaminomethylpenicillanate. This is reacted in the next stpe or the mixture can be separated by column chromatography. In the next step the bromine atom is removed, e.g., by halogenolysis with tri-n-butyltin hydride, optionally in the presence of a small amount of a free radical initiator, preferably 2,2'-azobisisobutyronitrile (AIBN), and hydrocarbon solvent, e.g., benzene or toluene at 60°–100° C. The 6-beta-benzyloxycarbonylaminomethylpenicillanate ester is then recovered by crystallization (if a mixture of epimers is employed as starting material) and the 6-alpha epimer is recovered by evaporation of the mother liquor and chromatography of the residue. The epimeric sulfides are then oxidized to sulfones, e.g., as described above for the 6-hydroxymethylpenicillanates and the benzyl protecting groups removed by standard hydrogenolysis methods.

When contemplating therapeutic use for a salt of an antibacterial compound of this invention, it is necessary to use a pharmaceutically-acceptable salt; however, salts other than these can be used for a variety of purposes. Such purposes include isolating and purifying particular compounds, and interconverting pharmaceutically-acceptable salts and their non-salt counterparts.

The conjugate invention compounds of formula (I) where n is 1, one of R and $R^1$ is B and the other is P, as defined above where $R^2$ is 2,6-dimethoxybenzoyl, phenoxyacetyl or

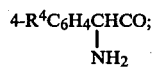

the carboxylic acids, lower alkyl esters and the alkali metal salts thereof of the formula (II) or (V) as well as the carboxylic acids, lower alkyl esters, and alkali metal salts of the compounds of formula (VI) where $R^2$ is 2,6-dimethoxybenzoyl, phenoxyacetyl or

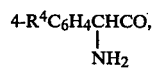

as well as the acid addition salts of those compounds containing a free amino ($NH_2$) group, all possess in vivo antibacterial activity in mammals. This activity can be demonstrated by standard techniques for penicillin compounds. For example, the above compound of formula (I), (II), (V) or (VI) is administered to mice in which acute infections have been established by intraperitoneal inoculation with a standardized culture of a pathogenic bacterium. Infection severity is standardized such that the mice receive one to ten times the $LD_{100}$ ($LD_{100}$: the minimum inoculation required to consistently kill 100 percent of control mice). At the end of the test, the activity of the compond is assessed by counting the number of servivors which have been challenged by the bacterium and also have received the invention compound. The antibacterial compounds of formula I as well as the carboxylic acids, esters and alkali metal salts of formulae (II), (V) and (VI) can be administered by both the oral (p.o.) and subcutaneous (s.c.) route.

The in vivo activity of the antibacterial compounds of this invention makes them suitable for the control of bacterial infections in mammals, including man, by both the oral and parenteral modes of administration. The compounds are useful in the control of infections caused by susceptible bacteria in human subjects.

An invention compound, for example, one of formula (VIII, $Q^1=NH_2$) wherein $R^4$ is other than hydrogen breaks down to 6-(2-amino-2-[4-hydroxyphenyl]-acetamido)penicillanic acid (amoxicillin) and penicillanic acid 1,1-dioxide (sulbactam) after administration to a mammalian subject by both the oral and parenteral route. Sulbactam then functions as a beta-lactamase inhibitor, and it increases the antibacterial effectiveness of the amoxicillin. Similarly, a compound of formula (VIII) wherein $R^4$ is hydrogen breaks down to 6-(2-amino-2-phenylacetamido)penicillanic acid (ampicillin) and sulbactam. Thus, the conjugate antibacterial compounds of the formula (I) will find use in the control of bacteria which are susceptible to an approximately equimolar mixture of penicillin, PCOOH, and BCOOH, for example a 1:1 mixture of amoxicillin and sulbactam for the compound (VIII) where $Q^1$ is $NH_2$ and $R^4$ is HO or ampicillin and sulbactam for the corresponding compound where $R^4$ is H. Example of such bacteria are susceptible strains of *Escherichia coli* and *Staphylococcus aureus*.

The carboxylic acids of the formula (II), and especially those of the formula

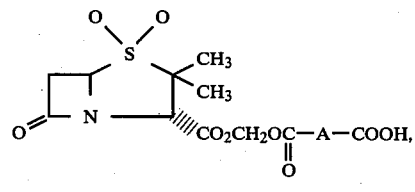

(V, $R^1 = R^3 = H$)

the alkyl esters having from one to four carbon atoms in said alkyl, and the alkali metal salts, especially the sodium and potassium salts thereof, are useful as oral or parenteral prodrug forms of sulbactam and as such have the therapeutic applications as a betalactamase inhibitor, for example, the applications disclosed for sulbactam in U.S. Pat. No. 4,234,579.

The antibacterial carboxylic acids, esters and salts of the formula (VI) as defined above, especially those of the formula (XX)

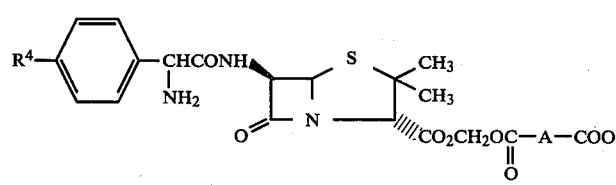

($C_1$–$C_4$)alkyl esters and the pharmaceutically acceptable acid addition and cationic salts thereof, are useful as oral and parenteral prodrug forms of amoxicillin (when $R^4$ is other than hydrogen) and ampicillin (when $R^4$ is hydrogen).

Examples of pharmaceutically acceptable acid addition salts of the invention compounds of formula (I) containing a free NH2 group in $Q^1$ or $X^1$ include the salts of hydrochloric, hydrobromic, sulfuric, phosphoric, acetic, maleic, malic, fumaric, succinic, lactic, tartaric, citric, gluconic, saccharic, benzenesulfonic, p-toluenesulfonic, p-chlorobenzenesulfonic and 2-naphthalenesulfonic acids.

Examples of pharmaceutically acceptable cationic salts of the carboxylic acid compounds of formulae (II), (III), (V) or (VI) include the alkali metal salts such as the sodium, and potassium salts; as well as the ammonium salt and salts of pharmaceutically acceptable amines such as N-methylglucamine, N,N-dibenzylethylenediamine, ethanolamine and procaine.

The above prodrugs of formula (II) and (III) where $R^1$=(C1-C4)alkyl, H or a pharmaceutically acceptable salt thereof can also be administered as physical mixtures of the two compounds, preferably said mixture is one having a weight ratio in the range of from about 1:3 to 3:1. Such mixtures upon administration to a mammalian subject by either the oral or parenteral route would also break down to form mixtures of the beta-lactamase inhibitor (BCOOH) and the penicillin (PCOOH).

In determining whether a particular strain of *Escherichia coli* or *Staphylococcus aureus* is sensitive to a particular therapeutic compound or mixture, the in vivo test described earlier can be used. Alternatively, e.g., the minimum inhibitory concentration (MIC) of a 1:1 mixture of amoxicillin and sulbactam or ampicillin/sulbactam can be measured. The MIC's can be measured by the procedure recommended by the International Collaborative Study on Antibiotic Sensitivity Testing (Ericcson and Sherris, *Acta. Pathologica et Microbiologia Scandinau*, Supp. 217, Section B: 64–68 (1971)), which employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2 fold dilutions of the test compound are employed, with initial concentration of the test drug being 200 mcg/ml Single colonies are disregarded when reading plates after 18 hrs. at 37° C. The susceptibility (MIC) of the test organism is accepted as the lowest concentration of compound capable of producing complete inhibition of growth as judged by the naked eye.

When using an antibacterial compound of this invention, or a salt thereof, in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, an antibacterial compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2,000 to 4,000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

As indicated earlier, the antibacterial compounds of this invention are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and the severity of the patient's symptoms. The antibacterial compounds of this invention will normally be used orally at dosages in the range from 20 to about 100 mg per kilogram of body weight per day, and parenterally at dosages from about 10 to about 100 mg per kilogram of body weight per day, usually in divided doses. In some instances it may be necessary to use doses outside these ranges.

The following examples and preparations are provided solely for further illustration. Nuclear magnetic resonance spectra (NMR) were measured for solutions in deuterated chloroform ($CDCl_3$) or deuterated dimethyl sulfoxide (DMSO-$d_6$), and peak positions are reported in parts per million downfield from tetramethylsilane. The following abbreviations for peak shapes are used: bs, broad singlet; s, singlet; d, doublet; t, triplet; q, quartet, m, multiplet.

EXAMPLE 1

Monobenzyl Esters of Dicarboxylic Acids

A trans-1,4-Cyclohexanedicarboxylic acid monobenzyl ester

To a solution of 1.0 g (2.8 mmole) dibenzyl trans-1,4-cyclohexanedicarboxylate in 20 ml tert.-butanol (warm) is added a solution of 1.9 g potassium hydroxide in 10 ml tert.-butanol. After stirring at room temperature overnight the cloudy mixture is evaporated to remove solvent, taken up in water and acidified to pH 5.3; then, after 30 minutes, acidified to pH 5.25 with dilute hydrochloric acid. The precipitated solid is collected on a filter, redissolved in dilute sodium bicarbonate solution and this readjusted to pH 5.25 to precipitate the purified monoester $^1$H-NMR (DMSO-$D_6$) ppm (delta): 1.1–2.3 (m, 10H), 5.1 (s, 1H), 7.35 (s, 5H).

B

Monobenzyl terephthalate

To a warm solution of 10 g dibenzyl terephthalate in 200 ml t-butanol is added a solution of 1.9 g potassium hydroxide in 100 ml t-butanol and 10 ml water. The resulting mixture is stirred at room temperature for 60 hours. The solvent is evaporated in vacuo, the residue taken up in water and acidified to pH 5.3 and worked up as in Part A, above, to provide the desired monoester in 56% yield, m.p. 178° C. $^1$H-NMR (DMSO) ppm (delta): 5.3 (s, 2H), 7.4 (s, 5H), 8.1 (s, 4H); infrared absorption peaks at 1690 cm$^{-1}$ and 1710 cm$^{-1}$.

Saponification of dibenzyl terephthalate (15 g) in benzyl alcohol (225 ml) containing an equimolar amount of potassium hydroxide by stirring overnight at room temperature and trituration with ethyl ether affords a 75% yield of the potassium salt of monobenzyl terephthalate.

C

Monobenzyl isophthalate

Dibenzyl isophthalate is converted to the monobenzyl ester, potassium salt in 75% yield by the above procedure employing benzyl alcohol as solvent. $^1$H-NMR (D$_2$O) ppm (delta): 5.1 (s, 2H), 7.2 (s, 5H), 7.6–7.8 (m, 3H), 8.4 (t, 1H).

D

The monobenzyl esters of the following dicarboxylic acids are obtained similarly by the above procedures.
1,2-cyclopropanedicarboxylic acid
1,3-cyclobutanedicarboxylic acid
trans-1,2-cyclobutanedicarboxylic acid
1,3-cyclopentanedicarboxylic acid
trans-1,3-cyclohexanedicarboxylic acid
1,4-cycloheptanedicarboxylic acid
1,3-cycloheptanedicarboxylic acid
1,4-naphthalenedicarboxylic acid
2,6-pyridinedicarboxylic acid
2,4-pyridinedicarboxylic acid
2,5-pyridinedicarboxylic acid
3,5-pyridinedicarboxylic acid
2,5-pyrazinedicarboxylic acid
2,5-furandicarboxylic acid
2,5-thiophenedicarboxylic acid
trans-1,2-cyclohexanedicarboxylic acid 1,12-dodecanedicarboxylic acid 1,10-decanedicarboxylic acid
n-butylmalonic acid
methylmalonic acid
ethylmalonic acid
isopropylmalonic acid
diethylmalonic acid
di-n-butylmalonic acid
3-methylglutaric acid
3-ethylglutaric acid
3-ethyl-3-methylglutaric acid
2-methylglutaric acid
2,2-dimethylglutaric acid
2-methylsuccinic acid
2-phenylsuccinic acid
3-methyladipic acid
3-n-butyladipic acid
3,3-di-n-propylglutaric acid
3,3-diisobutylglutaric acid
phenylmalonic acid
tricarballylic

EXAMPLE 2

Cis-1,2-cyclohexanedicarboxylic acid monobenzyl ester

To 15.4 g (0.10 mole) cis-1,2-cyclohexanedicarboxylic anhydride in 200 ml toluene is added dropwise a solution of 10.8 g (0.10 mole) benzyl alcohol in 50 ml of toluene. The mixture is stirred at room temperature for one hour then warmed to 60° C. and held at this temperature for one hour. The solvent is evaporated to a small volume and the product monoester obtained upon cooling and filtration of the precipitated solid.

Alternatively, the reaction mixture in toluene is treated with an equimolar amount of ethanolic potassium hydroxide to obtain the potassium salt of the monobenzyl ester. The sodium salt is obtained by use of methanolic sodium hydroxide in like manner.

The corresponding monobenzyl esters or their sodium or potassium salts are obtained from the following dicarboxylic acid anhydrides by the above procedure.
succinic anhydride
glutaric anhydride (refluxed in toluene overnight)
cis-1,2-cyclobutanecarboxylic anhydride
phthalic anhydride
1,2-naphthalenedicarboxylic anhydride
3,4-furandicarboxylic acid
2,3-pyridinedicarboxylic acid
2,3-pyrazinedicarboxylic acid

EXAMPLE 3

Benzyl 1,1-dioxopenicillanoyloxymethyl succinate

To a mixture of 9.2 g (0.044 mole) benzyl succinate half ester in 200 ml of chloroform and 25 ml water was added 40% aqueous tetrabutylammonium hydroxide with vigorous stirring until a pH of 8.5 was obtained. The chloroform layer was separated and the aqueous layer extract (1×100 ml) with chloroform. The combined chloroform extracts were dried (Na$_2$SO$_4$) and concentrated in vacuo to an oil. The oil was combined with 200 ml toluene and 16.5 g (0.044 mole) iodomethyl penicillanate 1,1-dioxide was added. The mixture was stirred 30 minutes, diluted to 400 ml with ethyl acetate and the precipitated tetrabutylammonium iodide removed by filtration. The filter cake was washed with 100 ml ethyl acetate and the combined filtrates were washed with saturated NaHCO$_3$ (1×100 ml), water (1×100 ml), brine (1×100 ml), dried (Na$_2$SO$_4$) and concentrated in vacuo to an oil. Chromatography on silica gel (1 kg), eluting with 1:1 (v/v) ethyl acetate/hexane), gave 8.5 g (43%) of a white solid.

$^1$H-NMR (CDCl$_3$) ppm (delta): 1.45 (s, 3H), 1.63 (s, 3H), 2.77 (s, 4H), 3.47 (d, 2H), 4.43 (s, 1H), 4.62 (t, 1H), 5.17 (s, 2H), 5.84 (AB quartet, 2H), 7.4 (s, 5H).

In the same manner the following compounds were also prepared from the appropriate monobenzyl ester:

a. Benzyl 1,1-dioxopenicillanoyloxymethyl glutarate—(61% yield)—$^1$H-NMR (CDCl$_3$) ppm (delta): 1.42 (s, 3H), 1.6 (s, 3H), 1.8–2.2 (m, 2H), 2.28–2.68 (m, 4H), 3.45 (d, 2H), 4.4 (s, 1H), 4.6 (t, 1H), 5.14 (s, 1H), 5.8 (AB quartet, 2H), 7.37 (s, 5H).

b. Benzyl 1,1-dioxopenicillanoyloxymethyl adipate—(47% yield)—$^1$H-NMR (CDCl$_3$) ppm (delta): 1.46 (s, 3H), 1.63 (s, 3H), 1.53–1.86 (m, 4H), 2.22–2.6 (m, 4H), 3.46 (d, 2H), 4.42 (s, 1H), 4.6 (t, 1H), 5.13 (s, 2H), 5.82 (AB quartet, 2H), 7.33 (s, 5H).

c. Benzyl 1,1-dioxopenicillanoyloxymethyl dimethylmalonate—(73.8% yield)—$^1$H-NMR (CDCl$_3$) ppm (delta): 1.4 (s, 3H), 1.53 (s, 9H), 3.45 (d, 2H), 4.4 (s, 1H), 4.56 (t, 1H), 5.22 (s, 2H), 5.78 (AB quartet, 2H), 7.35 (s, 5H).

d. Benzyl 1,1-dioxopenicillanoyloxymethyl malonate—(45% yield)—$^1$H-NMR (CDCl$_3$) ppm (delta): 1.43 (s, 3H), 1.6 (s, 3H), 3.46 (d, 2H), 3.53 (s, 2H), 4.42 (s, 1H), 4.6 (t, 1H), 5.2 (s, 2H), 5.85 (AB quartet, 2H), 7.39 (s, 5H); infrared spectrum (nujol) cm$^{-1}$: 1795, 1790.

e. Benzyl 1,1-dioxopenicillanoyloxymethyl sebacate—(54% yield), oil $^1$H-NMR (CDCl$_3$) ppm (delta): 1.2–1.9 (m, 18H), 2.1–2.5 (m, 4H), 3.4 (d, 2H), 4.4 (s, 1H), 4.6 (t, 1H), 5.1 (s, 2H), 5.8 (q, 2H), 7.3 (s, 5H).

f. In like manner the remaining monobenzyl esters provided in Examples 1 and 2 are converted to the corresponding compounds of the formula

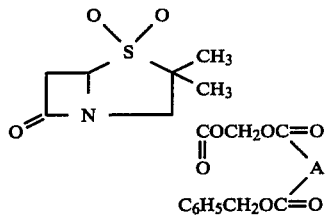

where A is as defined for the starting monobenzyl ester.

g. Alternatively, the above benzyl, 1,1-dioxopenicillanoyloxymethyl diesters are prepared as described below for the adipate diester.

A mixture of 17.0 g (0.0665 mole) sodium 1,1-dioxopenicillanate, 18.0 g (0.0634 mole) benzyl chloromethyl adipate, 6.7 g (0.020 mole) tetrabutylammonium bromide and 300 ml acetone is heated under nitrogen at reflux overnight. The acetone is evaporated and the residual gel taken up in 300 ml ethyl acetate. Water (150 ml) is added, the organic layer is separated and the aqueous layer extracted with fresh ethyl acetate (150 ml). The combined organic extracts are washed with water (3×250 ml), brine (2×150 ml), dried (Na$_2$SO$_4$) and concentrated in vacuo to an oil (31.8 g). The oil is chromatographed on 700 g silica gel, eluting with 2:1 hexane/ethyl acetate to remove the less polar impurities, then with 1:1 ethyl acetate/hexane to remove the product. Evaporation of solvent from the product fractions affords 27.3 g (89.5%).

By employing the corresponding methyl half ester, or other alkyl half ester where alkyl is ethyl, n-propyl, isopropyl, n-butyl, or isobutyl, in place of the benzyl half ester in the above procedure the corresponding alkyl 1,1-dioxopenicillanyloyloxymethyl dicarboxylate is provided in like manner.

EXAMPLE 4

Sodium 1,1-Dioxopenicillanoyloxymethyl Succinate

A solution of 8.4 g (0.019 mole) of benzyl 1,1-dioxopenicillanoyloxymethyl succinate in 75 ml of tetrahydrofuran was added to a suspension of 4 g of 10% (w/w) palladium on carbon in tetrahydrofuran (THF) and shaken under 50 psi (3.52 kg/cm$^2$) of hydrogen on an hydrogenation apparatus. After 30 minutes the catalyst was removed by filtration through a filter aid and the cake washed with 75 ml of THF, the combined filtrates were concentrated in vacuo and taken up in 75 ml of ethyl acetate. To this solution was added 3.07 g (0.019 mole) of sodium-2-ethylhexanoate with stirring. After 15 minutes the precipitate was filtered, washed with diethyl ether and dried under nitrogen to give 6.8 g (95%) of a white solid.

The following sodium salts were prepared in like manner, except that in cases where no precipitate forms upon addition of sodium 2-ethylhexanoate, ethyl ether is added to effect precipitation.

a. Sodium 1,1-dioxopenicillanoyloxymethyl glutarate—(93% yield)—$^1$H-NMR (D$_2$O) ppm (delta): 1.48 (s, 3H), 1.63 (s, 3H), 1.6–2.7 (m, 6H), 3.22–3.98 (m, 2H), 4.68 (s, 1H), 4.8–5.13 (m, 1H), 5.86 (AB quartet, 2H).

b. Sodium 1,1-dioxopenicillanoyloxymethyl adipate—(79% yield)—$^1$H-NMR (D$_2$O) ppm (delta): 1.46 (s, 3H), 1.63 (s, 3H), 1.44–1.8 (m, 4H), 2.1–2.6 (m, 4H), 3.1–3.96 (m, 2H), 4.56–4.76 (HOD peak, hides C-3H), 5.0–5.16 (m, 1H), 5.92 (AB quartet, 2H).

c. Sodium 1,1-dioxopenicillanoyloxymethyl dimethylmalonate—(94.5% yield)*—$^1$H-NMR (D$_2$O) ppm delta: 1.33 (s, 6H), 1.44 (s, 3H), 1.58 (s, 3H), 3.16–3.9 (m, 2H), 4.65 (s, 1H), 4.93–5.1 (m, 1H), 5.93 (AB quartet, 2H); infrared spectrum (nujol), 1780 cm$^{-1}$.

*Recrystallization from ethyl acetate/hexane affords crystalline needles.

d. Sodium, 1,1-dioxopenicillanoyloxymethyl malonate—(88% yield)—$^1$H-NMR (D$_2$O) ppm (delta): 1.45 (s, 3H), 1.6 (s, 3H), 3.2–3.93 (m, 2H), 4.66 (s, 1H), 4.96–5.13 (m, 1H), 5.88 (AB quartet, 2H). It was noted that the CH$_2$-malonate hydrogen atoms exchanged with D$_2$O.

e. Sodium 1,1-dioxopenicillanoyloxymethyl sebacate—(80% yield)—$^1$H-NMR (D$_2$O) ppm (delta): 1.2–1.7 (m, 18H), 2.15 (t, 1H), 2.45 (t, 2H), 3.45 (d, 1H), 3.65–3.75 (dd, 1H), 4.75 (s, 1H), 5.15–5.25 (m, 1H), 5.8–6.0 (dd, 2H); infrared spectrum (KBr) cm$^{-1}$: 1570, 1770, 1800.

f. The remaining benzyl esters provided in Example 3 are hydrogenated and converted to the corresponding sodium salt by the above procedure. The corresponding potassium salt is obtained by use of potassium 2-ethyl hexanoate in the above procedure.

EXAMPLE 4A

Crystalline 1,1-dioxopenicillanoyloxymethyl Adipic Acid Hydrate

To 400 ml acetone is added 48.5 g (0.19 mole) sodium 1,1-dioxopenicillanate, 48.0 g (0.17 mole) benzyl chloromethyl adipate and 19.3 g (0.06 mole) tetrabutylammonium bromide. The mixture is heated at reflux under nitrogen overnight, filtered, washed with acetone and the filtrate evaporated. The residue is taken up in 500 ml ethyl acetate, washed alternately with brine and water, 250 ml portions, brine again and dried (MgSO$_4$). Evaporation of solvent in vacuo afforded 89.6 g light yellow oil. The oil is taken up in 250 ml ethyl acetate, 20.0 g 10% Pd/C added and the mixture is hydrogenated at 3.52 kg/cm$^2$ for one hour. After adding 15 g of fresh catalyst the hydrogenation is continued for 2.5 hours. The catalyst is removed by filtration, the cake washed with acetone (1500 ml) and the combined filtrate and washings evaporated in vacuo to obtain a viscous oil. The oil is taken up in 150 ml acetone and water added slowly to start crystallization, then continued until 800 ml water is added. After stirring 30 minutes, the crystalline product is recovered by filtration, washing with water and air dried to obtain 58.2 g of the title carboxylic acid. Recrystallization from ethyl acetate affords the crystalline monohydrate, m.p. 100°–102° C.

Analysis: Calculated for C$_{15}$H$_{21}$O$_9$NS.H$_2$O: C,44.00; H, 5.66; N, 3.42. Found: C, 43.93; H, 5.65; N, 3.42.

The crystallinity was verified by X-ray crystallography.

EXAMPLE 5

Sodium 1,1-Dioxopenicillanoyloxymethyl trans-1,4-cyclohexanedicarboxylate

A

Benzyl chloromethyl trans-1,4-cyclohexanedicarboxylate

To a mixture of 3.06 g (0.036 mole) sodium bicarbonate, 5.46 g (0.018 mole) potassium benzyl trans-1,4-cyclohexanedicarboxylate, 50 ml water and 500 ml chloroform is added 6.17 g (0.018 mole) tetrabutylammonium hydrogen sulfate and the mixture is stirred at room temperature overnight. The layers are separated. The aqueous layer is extracted twice with chloroform and the combined chloroform layers are dried and evaporated to dryness. The resulting tetrabutylammonium salt is taken up in methylene chloride (20 ml) and the solution added dropwise to 20 ml of bromochloromethane at 0° C. The resulting mixture is stirred at ambient temperature for 70 hours, the solvent evaporated and ethyl acetate added to the residue. The precipitated tetrabutylammonium bromide is removed by filtration, the filtrate dried ($Na_2SO_4$) and evaporated in vacuo to obtain 5 g (91%) of crude product. Purification by silica gel chromatography, eluting with 1:3 ethyl ether/hexane gave 1.9 g (35%) of the desired product as an oil. $^1$H-NMR (CDCl$_3$) ppm (delta): 1.0–2.4 (m, 10H), 5.1 (s, 2H), 5.7 (s, 2H), 7.3 (s, 5H).

B

Benzyl 1,1-dioxopenicillanoyloxymethyl trans-1,4-cyclohexanedicarboxylate

A solution of 4.2 g (13.5 mmole) benzyl chloromethyl trans-1,4-cyclohexanedicarboxylate, 3.63 g (14.2 mmole) sodium 1,1-dioxopenicillanate, 1.45 g (4.5 mmole) and 100 ml acetone is heated at reflux overnight. The acetone is evaporated, ethyl acetate (100 ml) added and the solution washed with water (3 times), brine and dried over anhydrous sodium sulfate. The solvent is removed by evaporation in vacuo to afford a crude product which is purified by column chromatography on silica gel, eluting with 1:1 ethyl acetate/hexane to provide 5.3 g (78%) of purified product as an oil which is used in the next step. $^1$H-NMR (CDCl$_3$) ppm (delta): 1.3–1.65 (m, 6H), 1.65–2.6 (m, 10H), 3.4 (d, 2H), 4.4 (s, 1H), 4.55 (t, 1H), 5.1 (s, 2H), 5.8 (q, 2H), 7.3 (s, 5H); infrared spectrum (CHCl$_3$) cm$^{-1}$: 1730, 1760, 1810.

C

To a solution of 2.5 g (4.9 mmole) of the benzyl ester provided in Part B, above, in 50 ml ethyl acetate under a nitrogen atmosphere, is added 1.5 g 10% Pd/C catalyst. The resulting mixture is hydrogenated at 1–2 atmospheres pressure for about 20 minutes. The catalyst is removed by filtration and 0.82 g (4.9 mmole) sodium 2-ethylhexanoate is added to the filtrate. After stirring for 30 minutes at room temperature the mixture is concentrated to one-third volume and three volumes of ethyl ether is added. The precipitated title compound is filtered, washed with ether and dried under nitrogen to afford 1.7 g (79% step yield). $^1$H-NMR (D$_2$O) ppm (delta): 1.3–2.4 (m, 16H), 3.4–3.6 (m, 2H), 4.6 (s, 1H), 4.9–5.0 (m, 1H), 5.7 (q, 2H); infrared spectrum (KBr) cm$^{-1}$: 1565, 1760, 1810, 1780.

EXAMPLE 6

Crystalline 1,1-Dioxopenicillanoyloxymethyl trans-1,4-Cyclohexanecarboxylic Acid To a solution of 6.07 g (12 mmole) benzyl 1,1-dioxopenicillanoyloxymethyl trans-1,4-cyclohexanedicarboxylate in 100 ml ethyl acetate under nitrogen is added 3.2 g, 10% Pd/C catalyst. The mixture is hydrogenated for 45 minutes with shaking at 50 psi (3.52 kg/cm$^2$). The mixture is filtered, the filtrate concentrated in vacuo to afford a residual oil which crystallizes upon standing. The product is recrystallized from ethyl acetate/hexane under a nitrogen atmosphere to obtain 2.35 g of crystalline product which appeared to contain some oil. This was taken up in ethyl acetate (100 ml) and an equivalent amount of sodium 2-ethylhexanoate is added. The precipitated sodium salt is stirred for 45 minutes, concentrated to one-third volume and ethyl ether added to complete the precipitation. The sodium salt is collected by filtration, washed with ether and dried under nitrogen. The sodium salt is taken up in water (50 ml) acidified with hydrochloric acid and the mixture extracted with ethyl acetate. The extracts are dried (Na$_2$SO$_4$), the solvent evaporated in vacuo, the residue crystallized from ethyl acetate/hexane and dried under nitrogen to obtain 1.85 g (37%) of product, m.p. 118.5°–119° C. which is found to be crystalline by X-ray diffraction. $^1$H-NMR (CDCl$_3$) ppm (delta: 1.4 (s, 3H, 1.4–1.55 (m, 4H), 1.6 (s, 3H), 2.05–2.15 (m, 4H), 2.25–2.45 (m, 2H), 3.4–3.6 (m, 2H), 4.4 (s, 1H), 4.6–4.65 (m, 1H), 5.7–5.95 (dd, 2H); infrared specturm (KBr) cm$^{-1}$: 1700, 1760, 1780, 1800.

EXAMPLE 7

1,1-Dioxopenicillanoyloxymethyl Terephthalate and its Sodium Salt

A

Benzyl chloromethyl terephthalate

To a solution of 18.53 g. (0.062 mole) potassium benzyl terephthalate in 300 ml water is added 600 ml chloroform, 10.38 g (0.121 mole) sodium bicarbonate and 20.95 g (0.062 mole) tetrabutylammonium hydrogen sulfate. The resulting mixture is stirred at room temperature for three hours, the organic layer is separated and the aqueous phase extracted twice with chloroform. The organic layers are combined, dried (Na$_2$SO$_4$) and the solvent evaporated to provide the tetrabutylammonium salt of benzyl terephthalate. This is taken up in 25 ml methylene chloride and the solution added dropwise to 100 ml bromochloromethane at 0° C. The resulting mixture is allowed to warm to room temperature, stirred overnight and the product isolated and purified by the methods described in Example 5, Part A to obtain the title diester, as crystals, m.p. 64°–66° C. $^1$H-NMR (CDCl$_3$) ppm (delta): 5.3 (s, 2H), 5.9 (s, 2H), 7.3 (s, 5H), 8.1 (s, 4H); infrared spectrum (KBr) cm$^{-1}$: 1720 and 1735.

B

Benzyl 1,1-dioxopenicillanoyloxymethyl terephthalate

A solution of 6.34 g (0.021 mole) benzyl chloromethyl terephthalate, 5.58 g (0.022 mole) sodium 1,1-dioxopenicillanate, 2.24 g (0.0069 mole) tetrabutylammonium bromide and 200 ml acetone is stirred at reflux under a nitrogen atmosphere for 18 hours. The acetone is then evaporated, the residue taken up in ethyl acetate, washed with water three times and dried (Na$_2$SO$_4$). Evaporation of solvent affords 11 g of crude product which is purified by passing through an 20×2 cm column of silica gel eluting with ethyl acetate/hexane, 1:1. Evaporation of product fractions gave 10 g (96%) of the desired benzyl ester as an oil. $^1$H-NMR (CDCl$_3$) ppm (delta): 1.4 (s, 3H), 1.5 (s, 3H), 3.4 (d, 2H), 4.4 (s, 1H), 4.6 (t, 1H), 5.4 (s, 2H), 6.1 (q, 2H), 7.4 (s, 5H), 8.1 (s, 4H); infrared spectrum (CHCl$_3$) cm$^{-1}$: 1725, 1745, 1780, 1810.

C

A solution of 9 g of the benzyl ester obtained in Part B in 50 ml ethyl acetate is evacuated to remove air and placed under a nitrogen atmosphere. To this is added 2.5 g 10% palladium-on-carbon catalyst and the mixture hydrogenated at 3 atmospheres for 20 minutes. The mixture is filtered through a filter aid, washing with ethyl acetate. To the filtrate and washings is added 2.98 g sodium 2-ethylhexanoate and the resulting mixture stirred for 30 minutes. An additional 50 ml each of ethyl acetate and ethyl ether are added to the resulting thick mixture and this is filtered, washing with ethyl ether. After drying overnight, 5.8 g (75%) of crystalline sodium salt is obtained.

D

To a solution of one gram of the above sodium salt in 50 ml water is added 5 ml of normal hydrochloric acid and the resulting mixture is extracted with 75 ml ethyl acetate. The ethyl acetate is concentrated in vacuo to obtain a slurry and sufficient ethyl acetate added to just dissolve the precipitate. This solution is stirred while slowly adding hexane at room temperature to the cloud point. This is then warmed on the steambath to effect solution, and a few drops of hexane added, the mixture cooled to room temperature and placed in the refrigerator. The resulting crystals are collected by filtration and dried under nitrogen to obtain 900 mg (95%) of the title acid, m.p. 167°–169° (dec). $^1$H-NMR (DMSO) ppm (delta): 1.4 (s, 3H), 1.5 (s, 3H), 3.4 (d, 2H), 4.6 (s, 1H), 5.1–5.3 (m, 2H), 6.1 (q, 2H), 8.1 (s, 4H); infrared spectrum (KBr) cm$^{-1}$: 1700, 1750, 1780, 1810.

EXAMPLE 8

Sodium 1,1-Dioxopenicillanoyloxymethyl isophthalate

A

Benzyl chloromethyl isophthalate

By the procedure of Example 7, Part A 17.0 g (0.058 mole) potassium benzyl isophthalate in 45 ml water and 500 ml chloroform is converted to its tetrabutylammonium salt and this reacted with excess bromochloromethane. The resulting crude product, 15 g, is taken up in ethyl acetate, this added to 45 g silica gel, the mixture slurried and the solvent evaporated. The residual silica gel was dry-loaded on an 8 inch column of silica gel and eluted with ethyl ether/hexane 1:3. Evaporation of solvent from the product containing fractions gives the desired diester as an oil. $^1$H-NMR (CDCl$_3$) ppm (delta) 5.3 (s, 2H), 5.9 (s, 2H), 7.3 (s, 5H), 8.0–8.3 (m, 3H), 8.55 (t, 1H).

B

Benzyl 1,1-dioxopenicillanoyloxymethyl isophthalate

A mixture of 12.22 g (0.04 mole) benzyl chloromethyl isophthalate, 10.75 g (0.042 mole) sodium 1,1-dioxopenicillanate, 4.31 g (0.0134 mole) tetrabutylammonium bromide and 400 m acetone are heated at reflux for 30 hours. The acetone was evaporated and replaced by ethyl acetate. The solution was washed with water (3x), brine (1x) and dried (Na$_2$SO$_4$). Evaporation of solvent and silica gel chromatography of the residue, eluting with ethyl ether/hexane (65:35) affords a 41% yield of product as an oil which crystallizes upon standing. $^1$H-NMR (CDCl$_3$) ppm (delta): 1.3 (s, 3H), 1.5 (s, 3H), 3.4 (d, 2H), 4.5 (s, 1H), 4.6 (t, 1H), 5.3 (s, 2H), 6.0 (q, 2H), 7.4 (s, 5H), 7.5–7.7 (m, 1H), 8.1–8.4 (m, 2H), 8.7–8.8 (m, 1H); infrared spectrum (KBr) cm$^{-1}$: 1720, 1750, 1805.

C

A mixture of 8.14 g (0.016 mole) of the benzyl ester obtained in Part B, 2.5 g 10% Pd/C catalyst and 50 ml ethyl acetate is hydrogenated by the procedure of Example 7, Part C. The mixture is filtered to remove catalyst and 2.70 g (0.016 mole) sodium 2-ethylhexanoate is added. After stirring for 20 minutes, the thick slurry is concentrated to one third its volume and ethyl ether added to complete the precipitation. The resulting crystals are collected by filtration and dried under nitrogen to obtain 6.33 g (90%) of the title sodium salt. $^1$H-NMR (DMSO) ppm (delta): 1.3 (s, 3H), 1.5 (s, 3H), 3.3–3.4 (m, 1H), 3.5–3.6 (m, 1H), 4.55 (s, 1H), 5.0–5.2 (m, 1H), 6.05 (q, 2H), 7.45 (t, 1H), 7.8–8.3 (m, 2H), 8.5 (bs, 1H); infrared spectrum (KBr) cm$^{-1}$: 1575, 1620, 1740, 1810.

EXAMPLE 9

A

Benzyl 1-Chloroethyl-trans-1,4-cyclohexanedicarboxylate

To 30.0 g (0.10 mole) potassium benzyl trans-1,4-cyclohexanedicarboxylate, 16.8 g (0.20 mole) sodium bicarbonate, 300 ml water and 2.5 liters chloroform is added 33.9 g (0.10 mole) tetrabutylammonium hydrogen sulfate. The mixture is stirred overnight, the layers separated and the aqueous layer extracted with chloroform. The combined organic layers are evaporated to dryness and the residue taken up in 150 ml methylene chloride. The resulting solution is added dropwise to 100 ml 1-bromo-1-chloroethane at 0° C. and the reaction mixture stirred at 25° C. for 48 hours. The solvent is evaporated, the residue is triturated with ethyl acetate, filtered to remove tetrabutylammonium bromide and the filtrate dried (Na$_2$SO$_4$). Evaporation of solvent affords the title compound.

B

In like manner reaction of the appropriate potassium salt, benzyl ester and 1-bromo-1-chloroalkane by the above method provides compounds of the formula below

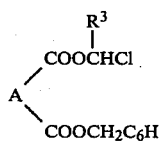

where A and R³ are as follows:

| A | R³ |
|---|---|
| CH₂ | CH₃ |
| C(CH₃)₂ | CH₃ |
| (CH₂)₂ | CH(CH₃)₂ |
| CH₃CH | CH₃CH₂ |
| (CH₂)₄ | CH₃CH₂CH₂ |
| (CH₂)₅ | CH₃ |
| (CH₂)₈ | CH₃CH₂ |
| (CH₃CH₂)₂C | CH(CH₃)₂ |
| 1,2-C₆H₄ | CH₃ |
| 1,3-C₆H₄ | CH₃ |
| 1,4-C₆H₄ | CH₃CH₂ |

EXAMPLE 10

Employing the benzyl esters provided in the preceding Example as starting materials, the indicated products of formula (V, R¹ is benzyl) are obtained and converted to the corresponding salts (V, R¹ is Na or K) by the procedures of Example 7.

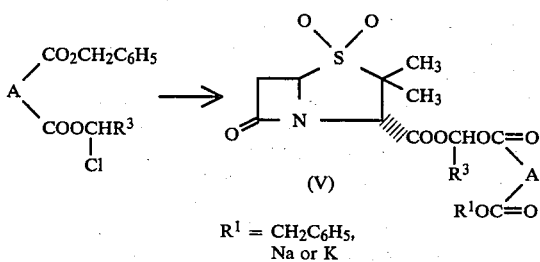

R¹ = CH₂C₆H₅, Na or K

EXAMPLE 11

Tetrabutylammonium 6-[D-(2-[1-methyl-2-methoxycarbonylvinylamino]-2-phenylacetamido)]penicillanate To 300 ml chloroform is added 39.3 g 6-[D-(2-amino-2-phenylacetamido)]penicillanic acid trihydrate, 50 ml of water is added and the pH of the mixture adjusted to 8.5 by addition of 40% aqueous tetrabutylammonium hydroxide. The layers are separated, the aqueous layer is saturated with sodium sulfate and extracted with fresh chloroform. The extracts and initial lower layer are combined and the solvent is evaporated to about 250 ml total volume.

To this is added 150 ml methyl acetoacetate and 30 g of anhydrous magnesium sulfate. The mixture is heated at reflux for three hours, the mixture allowed to settle and the warm organic layer decanted. The clear chloroform solution is allowed to cool to obtain crystals of the title compound in 52% yield, m.p. 182°–184° C. (decomp.). ¹H-NMR (CDCl₃) ppm (delta): 0.8–2.0 (m, 4H), 1.88 (s, 3H), 3.1–3.6 (m, 8H), 3.6 (s, 3H), 4.17 (s, 1H), 4.58 (s, 1H), 5.05 (d, 1H), 5.38–5.6 (m, 2H), 6.78 (d, 1H), 7.35 (s, 5H), 9.4 (d, 1H).

EXAMPLE 12

Tetrabutylammonium 6-[D-(2-[1-methyl-2-methoxycarbonylvinylamino]-2-[4-hydroxyphenyl]acetamido)]penicillanate To 300 ml of dichloromethane was added 41.9 g of 6-(2-amino-2-[4-hydroxyphenyl]acetamido)penicillanic acid trihydrate and 50 ml of water, and then the pH was adjusted to 8.5 using 40% aqueous tetrabutylammonium hydroxide. Three layers were obtained. The upper layer was removed, saturated with sodium sulfate and then it was extracted with dichloromethane. The extracts were combined with the middle layer and the lower layer, and the resulting mixture was evaporated in vacuo to give an oil which crystallized on trituration with acetone. This aforded 44.6 g of tetrabutylammonium 6-(2-amino-2-[4-hydroxyphenyl]acetamido)penicillanate.

The above salt was added to 150 ml of methyl acetoacetate and the suspension was heated at ca. 65° C. until a clear solution was obtained (8 minutes). The mixture was allowed to cool, and then the solid was recovered by filtration. The solid was washed with methyl acetoacetate, followed by diethyl ether, to give 49.25 g of tetrabutylammonium 6-(2-[1-methyl-2-methoxycarbonylvinylamino]-2-[4-hydroxyphenyl]-acetamido)-penicillanate crystals.

EXAMPLE 13

A

Chloromethyl 6-[D-(2-[1-methyl-2-methoxycarbonylvinylamino]-2-phenylacetamido)]penicillanate To 42.9 g (0.062 Mole) tetrabutylammonium 6-[D-(2-[1-methyl-2-methoxycarbonylvinylamino]-2-phenylacetamido)]penicillanate is added 500 ml chloroiodomethane and the mixture stirred for one hour at room temperature. The mixture is concentrated, chromatographed on 1 kg silica gel, eluting with 80:20 by volume ethyl acetate/hexane, collecting 75 ml fractions. Fractions 5–13 are combined and evaporated to dryness to afford a yellow oil. This was re-chromatographed, eluting with a 1:1 by volume mixture of the same solvents to afford 30.6 g (80%) of the desired chloromethyl ester as a foam. ¹H-NMR (CDCl₃) ppm (delta): 1.5 (s, 3H), 1.57 (s, 3H), 1.9 (s, 3H), 3.65 (s, 3H), 4.4 (s, 1H), 4.65 (s, 1H), 5.12 (d, 1H), 5.42–5.7 (m, 2H), 5.75 (double d, 2H), 6.8 (d, 1H), 7.4 (s, 5H), 9.35 (d, 1H).

B

Iodomethyl 6-[D-(2-[1-methyl-2-methoxycarbonylvinylamino]-2-phenylacetamido)]penicillanate The above chloromethyl ester, 4.96 g (10 mmole) and 7.5 g (50 mmole) sodium iodide are combined with 50 ml acetone and stirred overnight. The mixture is concentrated to dryness, the residue taken up in ethyl acetate (150 ml), washed with 3×50 ml water, 1×50 ml brine, dried (Na₂SO₄) and concentrated to afford 6.0 g of product as a pale yellow foam. Trituration with petroleum ether afforded a pale yellow solid, 5.2 g (89%).

C

Starting with tetrabutylammonium 6-[D-(2-[1-methyl-2-methoxycarbonylvinylamino]-2-[4-hydroxyphenyl]acetamido)]penicillanate in the above procedures, but using dimethylformamide as cosolvent in Part A, affords the iodomethyl ester of amoxicillin enamine.

EXAMPLE 14

6-[D-(2-Amino-2-phenylacetamido)]penicillanoyloxymethyl trans-1,4-cyclohexanedicarboxylic Acid Hydrochloride

A

Benzyl 6-[D-(2-[1-methyl-2-methoxycarbonylvinylamino]-2-phenylacetamido)]penicllanoyloxymethyl trans-1,4-cyclohexanedicarboxylate A solution of 2.22 g (3.28 mmole) tetrabutylammonium 6-[D-(2-[1-methyl-2-methoxycarbonylvinylamino]-2-phenylacetamido)]penicillanate and 1.00 g (3.23 mmole) benzyl chloromethyl trans-1,4-cyclohexanedicarboxylate in 100 ml acetone is stirred at room temperature overnight. The acetone is evaporated and replaced with ethyl acetate. The solution is washed with water, dried (Na2SO4) and the solvent evaporated in vacuo. The resulting crude material is purified by chromatography on silica gel, eluting with 40:60 ethyl acetate/hexane to afford 1.5 g (53%).

B

The benzyl ester obtained in Part A, above, 1.5 g (2.08 mmole) is dissolved in 25 ml acetone and 20.1 ml 0.1N hydrochloric acid is added. The mixture is stirred ten minutes, an additional 2.0 ml 0.1N hydrochloric acid is added and the solvent is evaporated. To the residue is added 75 ml water, the resulting mixture is extracted twice with ethyl ether containing a small amount of ethyl acetate. To the extracts is added 0.75 g 10% Pd/C catalyst and the mixture is shaken under hydrogen at 50 psi (3.52 kg/cm$^2$) for 30 minutes. The catalyst is removed by filtration and the filtrate is freeze dried to obtain 700 mg product. Infrared spectrum (KBr) cm$^{-1}$: 1680, 1700, 1750, 1800. $^1$H-NMR (DMSO) ppm (delta): 1.25 (s, 3H), 1.45 (s, 3H), 1.8–2.0 (m, 4H), 2.05–2.4 (m, 4H), 3.25–3.55 (m, 2H), 4.35 (s, 1H), 5.07 (bs, 1H), 5.35–5.45 (m, 1H), 5.55 (q, 1H), 5.65–5.85 (dd, 2H), 7.3–7.6 (m, 5H), 8.9 (bs, 1H), 9.45 (d, 3H).

EXAMPLE 15

6-[D-(2-Amino-2-[4-hydroxphenyl]acetamido)]-penicillanoyloxymethyl trans-1,4-cyclohexanedicarboxylic Acid Hydrochloride

A

Benzyl 6-[D-(2-[1-methyl-2-methoxycarbonylvinylamino]-2-[4-hydroxyphenyl]acetamido)]penicillanoyloxymethyl trans-1,4-cyclohexanedicarboxylate A solution of 0.5 g (1.61 mmole) benzyl chloromethyl trans-1,4-cyclohexanedicarboxylate and 1.14 g (1.61 mmole) tetrabutylammonium 6-[D-(2-[1-methyl-2-methoxycarbonylvinylamino]-2-[4-hydroxyphenyl]acetamido)]penicillanate in 50 ml dimethylformamide is stirred overnight at room temperature. The reaction mixture is diluted with ethyl acetate, washed three times with water, then with brine and dried (Na2SO4). The solvent is evaporated in vacuo. To the residue is added fresh ethyl acetate, the mixture washed again with water, brine and dried and evaporated to remove the last of the dimethylformamide. The residue is purified by silica gel chromatography, eluting with 7:3 ethyl acetate/hexane to yield 500 mg (42%) of purified diester.

B

To a solution of 0.5 g (0.678 mmole) of the purified diester obtained in Part A, above, in 25 ml acetone is added 6.8 ml 0.1N hydrochloric acid. After stirring for 10 minutes an additional 1.0 ml of 0.1N hydrochloric acid is added and the acetone is evaporated in vacuo. The residue is partitioned between water and ethyl ether and the aqueous layer washed with ether. To the aqueous phase is added 0.35 g, 10% Pd/C catalyst, under a nitrogen atmosphere, and the resulting mixture is hydrogenated at 50 psi (3.52 kg/cm$^2$) overnight. The mixture is filtered to remove catalyst and the aqueous filtrate is freeze dried to provide 200 mg (50%) of the title compound. $^1$H-NMR (DMSO-D$_6$) ppm (delta): 1.1–2.7 (m, 16H), 3.4–4.0 (bs, 1H), 4.3–4.5 (m, 1H), 5.0–5.2 (m, 1H), 5.4–6.0 (m 3H), 6.7–7.6 (dd, 4H); infrared spectrum (KBr) cm$^{-1}$: 1700, 1770, 3000, 3500.

In like manner the analogous compounds of the formula below are obtained by employing the appropriate starting materials in the above procedure. The corresponding tetrabutylammonium enamines are also obtained by the methods of Examples 11 and 12.

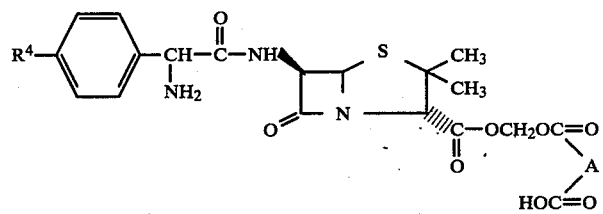

| R$^4$ | A |
|---|---|
| H | CH$_2$ |
| H | (CH$_2$)$_3$ |
| H | C(CH$_3$)$_2$ |
| OH | (CH$_2$)$_4$ |
| OCOCH(CH$_3$)$_2$ | 1,4-cycloheptyl |
| OCOOC$_6$H$_5$ | 1,2-phenylene |

-continued

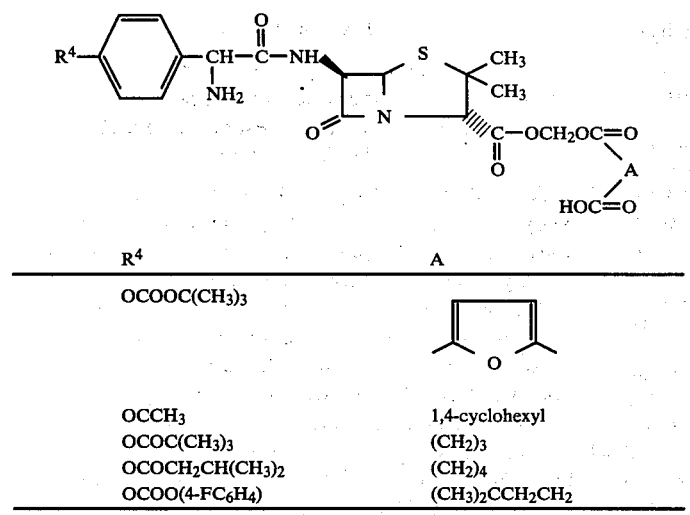

| R⁴ | A |
|---|---|
| OCOOC(CH₃)₃ | |
| | 1,4-cyclohexyl |
| OCCH₃ | |
| OCOC(CH₃)₃ | (CH₂)₃ |
| OCOCH₂CH(CH₃)₂ | (CH₂)₄ |
| OCOO(4-FC₆H₄) | (CH₃)₂CCH₂CH₂ |

EXAMPLE 16

Sodium 6-(2-phenoxyacetamido)penicillanoyloxymethyl Dimethylmalonate

A

Benzyl 6-(2-phenoxyacetamido)penicillanoyloxymethyl dimethylmalonate

To 50 ml of dimethylformamide is added 3.88 g (0.01 mole) potassium 6-(2-phenoxyacetamido)penicillanate, 2.7 g (0.01 mole) benzyl chloromethyl dimethylmalonate and the mixture stirred at room temperature for three hours. The mixture is poured into 150 ml ethyl acetate, washed with 3×50 ml water, 1×50 ml brine, dried (Na₂SO₄) and evaporated to dryness in vacuo. The residue is taken up in a small amount of ethyl acetate and transferred to a column of silica gel (200 g). The column was eluted with 1:1 ethyl acetate/hexane. The product fractions are combined and concentrated in vacuo to yield 2.0 g of product as a colorless oil. ¹H-NMR (CDCl₃) ppm (delta): 1.42 (s, 9H), 1.5 (s, 3H), 4.4 (s, 1H), 4.5 (s, 2H), 5.13 (s, 2H), 5.4–5.86 (m, 4H), 6.8–7.5 (m, 5H), 7.3 (s, 5H).

B

A mixture of 2.0 g (3.4 mmole) of the product of Part A, above, 40 ml ethyl acetate and 2.0 g 10% palladium-on-carbon catalyst is agitated under a hydrogen atmosphere at 50 psi for 45 minutes. An additional gram of catalyst is added and stirring continued for 30 minutes. The mixture is filtered, washing the cake with ethyl acetate. The filtrate and washings are stirred while adding 0.56 g (3.37 mmole) sodium 2-ethyl-hexanoate. Stirring is continued while adding an equal volume of ethyl ether. The precipitated solids are granulated by stirring for 30 minutes, filtered, washed with ether and dried under a nitrogen atmosphere to afford 1.35 g (77%) of the title sodium salt. ¹H-NMR (D₂O) ppm (delta): 1.33 (s, 9H), 1.4 (s, 3H), 4.4–4.6 (s (on top of broad singlet), 3H), 5.5 (bs, 2H), 5.8 (dd, 2H), 6.63–7.33 (m, 5H).

EXAMPLE 17

Sodium 6-(2-phenoxyacetamido)penicillanoxyloxymethyl Glutarate

A

Benzyl 6-(2-phenoxyacetamido)penicillanoyloxymethyl glutarate

To 50 ml dimethylformamide is added 3.88 g (0.01 mole) potassium 6-(2-phenoxyacetamido)penicillanate, 2.7 g (0.01 mole) benzyl chloromethyl glutarate and the mixture stirred for three hours after which 3.0 g (0.02 mole) sodium iodide is added and stirring continued overnight. The reaction mixture is quenched by addition of 150 ml ethyl acetate, washed with water (3×50 ml), brine (1×50 ml) and dried (Na₂SO₄). Evaporation of solvent in vacuo affords 6.0 g of oil which is purified by column chromatography on silica gel (300 g) with ethyl acetate/hexane solvent, 1:1. Concentration of the product fractions affords 5.0 g (85%) of colorless oil. ¹H-NMR (CDCl₃) ppm (delta): 1.45 (s, 3H), 1.55 (s, 3H), 1.73–2.16 (m, 2H), 2.16–2.6 (m, 4H), 4.4 (s, 1H), 4.5 (s, 2H), 5.05 (s, 2H), 5.4–5.83 (m, 2H), 5.73 (s, 2H), 6.66–7.4 (m. 5H), 7.28 (s, 5H).

B

The product obtained in Part A, 5.0 g (0.0085 mole), 50 ml ethyl acetate and 5 g 10% Pd/c catalyst are hydrogenated at 3 atmospheres pressure for one hour. An additional 2.5 catalyst is added and hydrogenation continued for two hours. The mixture is filtered through diatomaceous earth, washing with ethyl acetate. The combined filtrate and washings, 200 ml, are poured into a clean flask and 6.13 ml sodium 2-ethylhexanoate in ethyl acetate (0.23 g/ml) is added. After stirring for 30 minutes, the mixture is diluted with an equal volume of ethyl ether and filtered to obtain 2.25 g (51%) of sodium salt. ¹H-NMR (D₂O) ppm (delta): 1.4 (s, 3H), 1.43 (s, 3H), 1.4–2.5 (m, 6H), 4.4–4.8 (HOD), 5.46 (bs, 2H), 5.73 (bs, 2H), 6.64–7.4 (m, 5H).

EXAMPLE 18

Sodium 6-(2,6-dimethoxybenzamido)penicillanoyloxymethyl Dimethylmalonate

A mixture of 4.02 g (0.01 mole) sodium 6-(2,6-dimethoxybenzamido)penicillanate, 3.3 g (0.01 mole) benzyl chloromethyl dimethylmalonate and 30 ml dimethylformamide are stirred at 25° C. for 60 hours, then the product isolated and purified by the procedure of the preceding Example to obtain benzyl 6-(2,6-dimethoxybenzamido)penicillanoyloxymethyl dimethylmalonate in 65% yield. $^1$H-NMR (CDCl$_3$) ppm (delta): 1.46 (s, 9H), 1.6 (s, 3H), 3.78 (s, 6H), 4.38 (s, 1H), 5.16 (s, 2H), 5.5–6.1 (m, 4H), 6.53 (d, 2H), 7.1–7.43 (m, 1H), 7.3 (s, 5H).

To 3.5 g (5.7 mmole) of this benzyl ester in 50 ml ethyl acetate is added 2.5 g 10% Pd/C catalyst and the mixture hydrogenated at 50 psi pressure for one hour. After filtering to remove catalyst, to the filtrate is added an equimolar amount of sodium 2-ethylhexanoate in ethyl acetate. The product sodium salt is precipitated with ethyl ether and collected by filtration to yield 1.95 g (63%) of the title compound. $^1$H-NMR (D$_2$O) ppm (delta): 1.33 (s, 6H), 1.42 (s, 3H), 1.6 (s, 3H), 3.73 (s, 6H), 4.4–4.8 (HOD signal), 5.5–5.8 (m, 2H), 5.78 (dd, 2H), 6.6 (d, 2H), 7.13–7.46 (m, 1H); infrared spectrum (KBr): 1787 cm$^{-1}$.

EXAMPLE 19

The procedure of the preceding example is repeated with sodium 6-(2,6-dimethoxybenzamido)penicillanate and benzyl chloromethyl glutarate on a 2.2 mmolar scale to provide benzyl 6-(2,6-dimethoxybenzamido)-penicillanoyloxymethyl glutarate in quantitative yield as an oil. $^1$H-NMR (CDCl$_3$) ppm (delta): 1.48 (s, 3H), 1.61 (s, 3H), 1.7–2.2 (m, 2H), 2.2–2.62 (m, 4H), 3.8 (s, 6H), 4.38 (s, 1H), 5.08 (s, 2H), 5.5–6.06 (m, 4H), 6.5 (d, 2H), 7.1–7.38 (m, 1H), 7.3 (s, 5H).

Hydrogenation of 1.4 g (2.2 mmole) of the above benzyl ester over Pd/C catalyst by the method used in the previous examples and conversion to sodium salt with sodium 2-ethylhexanoate affords 0.87 g (72.5%) of sodium 6-(2,6-dimethoxybenzamido)penicillanoxyloxymethyl glutarate. $^1$H-NMR (D$_2$O) ppm (delta): 1.43 (s, 3H), 1.58 (s, 3H), 1.5–2.5 (m, 6H), 3.75 (s, 6H), 4.4–4.7 (HOD signal), 5.5–5.9 (m, 4H), 6.6 (d, 2H), 7.13–7.5 (m, 1H); infrared spectrum (KBr): 1786 cm$^{-1}$.

EXAMPLE 20

1,1-Dioxopenicillanoyloxymethyl 6-[D-(2-[1-methyl-2-methoxycarbonylvinylamino]-2-phenylacetamido)]penicillanoyloxymethyl trans-1,4-cyclohexanedicarboxylate A mixture of 2.33 g (3.97 mmole) sodium 1,1-dioxopenicillanoyloxymethyl trans-1,4-cyclohexanedicarboxylate, 1.72 g (3.97 mmole) iodomethyl 6-[D-(2-[1-methyl-2-methoxycarbonylvinylamino]-2-phenylacetamido)]penicillanate and 40 ml dimethylformamide is stirred at room temperature for five minutes. The mixture is diluted with ethyl acetate, washed three times with small portions of water, once with brine and dried (Na$_2$SO$_4$). Evaporation of the solvent in vacuo and chromatography of the residue on a silica gel golumn, eluting with 7:3 ethyl acetate/hexane affords 1.4 g (40%) of the desired enamine. $^1$H-NMR (CDCl$_3$) ppm (delta): 1.3–2.4 (m, 16H), 3.3–3.7 (m, 5H), 4.3–4.4 (s, 2H), 4.5–4.7 (m, 2H), 5.0–5.2 (d, 1H), 5.3–5.4 (m, 2H), 5.5–5.9 (m, 4H), 6.5–6.8 (d, 1H), 7.3 (s, 5H); infrared spectrum (KBr) cm$^{-1}$: 1600, 1760, 1800.

EXAMPLE 21

1,1-Dioxopenicillanoyloxymethyl 6-[D-(2-amino-2-phenylacetamido)]penicillanoyloxymethyl trans-1,4-cyclohexanedicarboxylate Hydrochloride To a solution of 1.4 g (1.61 mmole) 1,1-dioxopenicillanoyloxymethyl 6-[D-(2-[1-methyl-2-methoxycarbonylvinylamino]-2-phenylacetamido)]penicillanoyloxymethyl trans-1,4-cyclohexane dicarboxylate in 150 ml acetone is added 20 ml 0.1N hydrochloride acid and the solution is stirred for five minutes. The solvent is evaporated in vacuo, the residue diluted with water and the aqueous phase washed twice with 1:1 ethyl ester/ethyl acetate. The aqueous phase is filtered and freeze dried to obtain 634 mg (48%) of the title compound, m.p. 155°–170° (decomp.). $^1$H-NMR (DMSO-D$_6$ with D$_2$O exchange) ppm (delta): 1.25–1.5 (m, 16H), 1.85–1.95 (m, 4H), 2.35–2.5 (m, 2H), 3.3 (dd, 1H), 3.7 (dd, 1H), 4.4 (s, 1H), 4.55 (s, 1H), 5.1 (s, 1H), 5.2 (q, 1H), 5.45 (d, 1H), 5.55–5.65 (q, 1H), 5.7–5.95 (m, 4H), 7.4–7.6 (m, 5H), 8.85 (bs, 3H), 9.45 (d, 1H); infrared spectrum (KBr) cm$^{-1}$: 1690, 1760, 1800.

EXAMPLE 22

Benzyl Chloromethyl Sebacate

To a mixture of 48.67 g (0.155 mole) monobenzyl sebacate, 26.04 g (0.310 mole) sodium bicarbonate, 200 ml water and 52.55 g (0.155 mole) tetrabutylammonium hydrogen sulfate is added 100 ml chloroform. After shaking, the organic layer is separated, the aqueous phase extracted again with chloroform and the combined chloroform layers dried (Na$_2$SO$_4$). Evaporation of solvent affords a residue which is taken up in 50 ml bromochloromethane and stirred overnight at room temperature. The mixture is evaporated in vacuo, the residue mixed with ethyl acetate, filtered and the filtrate concentrated in vacuo. The residual crude product is purified by column chromatography on silica gel to afford 2 g of purified monoester as an oil. $^1$H-NMR (CDCl$_3$) ppm (delta): 1.1–1.9 (m, 12H), 2.2–2.5 (m, 4H), 5.0 (s, 2H), 5.6 (s, 2H), 7.3 (s, 5H).

EXAMPLE 23

1,1-Dioxopenicillanoyloxymethyl 6-[D-(2-[1-methyl-2-methoxycarbonylvinylamino[-2-phenylacetamido)]-penicillanoyloxymethyl Sebacate To a solution of 0.59 g (1.0 mmole) iodomethyl 6-[D-(2-[1-methyl-2-methoxycarbonylvinylamino]-2-phenylacetamido)]penicillanate in 10 ml dimethylformamide is added 0.47 g (1.0 mmole) sodium 1,1-dioxopenicillanoyloxymethyl sebacate and the mixture is stirred until solution is complete. The reaction mixture is flash chromatographed on a 23 cm silica gel column bed, eluting with 7:3 ethyl acetate/hexane to obtain 200 mg (22%) of the desired enamine. $^1$H-NMR (CDCl$_3$) ppm (delta): 1.2–1.8 (m, 24H), 1.9 (s, 3H), 2.2–2.6 (m, 4H), 3.4–3.8 (m, 5H), 4.4 (s, 2H), 4.6–4.7 (m, 2H), 5.2 (d, 1H), 5.3 (s, 1H), 5.6–6.0 (m, 4H), 6.9 (d, 1H), 7.3 (s, 5H).

EXAMPLE 24

1,1-Dioxopenicillanoyloxymethyl 6-[D-(2-amino-2-phenylacetamido)]penicillanoyloxymethyl Sebacate Hydrochloride To a stirred solution of 200 mg (0.22 mmole) penicillanoyloxymethyl 6-[D-(2-[1-methyl-2-methoxycarbonylvinylamino]-2-phenylacetamido)]penicillanoyloxymethyl sebacate in 25 ml acetone is added 3.2 ml 0.1N hydrochloride acid and the mixture is stirred for a few minutes, an additional 1.0 ml hydrochloric acid added and stirring continued for one more minute. The acetone is evaporated, the residue diluted with water, and washed twice with 1:1 ethyl ether/ethyl acetate. The aqueous layer is filtered and freeze dried to obtain 110 mg (59%) of product. $^1$H-NMR (DMSO-D$_6$+D$_2$O exchange) ppm (delta): 1.2–1.6 (m, 24H), 2.4 (q, 4H), 3.3 (d, 1H), 3.65–3.75 (dd, 1H), 4.4 (s, 1H), 4.55 (s, 1H), 5.05 (s, 1H), 5.2 (q, 1H), 5.45 (d, 1H), 5.55–5.65 (m, 1H), 5.7–5.9 (m, 4H), 7.35–7.55 (m, 5H), 8.65 (bs, 3H), 9.45 (d, 1H).

EXAMPLE 25

1,1-Dioxopenicillanoyloxymethyl 6-[D-(2-amino-2-phenylacetamido)]penicillanoyloxymethyl Terephthalate Hydrochloride

A

1,1-Dioxopenicillanoyloxymethyl 6-[D-(2-[1-methyl-2-methoxycarbonylvinylamino]-2-phenylacetamido)]penicillanoyloxymethyl terephthalate To a solution of 0.59 g (1 mmole) iodomethyl 6-[D-(2-[1-methyl-2-methoxycarbonylvinylamino]-2-phenylacetamido)]penicillanate in 10 ml dimethylformamide is added 0.48 g (1.1 mmole) sodium 1,1-dioxopenicillanoyloxymethyl terephthalate and the mixture stirred until a solution is obtained. The solution is diluted with ethyl acetate and washed with small portions of water (3×), once with brine and dried (Na$_2$SO$_4$). The solvent is evaporated in vacuo, the residue taken up in a small amount of ethyl acetate and purified by silica gel chromatography eluting with ethyl acetate/hexane, 6:4. The product containing fractions are evaporated to provide 0.3 g (23%) of the enamine protected compound. $^1$H-NMR (CDCl$_3$) ppm (delta): 1.1–1.5 (m, 12H), 1.7 (s, 3H), 3.3–3.6 (m, 5H), 4.4 (s, 2H), 4.4–4.6 (m, 2H), 5.1 (d, 1H), 5.4 (s, 1H), 5.8–6.1 (m, 4H), 6.9 (d, 1H), 7.2 (s, 5H), 8.0 (s, 4H).

B

To a stirred solution of 0.3 g (0.35 mmole) of the above enamine protected product in 25 ml acetone is added 4.5 ml 0.1N hydrochloric acid. The resulting mixture is stirred for a few minutes, the solvent evaporated and the residue partitioned between water and ethyl ether. The aqueous phase is then washed with 1:1 ethyl ether/ethyl acetate, filtered and the filtrate is freeze dried to obtain 222 mg (78%) of the title hydrochloride salt. $^1$H-NMR (DMSO+D$_2$O) ppm (delta): 1.25–1.4 (d, 6H), 1.4–1.5 (d, 6H), 3.2–3.3 (d, 1H), 3.65–3.75 (dd, 1H), 4.45 (s, 1H), 4.6 (s, 1H), 5.1 (s, 1H), 5.2 (d, 1H), 5.45–5.5 (d, 1H), 5.55–5.65 (m, 1H), 6.0–6.4 (m, 4H), 7.35–7.55 (m, 5H), 8.15 (s, 4H), 8.85 (bs, 3H), 9.45 (d, 1H); infrared spectrum (KBr) cm$^{-1}$: 1690, 1740, 1800.

EXAMPLE 26

1,1-Dioxopenicillanoyloxymethyl 6-[D-(2-amino-2-phenylacetamido)]penicillanoyloxymethyl Isophthalate Hydrochloride

A

1,1-Dioxopenicillanoyloxymethyl 6-[D-(2-[1-methyl-2-methoxycarbonylvinylamino]-2-phenylacetamido)]penicillanoyloxymethyl isophthalate To a solution of 0.59 g (110 mmole) iodomethyl 6-[D-(2-[1-methyl-2-methoxycarbonylvinylamino]-2-phenylacetamido)]penicillanate in 10 ml dimethylformamide is added 0.43 g (1.0 mmole) sodium 1,1-dioxopenicillanoyloxymethyl isophthalate and the mixture is stirred at room temperature until solution is complete. The reaction mixture is worked up by the procedure of the preceding example (Part A) to provide 200 mg (23%) of the coupled enamine. $^1$H-NMR (CDCl$_3$) ppm (delta): 1.3–1.6 (m, 12H), 1.85 (s, 3H), 3.6 (s, 3H), 3.4–3.55 (m, 2H), 4.45 (s, 2H), 4.6–4.7 (m, 2H), 5.2 (d, 1H), 5.4–5.7 (m, 2H), 5.9–6.2 (m, 4H), 6.9 (bd, 1H), 7.3 (s, 5H), 7.5–7.7 (m, 1H), 8.1–8.4 (m, 2H), 8.7 (bs, 1H), 9.4 (d, 1H).

B

The enamine protecting group is removed and the hydrochloride salt formed by the method of the previous Example, Part B in 94% yield. $^1$H-NMR (DMSO+D$_2$O) ppm (delta): 1.3 (d, 6H), 1.5 (d, 6H), 3.7 (dd, 1H), 3.3 (d, 1H), 4.5 (s, 1H), 4.65 (s, 1H), 5.1 (s, 1H), 5.2 (d, 1H), 5.45 (d, 1H), 5.55–5.65 (m, 1H), 6.0–6.2 (m, 4H), 7.35–7.55 (m, 5H), 7.8 (t, 1H), 8.25–8.35 (m, 2H), 8.48 (t, 1H), 8.85 (bs, 3H), 9.45 (d, 1H); infrared spectrum (KBr): 1750–1800 cm$^{-1}$ (broad).

EXAMPLE 27

6-[D-(2-Amino-2-phenylacetamido)]-penicillanoyloxymethyl 1,1-dioxopenicillanoyloxymethyl succinate hydrochloride [VIII, R$^4$=H, Q$^1$=NH$_2$, A=(CH$_2$)$_2$]

To a solution of 5.9 g (0.01 mole) iodomethyl 6-[D-(2-[1-methyl-2-methoxycarbonylvinylamino]-2-phenylacetamido)]penicillanate in 30 ml dimethylformamide was added 5.5 g (0.014 mmole) of sodium 1,1-dioxopenicillanoyloxymethyl succinate with stirring. After 20 minutes 150 ml of ethyl acetate was added and the mixture washed with water (3×50 ml), brine (50 ml), water (2×50 ml), brine (50 ml), dried (Na$_2$SO$_4$) and concentrated to 6.3 g of a yellow foam. The product was dissolved in 60 ml of acetone and hydrolyzed by stirring with 80 ml of 0.1N hydrochloric acid for 15 minutes. The acetone was removed in vacuo and the aqueous residue extracted with ethyl acetate (50 ml), ethyl acetate/ethyl ether (1:1, 75 ml) and ethyl acetate (50 ml) again. The aqueous phase was filtered to give a clear solution which produced 2.95 g of a solid mixture upon freeze drying. Chromatography on Sephadex LH-20 (water) gave 0.26 g (3%) of pure hydrochloride salt. $^1$H-NMR (perdeutero dimethylsulfoxide) ppm (delta): 1.4 (s, 6H), 1.52 (s, 6H), 2.7 (s, 4H), 3.1–3.95 (m, 2H), 4.4 (s, 1H), 4.52 (s, 1H), 5.0–5.28 (m, 2H), 5.3–5.68 (m, 2H), 5.68–6.0 (m, 4H), 7.43 (broad s, 5H); infrared spectrum (nujol) cm$^{-1}$: 1810–1730 (broad).

a.

6-[D-(2-Amino-2-phenylacetamido)]penicillanoyloxymethyl 1,1-dioxopenicillanoyloxymethyl glutarate hydrochloride [VIII, $R^4$=H, $Q^1$=NH$_2$, A=(CH$_2$)$_3$]

Similarly, 2.94 g (5 mmole) of the same iodomethyl ester of methyl acetoacetate enamine protected ampicillin and 3.0 g (7.5 mmole) sodium 1,1-dioxopenicillanoyloxymethyl glutarate were stirred in 20 ml dimethylformamide for five minutes and quenched with 150 ml ethyl acetate. The mixture was washed with water (3×50 ml), brine (50 ml), dried (Na$_2$SO$_4$) and evaporated to dryness in vacuo. The residue was purified by chromatography on silica gel (100 g), eluting with methylene chloride/ethyl acetate (60:40 by volume) taking fractions every 60 seconds. Fractions 16–24 were combined and the solvent evaporated to afford 1.8 g of foam. This was dissolved in 30 ml acetone, 21.5 ml 0.1N hydrochloric acid was added and the mixture stirred for 20 minutes. The acetone was evaporated at reduced pressure, the aqueous phase extracted with ethyl ether (30 ml) and 1:1 ethyl acetate/ethyl ether. The aqueous layer was filtered through diatomaceous earth and the filtrate lyophilized to afford 1.45 g (37%) of the desired hydrochloride salt.

$^1$H-NMR (perdeutero dimethylsulfoxide) ppm (delta): 1.4 (s, 6H), 1.52 (s, 6H), 1.5–2.0 (m, 2H), 2.2–2.5 (m, 4H), 3.06–3.9 (m, 2H), 4.38 (s, 1H), 4.5 (s, 1H), 5.03–5.26 (m, 2H), 5.33–5.63 (m, 2H), 5.63–5.93 (m, 4H), 7.43 (broad s, 5H); infrared spectrum (Nujol) cm$^1$: 1815–1730.

The following compounds are also obtained by the above method:

b.

6-[D-(2-Amino-2-phenylacetamido)]penicillanoyloxymethyl 1,1-dioxopenicillanoyloxymethyl adipate hydrochloride [VIII, $R^4$=H, $Q^1$=NH$_2$, A=(CH$_2$)$_4$]—(50% yield)*—$^1$H-NMR (perdeutero dimethylsulfoxide) ppm (delta): 1.4 (s, 6H), 1.5 (s, 6H), (both of these singlets are on top of a multiplet for 4H atoms), 2.2–2.6 (m, 4H), 3.06–3.93 (m, 2H), 4.4 (s, 1H), 4.53 (s, 1H), 5.06–5.26 (m, 2H), 5.36–5.96 (m, 6H), 7.46 (broad s, 5H); infrared spectrum (nujol) cm$^{-1}$: 1815–1725.

*Upon purification by chromatography on Sephadex LH20 (Pharmacia Fine Chemicals Co.), material is obtained which is 95% pure by high pressure liquid chromatography assay.

c.

6-[D-(2-Amino-2-phenylacetamido)]pencillanoyloxymethyl 1,1-dioxopenicillanoyloxymethyl dimethylmalonate hydrochloride [VIII, $R^4$=H, $Q^1$=NH$_2$, A=(CH$_3$)$_2$C]—(76% yield)—250 MHz $^1$H-NMR (perdeutero dimethylsulfoxide) ppm (delta): 1.341 (s, 6H), 1.366 (s, 6H), 1.48 (s, 6H), 3.0–3.9 (m, 2H), 4.41 (s, 1H), 4.53 (s, 1H), 5.116 (broad s, 1H), 5.2 (broad s, 1H), 5.46 (d, 1H), 5.55–5.65 (m, 1H), 5.7–6.0 (m, 4H), 7.33–7.64 (m, 5H), 8.88 (broad s, 3H), 9.45 (d, 1H); infrared spectrum (nujol) cm$^{-1}$: 1815–1770.

d.

6-[D-(2-Amino-2-phenylacetamido)]penicillanoyloxymethyl 1,1-dioxopenicillanoyloxymethyl malonate hydrochloride [VIII, $R^4$=H, $Q^1$=NH$_2$, A=CH$_2$]—(80% yield)—$^1$H-NMR (dimethylsulfoxide) ppm (delta): 1.33 (s, 6H), 1.46 (s, 6H), 3.0–3.9 (m, 2H), 3.73 (s, 2H), 4.36 (s, 1H), 4.46 (s, 1H), 5.0–5.26 (m, 2H), 5.3–5.96 (m, 6H), 7.4 (broad s, 5H).

EXAMPLE 28

6-[D-(2-Amino-2-phenylacetamido)]penicillanoyloxymethyl 1,1-dioxopenicillanoyloxymethyl glutarate hydrochloride [VIII, $R^4$=H, $Q^1$=NH$_2$, A=(CH$_2$)$_3$]

A

6-[D-(2-Azido-2-phenylacetamido)]penicillanoyloxymethyl 1,1-dioxopenicillanoyloxymethyl glutarate To a mixture of 1.18 g (0.0023 mole) of iodomethyl 6-[D-(2-azido-2-phenylacetamido)]penicillanate and 1.2 g (0.003 mole) of sodium 1,1-dioxopenicillanoyloxymethyl glutarate was added 15 ml of dimethylformamide and the mixture stirred into solution. After one hour an additional 1.0 g of sodium salt was added and the solution stirred an additional 30 minutes, diluted with ethyl acetate (100 ml) and washed with brine (2×30 ml), water (2×30 ml), brine (1×30 ml), dried (Na$_2$SO$_4$) and concentrated in vacuo to a foam. Chromatography on silica gel (100 g), eluting with 7:3 ethyl acetate/hexane, gave 0.72 g (43%) of purified azido compound. $^1$H-NMR (CDCl$_3$) ppm (delta): 1.41 (s, 3H), 1.5 (s, 3H), 1.6 (s, 3H), 1.63 (s, 3H), 1.77–2.23 (m, 2H), 2.26–2.66 (m, 4H), 3.42 (d, 2H), 4.38 (s, 1H), 4.43 (s, 1H), 4.58 (t, 1H), 5.06 (s, 1H), 5.4–5.9 (m, 6H), 7.1 (d, 1H), 7.33 (s, 5H).

B

The azide product obtained above was dissolved in 15 ml of dichloromethane and 15 ml of isopropanol and combined with 0.5 g of 10% palladium on carbon. The mixture was hydrogenated under 50 psi (3.52 kg/cm$^2$) of hydrogen for 45 minutes. After addition of another 0.25 g of catalyst, hydrogenation was continued for another 30 minutes. The catalyst was removed by filtration, washed with dichloromethane/isopropanol and the filtrate concentrated in vacuo to give about 3 ml of a suspension. Addition of 30 ml of diethyl ether gave a precipitate which, after stirring for 5 minutes and filtration, gave 0.24 g (35%) of free base. A 0.21 g portion of the base was dissolved in 2.8 ml of 0.1N hydrochloric acid and freeze dried after filtration through diatomaceous earth to give 0.14 g of hydrochloride salt.

A sample of the free base was used to obtain $^1$H-NMR (perdeutero dimethylsulfoxide) ppm (delta): 1.38 (s, 3H), 1.43 (s, 3H), 1.5 (s, 3H), 1.6 (s, 3H), 1.65–2.0 (m, 2H), 2.25–2.6 (m, 4H partially obstructed by DMSO), 3.1–3.9 (m, 2H), 4.43 (s, 1H), 4.5 (broad s, 2H), 5.03–5.2

(m, 1H), 5.36–5.6 (m, 2H), 5.6–5.9 (m, 4H), 7.26 (broad s, 5H).

EXAMPLE 29

6-[D-(2-Amino-2-phenylacetamido)]-penicillanoyloxymethyl 1,1-dioxopenicillanoyloxymethyl adipate hydrochloride

A

By employing sodium 1,1-dioxopenicillanoyloxymethyl adipate in place of sodium 1,1-dioxopenicillanoyloxymethyl glutarate in the procedure of Example 5, Part A afforded 6-[D-(2-azido-2-phenylacetamido)]-penicillanoyloxymethyl 1,1-dioxopenicillanoyloxymethyl adipate in 37.7% yield, $^1$H-NMR (CDCl$_3$) ppm (delta): 1.45 (s, 3H), 1.55 (s, 3H), 1.63 (s, 3H), 1.68 (s, 3H), (previous singlets on top of m, 4H), 2.2–2.6 (m, 4H), 3.48 (d, 2H), 4.43 (s, 1H), 4.48 (s, 1H), 4.65 (t, 1H), 5.12 (s, 1H), 5.5–5.95 (m, 6H), 7.15 (d, 1H), 7.38 (s, 5H).

B

The free base of the title compound was obtained upon hydrogenation of the azido compound obtained in Part A by the procedure of Example 5, Part B. It was converted to the hydrochloride salt as also described in Example 5B, identical to that obtained in Example 4, Part b.

C

The following 2-azido compounds are obtained in like manner and hydrogenated to provide the corresponding 2-amino compounds

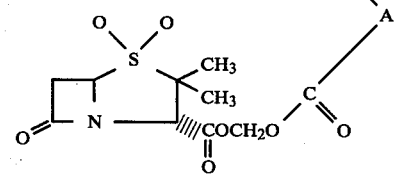

| R$^4$ | A |
|---|---|
| H | (CH$_2$)$_2$ |
| OH | CH$_2$ |
| OCHO | C(CH$_3$)$_2$ |
| OCOCH$_2$CH$_3$ | C(C$_2$H$_5$)$_2$ |
| OCOCH(CH$_3$)$_2$ | (CH$_2$)$_5$ |
| OCO(CH$_2$)$_3$CH$_3$ | (CH$_2$)$_7$ |
| OCO(CH$_2$)$_5$CH$_3$ | (CH$_2$)$_{11}$ |
| OCO(CH$_2$)$_3$CH(CH$_3$)$_2$ | (CH$_2$)$_{12}$ |
| OCOOCH$_3$ | CHCH$_3$ |
| OCOOC$_2$H$_5$ | CHCH$_2$CH$_3$ |
| OCOOCH(CH$_3$)$_2$ | CH$_2$CH(CH$_3$) |
| OCOOCH$_2$CH$_2$CH$_3$ | (CH$_3$)CHCH(CH$_3$) |
| OCOOCH$_2$CH(CH$_3$)$_2$ | CH$_2$C(CH$_3$)$_2$CH$_2$ |
| OCOOC(CH$_3$)$_3$ | CH$_2$CH(CH$_3$)CH$_2$ |
| OCOOC(CH$_3$)$_2$CH$_2$CH$_3$ | CH$_2$C(C$_2$H$_5$)$_2$CH$_2$ |
| OCOOCH$_2$CH$_2$C(CH$_3$)$_3$ | CH$_2$C(CH$_3$)(C$_2$H$_5$)CH$_2$ |
| OCOO(CH$_2$)$_5$CH$_3$ | CH$_2$CH(CH$_3$)CH$_2$CH$_2$ |
| OCOOC(CH$_3$)$_3$ | CH(CH$_3$)CH$_2$CH$_2$ |
| OCOOC$_6$H$_5$ | CH$_2$CH(CH$_3$)CH$_2$ |
| OCOO(4-FC$_6$H$_4$) | (CH$_3$)$_2$CCH$_2$CH$_2$ |
| OCOO(2-ClC$_6$H$_4$) | CH$_2$C(CH$_3$)$_2$CH$_2$ |
| OCO(3-BrC$_6$H$_4$) | CH(CH$_3$)CH$_2$ |
| OCO(4-IC$_6$H$_4$) | (CH$_2$)$_8$ |

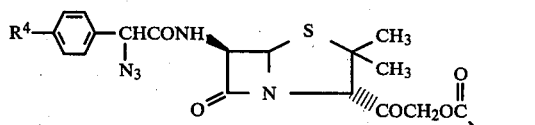

| R$^4$ | A |
|---|---|
| OCO(4-ClC$_6$H$_4$) | (CH$_2$)$_3$ |
| OCO(4-CNC$_6$H$_4$) | (CH$_2$)$_6$ |
| OCO(2-CH$_3$C$_6$H$_4$) | C(CH$_3$)$_2$ |
| OCO[4-(CH$_3$)$_2$CHC$_6$H$_4$] | CHCH$_3$ |
| OCOO[4-(CH$_3$)$_3$CC$_6$H$_4$] | CH$_2$ |
| OCOO(4-CH$_3$OC$_6$H$_4$) | (CH$_2$)$_2$ |
| OCO(3-C$_2$H$_5$OC$_6$H$_4$) | CH$_2$ |
| OCOO(2-n-C$_3$H$_7$OC$_6$H$_4$) | C(C$_2$H$_5$)$_2$ |
| OCO(2-n-C$_4$H$_9$OC$_6$H$_4$) | (CH$_2$)$_4$ |
| OCOO[3-(CH$_3$)$_3$COC$_6$H$_4$] | (CH$_2$)$_3$ |
| OCO[4-(CH$_3$)$_2$CHCH$_2$OC$_6$H$_4$] | (CH$_3$)CHCH$_2$ |
| OCHO | CH$_2$ |
| OCHO | (CH$_2$)$_4$ |
| OCHO | CHCH$_3$ |
| H | 1,4-cyclohexyl |
| OH | 1,3-cyclobutyl |
| OCOCH(CH$_3$)$_2$ | 1,4-cycloheptyl |
| OCOCH$_3$ | 1,4-phenylene |
| OCOC$_2$H$_5$ | 1,3-phenylene |
| OCOOC$_6$H$_5$ | 1,2-phenylene |

OCOOC(CH$_3$)$_3$

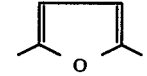

OCOOCH$_2$CH$_2$CH$_3$

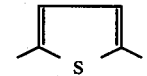

H

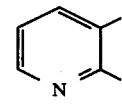

HO

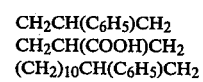

| | |
|---|---|
| H | CH$_2$CH(C$_6$H$_5$)CH$_2$ |
| HO | CH$_2$CH(COOH)CH$_2$ |
| OCOCH$_3$ | (CH$_2$)$_{10}$CH(C$_6$H$_5$)CH$_2$ |

H

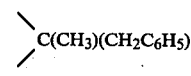

HO

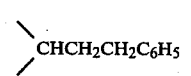

EXAMPLE 30

Chloromethyl 1,1-dioxopenicillanoyloxymethyl glutarate

A solution of 3.9 g (0.0084 mole) of benzyl 1,1-dioxopenicillanoyloxymethyl glutarate in 50 ml of tetrahydrofuran (THF) was hydrogenated in the presence of 3.0 g of 10% palladium on carbon under 50 psi (3.52 kg/cm$^2$) of hydrogen with a Paar hydrogenation apparatus. The catalyst was removed by filtration and the cake washed with THF and the filtrates concentrated in vacuo to 3.5 g of a viscous oil. The oil was dissolved in 25 ml of chloroform, overlaid with 10 ml of water, the mixture stirred and adjusted to pH 8.0 by addition of 40% tetrabutylammonium hydroxide. The chloroform layer was separated and the aqueous layer extracted with chloroform (2×30 ml). The combined chloroform layers were dried (Na$_2$SO$_4$) and concentrated in vacuo to give 5.8 g of an oil, which was dissolved in 35 ml of iodochloromethane and stirred 15 hours. Concentration in vacuo and chromatography on silica gel (ethyl acetate/hexane) gave 0.20 g (6%) of the title compound. $^1$H-NMR (CDCl$_3$) ppm (delta): 1.44 (s, 3H), 1.63 (s, 3H), 1.82–2.2 (m, 2H), 2.26–2.7 (m, 4H), 3.48 (d, 2H), 4.43 (s, 1H), 4.63 (t, 1H), 5.72 (s, 2H), 5.83 (AB quartet, 2H).

EXAMPLE 31

6-[D-(2-Amino-2-phenylacetamido)]-penicillanoyloxymethyl 1,1-dioxopenicillanoyloxymethyl glutarate hydrochloride [VIII, R$^4$=H, Q$^1$=NH$_2$, A=(CH$_2$)$_3$]

To a solution of 0.2 g (0.0005 mole) of chloromethyl 1,1-dioxopenicillanoyloxymethyl glutarate in 2 ml of acetone was added 0.323 g (0.0005 mole) of tetrabutylammonium 6-[D-(2-[1-methyl-2-methoxycarbonylvinylamino]-2-phenylacetamido)]pencillanate with stirring. After stirring 20 hours at room temperature the solvent was removed in vacuo and the residue chromatographed on silica gel, eluting with 7:3 ethyl acetate/hexane, to give 0.18 g of an oil. To a solution of the product oil in 15 ml of acetone was added 2 ml of 0.1N hydrochloric acid followed by an additional 5 ml of water and the mixture (pH 1.2) was stirred 30 minutes. Acetone was removed in vacuo and the aqueous residue was washed with ethyl ether (2×30 ml), filtered, and freeze dried to give 0.12 g (75% based on enamine) of hydrochloride salt.

EXAMPLE 32

Iodomethyl 1,1-dioxopenicillanoyloxymethyl dimethylmalonate

A

Chloromethyl 1,1-dioxopenicillanoyloxymethyl dimethylmalonate

To a solution of 10 g (0.025 mole) of sodium 1,1-dioxopenicillanoyloxymethyl dimethylmalonate in 25 ml of water was added 150 ml of chloroform followed by 8.5 g (0.025 mole) of tetrabutylammonium hydrogen sulfate. The aqueous layer was adjusted with stirring to pH 7.5 by addition of sodium bicarbonate. The chloroform layer was separated and the aqueous phase extracted with chloroform (1×100 ml). The combined chloroform layers were dried (Na$_2$SO$_4$) and concentrated in vacuo to give 19.5 g of a viscous oil still containing chloroform. The oil was dissolved in 95 ml of chloroiodomethane and stirred overnight. Concentration in vacuo and chromatography on 300 g of silica gel, eluting with ethyl acetate/hexane 1:1 by volume, gave 7.4 g (70%) of chloromethyl ester as an oil. $^1$H-NMR (CDCl$_3$) ppm (delta): 1.43 (s, 3H), 1.5 (s, 6H), 1.6 (s, 3H), 3.45 (d, 2H), 4.38 (s, 1H), 4.6 (t, 1H), 5.68 (s, 2H), 5.8 (AB quartet, 2H).

B

To a solution of 7.4 g (0.0156 mole) of chloromethyl 1,1-dioxopenicillanoyloxymethyl dimethylmalonate in 50 ml of acetone was added 11.75 g (0.078 mole) of sodium iodide and the solution stirred 20 hours. Concentration in vacuo gave an oily solid which was partitioned between 50 ml of water and 100 ml of ethyl acetate. The aqueous layer was separated and the organic layer washed with water (50 ml), brine (50 ml), dried (Na$_2$SO$_4$) and concentrated in vacuo to a yellow oil. Chromatography on 150 g of silica gel, eluting with 1:1 ethyl acetate/hexane (by volume), gave 8.3 g (100%) of iodomethyl ester as a clear viscous oil. $^1$H-NMR (CDCl$_3$) ppm (delta); 1.48 (s, 3H), 1.52 (s, 6H), 1.65 (s, 3H), 3.46 (d, 2H), 4.45 (s, 1H), 4.65 (t, 1H), 5.83 (AB quartet, 2H), 5.93 (s, 2H); infrared (neat) cm$^{-1}$: 1810–1735.

C

The above procedures are repeated, but starting with one of the remaining sodium or potassium salts provided in Example 4, to provide the following compounds

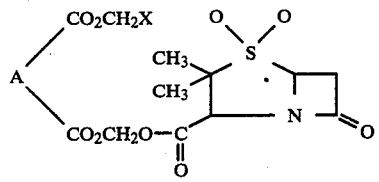

where A is as defined in Example 4 and X is Cl or I.

EXAMPLE 33

6-[D-(2-Amino-2-[p-hydroxyphenyl]-acetamido)]-penicillanoyloxymethyl 1,1-dioxopenicillanoyloxymethyl dimethylmalonate hydrochloride [VIII, R$^4$=OH, Q$^1$=NH$_2$, A=(CH$_3$)$_2$C]

A

6-[D-(2-[1-methyl-2-methoxycarbonylvinylamino]-2-[p-hydroxyphenyl]acetamido)]penicillanoyloxymethyl 1,1-dioxopenicillanoyloxymethyl dimethylmalonate To a mixture of 1.83 g (0.0026 mole) tetrabutylammonium 6-[D-(2-[1-methyl-2-methoxycarbonylvinylamino]-2-[p-hydroxyphenyl]acetamido)]penicillanate and 1.35 g (0.0026 mole) iodomethyl 1,1-dioxopenicillanoyloxymethyl dimethylmalonate was added 10 ml of dimethylformamide. After stirring for 15 minutes, the solution was diluted with 100 ml of ethyl acetate, washed with brine (25 ml), water (3×25 ml), brine (25 ml), dried (Na$_2$SO$_4$) and concentrated to a foam. The foam was taken up in ethyl acetate and chromatographed on 100 g of silica gel, eluting with 1:1 by volume ethyl acetate/hexane, to give 1.2 g (54%) of enamine protected adduct. $^1$H-NMR (CDCl$_3$) ppm (delta): 1.4–1.66 (m, 18H), 1.96 (s, 3H), 3.45 (d, 2H), 3.66 (s, 3H), 4.46 (s, 1H), 4.5 (s, 1H), 4.56–4.73 (m, 2H), 5.02

(d, 1H), 5.43–5.96 (m, 6H), 6.7 (d, 2H), 7.13 (d, 2H); infrared spectrum (nujol) cm$^{-1}$: 1810–1725 (broad).

B

To the above enamine product (1.2 g) dissolved in 30 ml of acetone was added 14 ml of 0.1N hydrochloric acid, after 20 minutes acetone was removed in vacuo and the aqueous residue extracted with ethyl ether (2×50 ml) and ethyl acetate (30 ml). Freeze drying the aqueous phase gave 0.8 g (72%) of the title hydrochloride salt. $^1$H-NMR (perdeutero dimethylsulfoxide) ppm delta: 1.42 (broad s, 12H), 1.53 (s, 6H), 3.05–3.9 (m, 2H), 4.36 (s, 1H), 4.48 (s, 1H), 4.83–5.26 (m, 2H), 5.26–6.0 (m, 6H), 6.73 (d, 2H), 7.23 (d, 2H), infrared spectrum (nujol) cm$^{-1}$: 1815–1725 (broad).

C

By repeating the procedure of Part A above but starting with the appropriate enamine protected alphaaminobenzylpenicillin tertrabutylammonium salt and one of the iodomethyl 1,1-dioxopenicillanoyloxymethyl dicarboxylates provided in Example 32, Part C, provides the corresponding compound of the formula below.

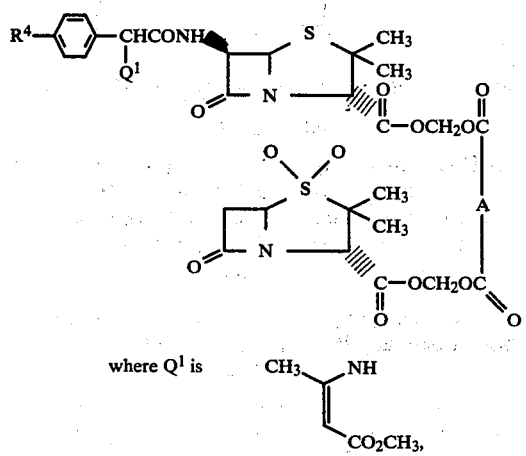

A is as defined in Examples 1–4 and R$^4$ is hydrogen or hydroxy.

EXAMPLE 34

6-[D-(2-Amino-2-[p-acetoxyphenyl]-acetamido)]-penicillanoyloxymethyl 1,1-dioxopenicillanoyloxymethyl dimethylmalonate [VIII, R$^4$=CH$_3$COO, Q$^1$=NH$_2$, A=(CH$_3$)$_2$C]

A

6-[D-(2-[1-methyl-2-methoxycarbonylvinylamino]-2-[p-acetoxyphenyl]acetamido)]penicillanoyloxymethyl 1,1-dioxopenicillanoyloxymethyl dimethylmalonate 6-[D-(2-[1-methyl-2-methoxycarbonylvinylamino]-2-[p-hydroxyphenyl]acetamido)]penicillanoyloxymethyl 1,1-dioxopenicillanoyloxymethyl dimethylmalonate, prepared by the procedure of Example 33, Part A, (2.55 g, 0.003 mole) and 0.366 g (0.003 mole) 4-dimethylaminopyridine were dissolved in 30 ml dichloromethane and 0.28 ml (0.003 mole) of acetic anhydride was added. The solution was stirred for 25 minutes, diluted to 100 ml, washed with water (30 ml), brine (30 ml), dried (Na$_2$SO$_4$) and concentrated to give 2.1 g (78%) of a yellow foam. $^1$H-NMR (CDCl$_3$) ppm (delta): 1.46 (s, 3H), 1.52 (s, 9H), 1.56 (s, 3H), 1.64 (s, 3H), 1.92 (s, 3H), 2.33 (s, 3H), 3.48 (d, 2H), 3.66 (s, 3H), 4.46 (s, 1H), 4.5 (s, 1H), 4.6–4.76 (m, 2H), 5.13 (d, 1H), 5.4–6.0 (m, 6H), 7.1 (d, 2H), 7.43 (d, 2H); infrared spectrum (nujol) cm$^{-1}$: 1810–1725.

B

The foam obtained in Part A, above, 2.1 g, was dissolved in 50 ml of acetone and 23 ml of 0.1N hydrochloric acid was added. After stirring 20 minutes, the acetone was removed in vacuo and the aqueous layer was washed with ethyl ether (2×30 ml) filtered through diatomaceous earth and freeze dried to give 1.77 g (71%) of the title hydrochloride salt. $^1$H-NMR (perdeutero dimethylsulfoxide) ppm (delta): 1.23–1.64 (m, 18H), 2.26 (s, 3H), 3.0–3.9 (m, 2H), 4.36 (s, 1H), 4.46 (s, 1H), 5.0–5.23 (m, 2H), 5.23–5.96 (m, 6H), 7.1 (d, 2H), 7.5 (d, 2H).

EXAMPLE 35

A by repeating the procedure of Example 34, Part A on the same 3 millimolar scale, but using pivaloyl chloride in place of acetic anhydride gave a crude product which was purified by chromatography on 100 g silica gel, eluting with 60:40 (v/v) methylene chloride/ethyl acetate. Concentrations of product-containing fractions gave 2.3 g (82%) of colorless foam which is 6-[D-(2-[1-methyl-2-methoxycarbonylvinylamino]-2-[p-pivaloyloxyphenyl]acetamido)]penicillanoyloxymethyl 1,1-dioxopenicillanoyloxymethyl dimethylmalonate. $^1$H-NMR (CDCl$_3$) ppm (delta): 1.3–1.7 (m, 27H), 1.93 (s, 3H), 3.48 (d, 2H), 3.68 (s, 3H), 4.48 (s, 1H), 4.51 (s, 1H), 4.6–4.73 (m, 2H), 5.13 (d, 1H), 5.46–6.03 (m, 6H), 7.1 (d, 2H), 7.43 (d, 2H); infrared spectrum (nujol) cm$^{-1}$: 1820–1710.

B

To 2.2 g (2.35 mmole) of the enamine obtained in Part A in 30 ml acetone was added 24 ml 0.1N hydrochloric acid. The mixture was stirred at ambient temperature for five minutes, the acetone evaporated in vacuo and the aqueous residue washed with ethyl ether (3×50 ml). The residual ether was removed from the aqueous layer by evaporation in vacuo. The aqueous solution was then clarified by filtration and freeze dried to afford 1.61 g (80%) of 6-[D-(2-amino-2-[p-pivaloyloxyphenyl]acetamido)]penicillanoyloxymethyl 1,1-dioxopenicillanoyloxymethyl dimethylmalonate hydrochloride. $^1$H-NMR (perdeutero dimethylsulfoxide) ppm (delta): 1.16–1.66 (m, 27H), 3.03–3.93 (m, 2H), 4.43 (s, 1H), 4.53 (s, 1H), 5.02–5.26 (m, 2H), 5.33–6.03 (m, 6H), 7.13 (d, 2H), 7.63 (d, 2H); infrared spectrum (nujol) cm$^{-1}$: 1820–1725 (broad).

C

By employing formic-acetic anhydride as acylating agent in Part A and removal of protecting group by the above method, 6-[D-(2-amino-2-[p-formyloxyphenyl]-acetamido)]penicillanoyloxymethyl 1,1-dioxopenicillanoyloxymethyl dimethylmalonate hydrochloride is obtained.

EXAMPLE 36

In like manner the enamine compounds of the formula below where Q$^1$ is

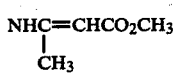

are prepared by the procedures of Example 34, Part A and Example 35, Part A by employing the appropriate acid anhydride, acid chloride or chloroformate ester in place of acetic anhydride and pivaloyl chloride.

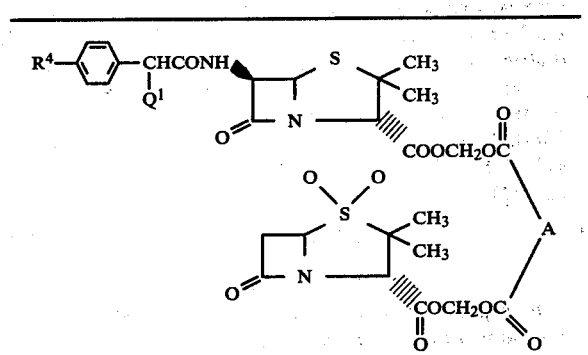

| $R^4$ | A |
|---|---|
| $OCOCH_3$ | $CH_2$ |
| $OCO(CH_2)_2CH_3$ | $(CH_2)_2$ |
| $OCO(CH_2)_3CH_3$ | $(CH_2)_4$ |
| $OCHO$ | $(CH_2)_6$ |
| $OCO(CH_2)_3CH(CH_3)_2$ | $(CH_2)_8$ |
| $OCO(CH_2)_5CH_3$ | $(CH_2)_{10}$ |
| $OCOC_6H_5$ | $CHC_2H_5$ |
| $OCO(3\text{-}CNC_6H_4)$ | $(CH_3)CHCH(CH_3)$ |
| $OCO(2\text{-}CH_3C_6H_4)$ | $(C_2H_5)CHCH(C_2H_5)$ |
| $OCOO(4\text{-}CH_3OC_6H_4)$ | $(CH_3)_2C-C(CH_3)_2$ |
| $OCOOCH(CH_3)_2$ | $(CH_3)CHC(C_2H_5)_2$ |
| $OCOOC(CH_3)_3$ | $C(CH_3)_2$ |
| $OCOOC(CH_3)_3$ | $(CH_2)_2$ |
| $OCOOC(CH_3)_2CH_2CH_3$ | $(n\text{-}C_5H_{11})C(CH_2)_5CH_3$ |
| $OCOOC_6H_5$ | $(CH_2)_{12}$ |
| $OCOO(4\text{-}FC_6H_4)$ | $(n\text{-}C_3H_7)C-CH(n\text{-}C_3H_7)_2$ |

EXAMPLE 37

6-[D-(2-[Benzyloxcarbonylamino]-2-[p-hydroxyphenyl]acetamido)]penicillanoyloxymethyl 1,1-dioxopenicillanoyloxymethyl malonate To 7.40 g (0.010 mole) tetrabutylammonium 6-[D-(2-[benzyloxycarbonylamino]-2-[p-hydroxyphenyl]acetamido)]penicillanate and 4.56 g (0.010 mole) iodomethyl 1,1-dioxopenicillanoyloxymethyl malonate is added 50 ml dimethylformamide and the mixture is stirred for thirty minutes. The reaction mixture is diluted with ethyl acetate (500 ml), washed in turn with brine, water, brine again and dried over anhydrous sodium sulfate. The solvent is evaporated in vacuo and the crude residue purified by chromatography on silica gel.

EXAMPLE 38

6-[D-(2-[4-Nitrobenzyloxycarbonylamino]-2-[p-hydroxyphenyl]acetamido)]penicillanoyloxymethyl 1,1-dioxopenicillanoyloxymethyl malonate The title compound is obtained from tetrabutylammonium 6-[D-(2-[4-nitrobenzyloxycarbonylamino]-2-[p-hydroxyphenyl]acetamido)]penicillanate by the above procedure.

EXAMPLE 39

Employing the appropriate iodomethyl 1,1-dioxopenicillanoyloxymethyl dicarboxylate ester in place of iodomethyl 1,1-dioxopenicillanoyloxymethyl malonate in the procedures of Examples 37 and 38 provides the corresponding compound of the formula below in like manner.

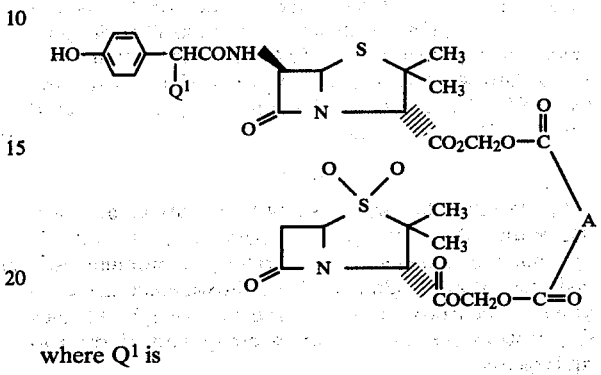

where $Q^1$ is

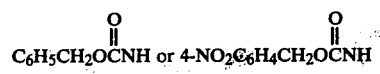

and A has the values given in previous Examples.

EXAMPLE 40

6-[D-(2-Amino-2-[p-isobutoxycarbonyloxyphenyl]-acetamido)]penicillanoyloxymethyl 1,1-dioxopenicillanoyloxymethyl malonate [VIII, $R^4=(CH_3)_2CHCOO$, $Q^1=NH_2$, $A=CH_2$]

A

6-[D-(2-[Benzyloxycarbonylamino]-2-[p-isobutoxycarbonyloxyphenyl]acetamido)]penicillanoyloxymethyl malonate To a stirred solution of 2.48 g (0.003 mole) 6-[D-2-[benzyloxycarbonylamino]-2-[p-hydroxyphenyl]-acetamido)]penicillanoyloxymethyl 1,1-dioxopenicillanoyloxymethyl malonate, 0.487 g (0.003 mole) diisopropylethylamine and 30 ml dichloromethane is added 0.410 g (0.003 mole) isobutyl chloroformate. The resulting mixture is stirred 10 minutes then about 30 mg 4-dimethylaminopyridine is added and stirring continued for 30 minutes. The solvent is evaporated in vacuo, the residue dissolved in ethyl acetate, the solution washed with water, brine, dried ($Na_2SO_4$) and evaporated to dryness in vacuo.

B.

A mixture of 2.0 g of the product obtained in Part A, 50 ml dichloromethane, 50 ml isopropanol and 2.0 g 10% palladium-on-carbon is hydrogenated at three atmospheres (3.52 kg/cm$^2$) until hydrogen uptake ceases. An additional 2.0 g of Pd/C is added and hydrogenation is continued for 30 minutes. The reaction mixture is filtered through Celite (a diatomaceous silica product) washing with 1:1 dichloromethane/isopropanol. The combined filtrate and washings are evaporated in vacuo to afford the crude title compound which can be purified, if desired, by chromatography on Sephadex LH-20*.

*A registered trademark of Pharmacia Fine Chemicals, Piscataway, N.J.

EXAMPLE 41

By employing the appropriate starting material selected from those provided in Examples 38 and 39 in the above procedure or the procedure of Example 34, Part A followed by hydrogenation by the procedure of Example 40, Part B, the following compounds are obtained in like manner.

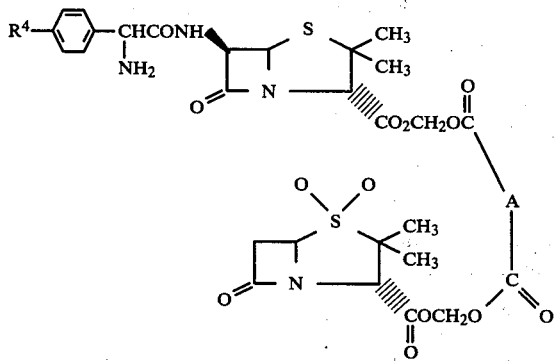

where $R^4$ is as defined in Example 36 and A is as defined in Examples 1-4 and 36.

EXAMPLE 42

Benzyl 6-[D-(2-[1-Methyl-2-methoxycarbonylvinylamino]-2-[p-hydroxyphenyl]acetamido)]-penicillanoyloxymethyl dimethylmalonate To a mixture of 22.2 g (0.10 mole) benzyl dimethylmalonate half ester in 500 ml methylene chloride and 75 ml water is added 40% tetrabutylammonium hydroxide with vigorous stirring until the pH is 8.5. The organic layer is separated, the aqueous layer extracted with methylene chloride (250 ml) and the combined extracts dried ($Na_2SO_4$). Evaporation of solvent gives a residue which is taken up in 500 ml toluene and 54.1 g (0.10 mole) iodomethyl 6-[D-(2-[1-methyl-2-methoxycarbonylvinylamino]-2-[p-hydroxyphenyl]acetamido)]-penicillanate is added and the mixture stirred for one hour, diluted with ethyl acetate (1000 ml) and the precipitated tetrabutylammonium iodide is removed by filtration. The filtrate is washed with water, brine, dried ($Na_2SO_4$) and concentrated to dryness in vacuo. The residual product may be purified by chromatography on silica gel.

EXAMPLE 43

Benzyl 6-[D-(2-[1-methyl-2-methoxycarbonylvinylamino)-2-phenylacetamido)]penicillanoyloxymethyl glutarate 1. Benzyl chloromethyl glutarate A mixture of 1.5 g (3.75 mmole) tetrabutylammonium benzyl glutarate and 20 ml chloroiodomethane is stirred at room temperature for three hours and concentrated in vacuo to a viscous oil. The oil is taken up in 20 ml ethyl acetate and 30 ml hexane and filtered to remove tetrabutylammonium iodide. The solvent is evaporated in vacuo and the residue purified by chromatography on 75 g silica gel, eluting with 70:30 ethyl acetate/hexane by volume. Fractions (15 ml) were collected every 0.7 minutes. The fractions containing the desired product (fractions 8-11) are combined and the solvent evaporated in vacuo to yield 0.55 g (62.5%) of the desired product. $^1$H-NMR ($CDCl_3$) ppm (delta): 1.65-2.2 (m, 2H), 2.26-2.64 (m, 4H), 5.1 (s, 2H), 5.65 (s, 2H), 7.3 (s, 5H).

2. A mixture of 0.55 g (2 mmole) of benzyl chloromethyl glutarate, 1.37 g (2 mmole) tetrabutylammonium 6-[D-(2-[1-methyl-2-methoxycarbonylvinylamino]-2-phenylacetamido)]penicillanate and 20 ml acetone is stirred overnight at room temperature. The acetone is evaporated and the residue purified by chromatography on silica gel, eluting with 60:40 ethyl acetate/hexane by volume to yield 1.2 g (88%) of product as an oil. $^1$H-NMR ($CDCl_3$) ppm (delta): 1.45 (s, 3H), 1.53 (s, 3H), 1.9 (s, 3H), 1.8-2.2 (m, 2H), 2.22-2.62 (m, 4H), 3.64 (s, 3H), 4.4 (s, 1H), 4.62 (s, 1H), 5.05-5.22 (s, 3H), 5.4-5.73 (m, 2H), 5.78 (s, 2H), 6.84 (d, 1H), 7.3 (s, 5H), 7.34 (s, 5H), 9.3 (d, 1H).

EXAMPLE 44

Sodium 6-[D-(2-amino-2-[p-hydroxyphenyl]acetamido]penicillanoyloxymethyl dimethylmalonate

A

Benzyl D-[6-(2-amino-2-[p-hydroxyphenyl]acetamido)]-penicillanoyloxymethyl dimethylmalonate hydrochloride Benzyl 6-[D-(2-[1-methyl-2-methoxycarbonylvinylamino]-2-[p-hydroxyphenyl]acetamido)]penicillanoyloxymethyl dimethylmalonate (6.35 g, 10 mmole) is dissolved in 200 ml acetone, 95 ml 0.1N hydrochloric acid is added and the mixture stirred for 25 minutes. The acetone is then evaporated at reduced pressure, the aqueous residue extracted with ether and filtered to obtain a clarified aqueous solution of the title benzyl ester hydrochloride salt. The solution may be freeze dried if desired to obtain the solid product.

B

To the aqueous solution of benzyl ester hydrochloride obtained in Part A is added 2.5 g of 10% palladium-on-carbon and the mixture is hydrogenated at a pressure of 3-4 atmospheres hydrogen for one hour. The catalyst is removed by filtration, and the filtrate is freeze dried to obtain the hydrochloride salt. The freeze dried solids are taken up in 50 ml ethyl acetate, two equivalents of sodium 2-ethylhexanoate added and the precipitated sodium salt recovered by filtration and dried.

C

In similar manner the product obtained in Example 43 is converted to sodium 6-[D-(2-amino-2-phenylacetamido)]penicillanoyloxymethyl glutarate.

EXAMPLE 45

6-[D-(2-Amino-2-[p-hydroxyphenyl]-acetamido)]-penicillanoyloxymethyl 1,1-dioxopenicillanoyloxymethyl dimethylmalonate hydrochloride [VIII, $R^4$=OH, $Q^1$=$NH_2$, A=$(CH_3)_2C$]

To a solution of 5.32 g (0.010 mole) sodium 6-[2-(2-amino-2-[p-hydroxyphenyl]acetamido)]penicillanoyloxymethyl dimethylmalonate in 20 ml water is added 100 ml methylene chloride and 3.2 g (0.010 mole) tetrabutylammonium hydrogen sulfate. The mixture is adjusted to pH 7.5 with solid sodium bicarbonate, the organic layer is separated, the aqueous layer extracted with methylene chloride, the combined organic layers dried (Na$_2$SO$_4$) and evaporated in vacuo. The residue is added to 20 ml methyl acetoacetate, the mixture is heated at 65° C. for ten minutes, allowed to cool and the enamine derivative collected by filtration, washed with ethyl ether and air dried. The recovered enamine derivative is taken up in 35 mol chloroiodomethane and stirred overnight at room temperature. The mixture is then concentrated and the residue purified by chromatography on silica gel to provide the corresponding chloromethyl ester.

The chloromethyl ester 5.8 g, is dissolved in acetone (50 ml), 1.5 g sodium iodide is added and the solution is stirred overnight. Evaporation of solvent, partitioning the residue between water and ethyl acetate and evaporation of solvent affords iodomethyl ester of suitable purity for use in the next step.

To a mixture of 6.7 g of the iodomethyl ester obtained above and 4.5 g (0.010 mole) tetrabutylammonium 1,1-dioxopenicillanate is added 50 ml dimethylformamide and the mixture is stirred for 30 minutes at room temperature. The solution is diluted with 300 ml ethyl acetate, washed with brine, water, brine again and dried over anhydrous sodium sulfate. Evaporation of solvent in vacuo affords a residue which is taken up in 100 ml acetone, 100 ml 0.1N hydrochloric acid is added and the mixture stirred for 25 minutes. The acetone is evaporated in vacuo and the aqueous residue extracted with ethyl acetate/ethyl ether, then clarified by filtration. The filtrate is freeze dried to afford a crude solid product which is purified by chromatography on Sephadex LH-20*.
*A registered trademark of Pharmacia Fine Chemicals, Piscataway, N.J.

In like manner sodium 6-[D-(2-amino-2-phenylacetamido)]penicillanoyloxymethyl glutarate is converted to enamine protected iodomethyl ester and this reacted with tetrabutylammonium 1,1-dioxopenicillanate to provide 6-[D-(2-amino-2-phenylacetamido)]-penicillanoyloxymethyl 1,1-dioxopenicillanoyloxymethyl glutarate hydrochloride [VIII, R$^4$=H, Q$^1$=NH$_2$, A=(CH$_2$)$_3$].

EXAMPLE 46

Benzyl 6-(D-2-azido-2-phenylacetamido)-penicillanoyloxymethyl adipate

To 11.8 g (0.05 mole) benzyl adipate half ester in 250 ml chloroform and 40 ml water is added 40% aqueous tetrabutylammonium hydroxide with vigorous stirring until the mixture is pH 8.5. The organic phase is separated, the aqueous layer extracted with chloroform and the combined extracts dried over anhydrous sodium sulfate. Evaporation of solvent gives tetrabutylammonium benzyl adipate as an oil. The oil is mixed with toluene (250 ml) and 2.56 g (0.05 mole) iodomethyl 6-[D-(2-azido-2-phenylacetamido)]-penicillanate is added. The mixture is stirred for one hour, diluted to 500 ml with ethyl acetate and the precipitated tetrabutylammonium iodide removed by filtration, washing with ethyl acetate. The filtrate and washings are washed with sodium bicarbonate solution, water, brine and dried (Na$_2$SO$_4$). Evaporation of solvent affords the title compound which is purified by silica gel chromatography.

EXAMPLE 47

6-[D-(2-Amino-2-phenylacetamido)]-penicillanoyloxymethyl adipate half ester

To 2.0 g of benzyl 6-[D-(2-azido-2-phenylacetamido)]penicillanoyloxymethyl adipate, obtained in the preceding Example, dissolved in 50 ml each of dichloromethane and isopropanol, is added 1.0 g of 10% palladium-on-carbon and the mixture hydrogenated at 3–4 kg/cm$^2$ with agitation for two hours. The catalyst is removed by filtration, the filtrate and washings concentrated in vacuo to afford the desired product which is purified by chromatography or by recrystallization.

EXAMPLE 48

Potassium 6-[D-(2-[1-methyl-2-methoxycarbonylvinylamino]-2-phenylacetamido)penicillanoyloxymethyl adipate To a suspension of 7.6 g (0.055 mole) potassium carbonate in 75 ml dimethylformamide is added 10.8 ml (0.10 mole) methyl acetoacetate and 24.6 g (0.05 mole) 6-[D-(2-amino-2-phenylacetamido)]penicillanoyloxymethyl adipate half ester and the mixture is stirred at room temperature for two hours, then at 0°–5° C. for 4 hours. Ethyl acetate (250 ml) is added, the mixture stirred for 5 minutes and allowed to stand at 0°–5° C. for one hour. The solvent phase is decanted. The residue is washed twice with ether by decantation, dissolved in 150 ml acetone and filtered through a filter aid. The filtrate is diluted with 150 ml isopropanol and set aside at 0°–5° C. The precipitated product is recovered by filtration, washed with ethyl ether and dried in air.

EXAMPLE 49

6-[D-(2-Amino-2-phenylacetamido)]-penicillanoyloxymethyl 1,1-dioxopenicillanoyloxymethyl adipate [VIII, R$^4$=H, Q$^1$=NH$_2$, A=(CH$_2$)$_4$]

To 35 ml dimethylformamide is added 1.86 g (0.005 mole) iodomethyl 1,1-dioxopenicillanate and 3.14 g (0.005 mole) potassium 6-[D-(2-[1-methyl-2-methoxycarbonylvinylamino]-2-phenylacetamido)penicillanoyloxymethyl adipate and the mixture is stirred at room temperature for two hours. Ethyl acetate (150 ml) is added, the mixture washed with brine, water, brine again, dried (Na$_2$SO$_4$) and concentrated in vacuo. The residue is taken up in acetone (100 ml), 50 ml of 0.1N hydrochloric acid added, and the mixture is stirred for 20 minutes. The acetone is evaporated in vacuo, the aqueous residue is washed with ethyl acetate and ethyl ether, cooled, neutralized with sodium bicarbonate solution and quickly extracted with methylene chloride. The combined extracts are dried (MgSO$_4$) and the solvent evaporated in vacuo to afford the title compound as the free base.

EXAMPLE 50

The procedure of Example 46 is repeated but using the appropriate benzyl half ester in place of benzyl adipate half ester and the appropriate halomethyl 6-[2-(Q$^1$-substituted)-2-(R$^4$-phenylacetamido)]penicillanate to provide the compounds of the formula below:

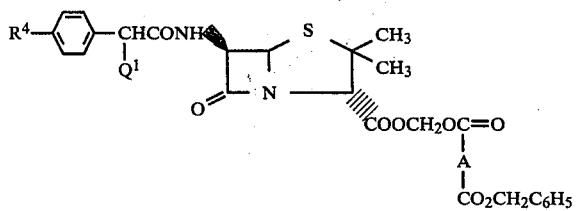

where $Q^1$ is azido, benzyloxycarbonylamino or 4-nitrobenzyloxycarbonylamino and A and $R^4$ are as defined previously.

In the starting halomethyl ester "halo" may be iodo, bromo, chloro, methylsulfonyloxy or p-toluenesulfonyloxy.

EXAMPLE 51

By repeating each of the procedures of Examples 47, 48 and 49 in turn with the products provided in the previous Example, the following compounds are obtained in like manner:

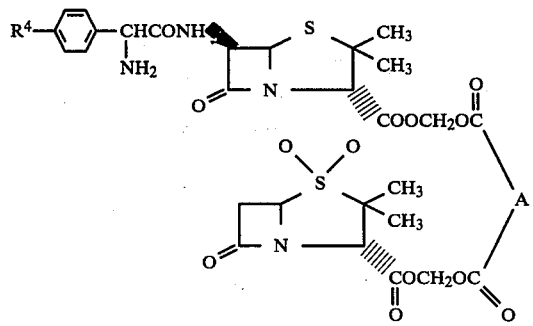

where $R^4$ and A are as defined in the preceding Example.

EXAMPLE 52

6-[D-(2-Amino-2-phenylacetamido)]-penicillanoyloxymethyl 1,1-dioxopenicillanoyloxymethyl dimethylmalonate p-toluenesulfonate

A

6-[D-(2-[1-methyl-2-methoxycarbonylvinylamino]-2-phenylacetamido)]penicillanoyloxymethyl 1,1-dioxopenicillanoyloxymethyl dimethylmalonate To 4.0 g (0.01 mole) sodium, 1,1-dioxopenicillanoyloxymethyl dimethylmalonate and 6.0 g (0.01 mole) iodomethyl 6-[D-(2-[1-methyl-2-methoxycarbonylvinylamino]-2-phenylacetamido)]penicillanate is added 40 ml dimethylformamide and the mixture is stirred at room temperature for 30 minutes. The mixture is poured into 300 ml ethyl acetate, washed with water (4×100 ml), brine (1×100 ml), dried (Na$_2$SO$_4$) and concentrated in vacuo to afford 9.3 g of foam. The foam is purified by chromatography on silica gel (300 g), eluting with 60:40 ethyl acetate/hexane taking 25 ml fractions. Fractions 39-65 are combined and evaporated in vacuo to yield 4.3 g (51%) tan foam. $^1$H-NMR (CDCl$_3$) ppm (delta): 1.43 (s, 3H), 1.46 (s, 9H), 1.53 (s, 3H), 1.6 (s, 3H), 1.9 (s, 3H), 3.42 (d, 2H), 3.63 (s, 3H), 4.4 (s, 1H), 4.42 (s, 1H), 4.53–4.57 (m, 2H), 5.06 (d, 1H), 5.35–5.93 (m, 6H), 6.73 (d, 1H), 7.33 (s, 5H), 9.4 (d, 1H).

B

To 30 ml ethyl acetate is added 0.836 g (1 mmole) of the enamine obtained in Part A, above, and the mixture stirred to obtain a solution. A solution of 0.19 g (1 mmole) p-toluenesulfonic acid hydrate in 5 ml ethyl acetate is added and the mixture stirred for 15 minutes, and the solvent evaporated to yield a hard gum. The gum is triturated with 150 ml ethyl ether, stirred overnight, filtered, washed with ethyl ether and air dryed to give 0.84 g (92%) of tosylate salt. $^1$H-NMR DMSO.D$_6$) ppm (delta): 1.4 (s, 12H), 1.5 (s, 6H, 2.3 (s, 3H), 3.1–3.9 (m, 2H), 4.36 (s, 1H), 4.5 (s, 1H), 5.0–5.26 (m, 2H), 5.33–6.0 (m, 6H), 7.06 (d, 2H), 7.3–7.63 (m, 7H).

EXAMPLE 53

6-beta-Bromopenicillanoyloxymethyl 6-[D-(2-amino-2-phenyl)acetamido]-penicillanoyloxymethyl Glutarate

A

Iodomethyl 6-beta-bromopenicillanate

To a stirred solution of 0.96 g (3 mmole) potassium 6-beta-bromopenicillanate and 1.80 g (18 mmole) potassium bicarbonate in 9 ml each of water and ethyl acetate is added 0.10 g (0.3 mmole) tetrabutylammonium hydrogen sulfate, followed by 0.45 g (4.5 mmole) chloromethyl chlorosulfonate and the mixture stirred for 1.5 hours. The organic phase is separated, the aqueous phase extracted with ethyl acetate and the combined organic layers are washed with water, dried and concentrated in vacuo to about 5 ml. The crude product is purified by chromatography on silica gel (petroleum ether/ethyl acetate 9:1) to afford chloromethyl 6-beta-bromopenicillanate as a nearly colorless oil.

To a solution of 0.82 g (2.5 mmole) of this chloromethyl ester in acetone (5 ml) is added 0.75 g (5 mmole) sodium iodide and the mixture stirred for 24 hours. The precipitated salt is removed by filtration, the filtrate evaporated in vacuo, and the oily residue taken up in ethyl acetate. The solution is washed with water, dried (MgSO$_4$), concentrated to a small volume and purified in the same manner as the chloromethyl ester to provide the desired iodomethyl ester as a yellow oil. $^1$H-NMR (CDCl$_3$) ppm (delta): 1.55 (s, 3H), 1.69 (s, 3H), 4.5 (s, 1H), 5.34 and 5.57 (2d, J=4Hz, 2H), 5.97 (ABq, J=5Hz, 2H).

B 6-beta-Bromopenicillanoyloxymethyl 6-[D-(2-(2-methyl-2-methoxycarbonylvinylamino[-2-phenylacetamido)] penicillanoyloxymethyl glutarate To a stirred solution of tetrabutylammonium 6-[D-(2-methyl-2-methoxycarbonylvinylamino]-2-phenylacetamido)]-penicillanoyloxymethyl glutarate (832 mg, 1 mmole) in 3 ml each of ethyl acetate and dichloromethane is added a solution of 430 mg (1 mmole) iodomethyl 6-beta-bromopenicillanate in 5 ml ethyl acetate. After stirring for a few minutes, the resulting slurry is concentrated to remove dichloromethane, filtered to remove precipitated salt and the filtrate is washed with water (5 ml). To the organic phase is added fresh water (10 ml) and the pH adjusted to 3 with 1N hydrochloric acid. The aqueous phase is separated and freeze dried to afford the title compound as the hydrochloride salt.

C

In similar manner the compounds of the formula below are obtained from the appropriate starting materials

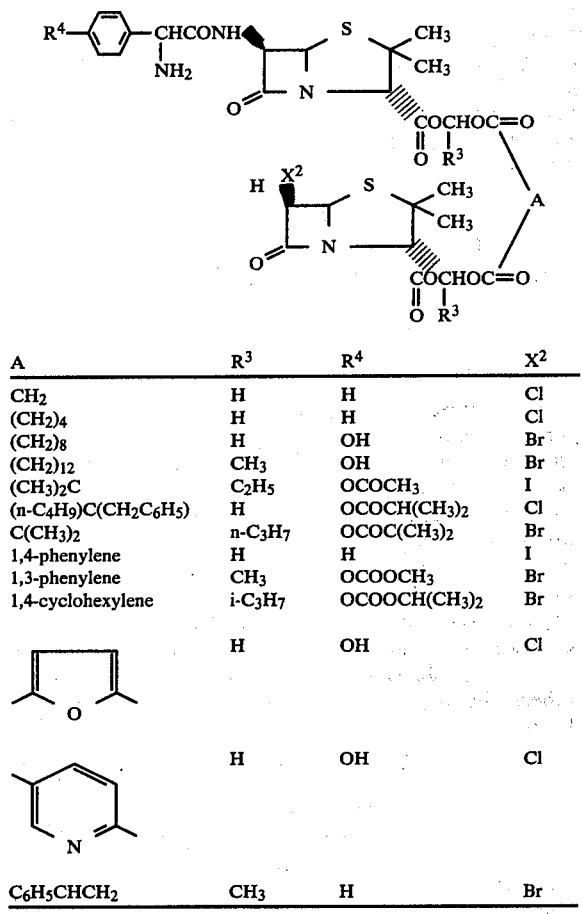

| A | $R^3$ | $R^4$ | $X^2$ |
|---|---|---|---|
| $CH_2$ | H | H | Cl |
| $(CH_2)_4$ | H | H | Cl |
| $(CH_2)_8$ | H | OH | Br |
| $(CH_2)_{12}$ | $CH_3$ | OH | Br |
| $(CH_3)_2C$ | $C_2H_5$ | $OCOCH_3$ | I |
| $(n-C_4H_9)C(CH_2C_6H_5)$ | H | $OCOCH(CH_3)_2$ | Cl |
| $C(CH_3)_2$ | $n-C_3H_7$ | $OCOC(CH_3)_2$ | Br |
| 1,4-phenylene | H | H | I |
| 1,3-phenylene | $CH_3$ | $OCOOCH_3$ | Br |
| 1,4-cyclohexylene | $i-C_3H_7$ | $OCOOCH(CH_3)_2$ | Br |
| (furan) | H | OH | Cl |
| (pyridine) | H | OH | Cl |
| $C_6H_5CHCH_2$ | $CH_3$ | H | Br |

EXAMPLE 54

Employing the appropriate starting compound of formula BCOOH or its sodium or potassium salt in the procedures of Preparations C and D or Part A of the preceding Example, the corresponding compounds of formula $BCOOCH(R^3)Cl$ or $BCOOCH(R^3)I$ are obtained in like manner, where $R^3$ is H, $CH_3$, $C_2H_5$ or $C_3H_7$ and B is as defined below

| B | BCOOH or salt obtained by Procedure of |
|---|---|
| 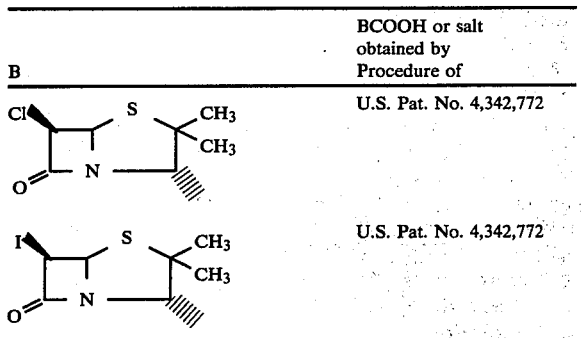 | U.S. Pat. No. 4,342,772 |
| | U.S. Pat. No. 4,342,772 |

-continued

| B | BCOOH or salt obtained by Procedure of |
|---|---|
| 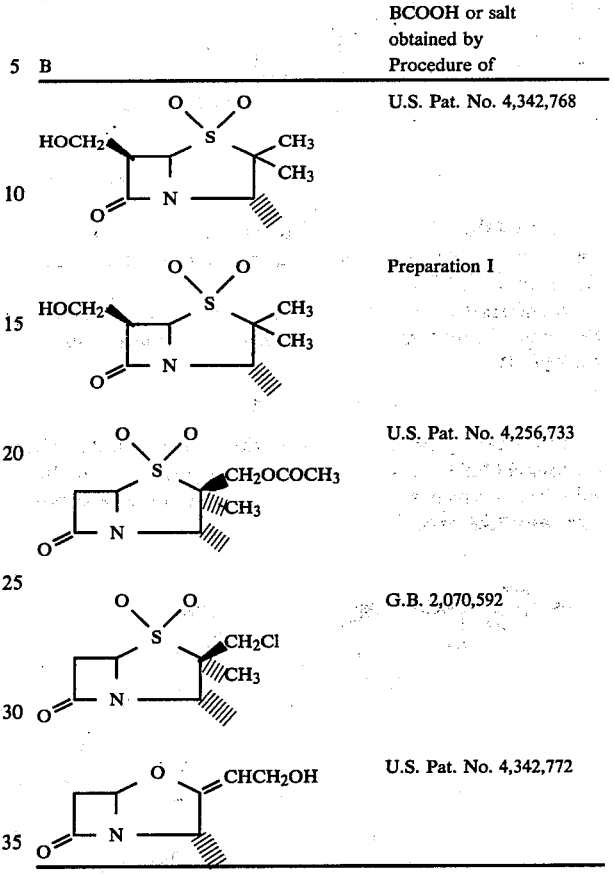 | U.S. Pat. No. 4,342,768 |
| | Preparation I |
| | U.S. Pat. No. 4,256,733 |
| | G.B. 2,070,592 |
| | U.S. Pat. No. 4,342,772 |

EXAMPLE 55

Employing one of the halomethyl esters provided in the preceding Example and an appropriate monobenzyl ester of formula $HOOC-A-CO_2CH_2C_6H_5$ as reactants in the procedure of Example 3, the corresponding compound of formula $$BCOOCH(R^3)OC=O$$
$$\diagdown A-COOR^1$$

is obtained wherein $R^1$ is benzyl, B and $R^3$ are as defined in Example 54 and A is as defined in Examples 1–3 and 9. Hydrogenolysis by the method of Example 4 provides the corresponding carboxylic acid or salt where $R^1$ is H or Na.

Alternatively, a cationic salt, e.g., the sodium salt of the compound BCOOH, is reacted with the monoiodo ester of the acid, $A(COOH)_2$, where A and B are as defined above, to directly provide the compounds of the above formula where $R^1$ is H. The monoiodo esters of the dicarboxylic acids, $A(COOH)_2$, are obtained, for example, by hydrogenolysis of the corresponding benzyl chloromethyl diester over Pd/C catalyst and subsequent reaction of the resulting monochloromethyl ester with sodium iodide in acetone.

EXAMPLE 56

1,1-Dioxo-6-beta-hydroxymethylpenicillanoyloxymethyl 6-[D-(2-amino-2-phenylacetamido)]penicillanoyloxymethyl trans-1,4-cyclohexanedicarboxylate Hydrochloride

A

Reaction of equimolar amounts of sodium 1,1-dioxo-6-beta-hydroxymethylpenicillanoyloxymethyl trans-1,4-cyclohexanedicarboxylate and iodomethyl 6-[D-(2-[1-methyl-2-methoxycarbonylvinylamino]-2-phenylacetamido)]penicillanate in dimethylformamide by the procedure of Example 20 affords the corresponding coupled enamine: 1,1-dioxo-6-beta-hydroxymethyl-penicillanoyloxymethyl 6-[D-(2-[1-methyl-2-methoxycarbonylvinylamino]-2-phenylacetamido)]penicillanoyloxymethyl trans-1,4-cyclohexanedicarboxylate. Hydrolysis of the amino protecting group by the procedure of Example 21 affords the title hydrochloride salt.

In like manner the following compounds are prepared and isolated as the hydrochloride salt of the formula below.

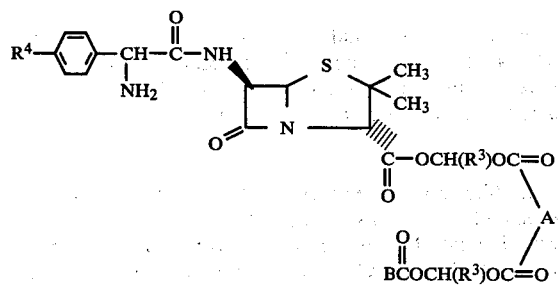

where $R^3$, $R^4$, A and B are as defined below.

| A | BC=O | $R^3$ | $R^4$ |
|---|---|---|---|
| 1,2-phenylene | 6-beta-chloro-penicillanoyl | H | H |
| 1,3-phenylene | 6-beta-bromo-penicillanoyl | H | OH |
| 1,4-naphthalene | 6-beta-iodo-penicillanoyl | CH₃ | OH |
| (CH₂)₂ | 1,1-dioxo-6-beta-hydroxymethyl-penicillanoyl | C₂H₅ | OCOCH₂CH₃ |
| (CH₃)₂C | 1,1-dioxo-6-alpha-hydroxymethyl-penicillanoyl | n-C₃H₇ | OCOCH(CH₃)₂ |
| (CH₂)₄ | 1,1-dioxo-2-beta-acetoxymethyl-2-alpha-methylpenam-3-alpha-carbonyl | i-C₃H₇ | OH |
| (CH₂)₈ | 1,1-dioxo-2-beta-chloromethyl-2-alpha-methylpenam-3-alpha-carbonyl | H | H |
| (CH₂)₁₂ | clavulanoyl | H | OH |
| n-C₄H₉(CH₃)C | clavulanoyl | CH₃ | H |
|  | clavulanoyl | C₂H₅ | OCOOCH₃ |
| 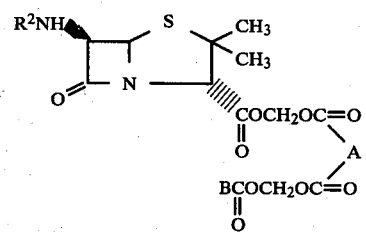 | 1,1-dioxo-2-beta-chloromethyl-2-alpha-methylpenam-3-alpha-carbonyl | H | H |
| 1,4-cycloheptyl | 6-beta-bromo-penicillanoyl | CH₃ | OH |
| 1,3-cyclopentyl | 6-beta-chloro-penicillanoyl | H | OH |
| 1,4-cyclohexyl | 1,1-dioxo-6-beta-hydroxymethyl-pencillanoyl | H. | OCOCH₃ |

EXAMPLE 57

Iodomethyl clavulanate, provided in Example 54, is reacted with an equimolar amount of sodium 6-(2-phenoxyacetamido)penicillanoyloxymethyl glutarate, provided in Example 17 by the method of Example 28, Part A, to provide the coupled product of the formula where A is (CH₂)₃, B is clavulanoyl and $R^2$ is C₆H₅OCH₂CO. In like manner compounds of the above formula are obtained from the appropriate starting materials where A, B and $R^2$ are shown below.

| A | BC=O | $R^2$ |
|---|---|---|
| Trans-1,4-cyclohexylene | 6-beta-chloro penicillanoyl | 2,6-dimethoxy-benzoyl |
| 1,4-phenylene | 6-beta-bromo penicillanoyl | phenoxyacetyl |
| (C₂H₅)₂C | 6-beta-iodo-penicillanoyl | 2-azido-2-phenylacetyl |
| (CH₃)₂C | 1,1-dioxo-6-beta hydroxymethyl-penicillanoyl | H |
| (CH₃)CHCH₂ | 1,1-dioxo-2-beta acetoxymethyl-2-alpha-methylpenam-3-alpha-carbonyl | phenoxyacetyl |
| CH₂C(COOH)CH₂ | 1,1-dioxo-2-beta-chloromethyl-2-alpha-methylpenam-3-alpha-carbonyl | 2,6-dimethoxy benzoyl |
| (CH₂)₄ | clavulanoyl | 2,6-dimethoxy-benzoyl |
| (CH₂)₃ | clavulanoyl | 2-carboxy-2-phenylcarbonyl |

EXAMPLE 58

Iodomethyl 6-alpha-(benzyloxycarbonylaminomethyl)-penicillanic Acid 1,1-Dioxide

A 6-alpha-(Benzyloxycarbonylaminomethyl)penicillanic acid 1,1-dioxide 6-alpha-(Aminomethyl)penicillanic acid 1,1-dioxide (2.62 g, 0.01 mole) is added to 20 ml water and 80 ml acetone at 15°–20° C., and the pH adjusted to 8 with dilute NaOH. A solution of benzyl chloroformate (1.88 g, 0.011 mole) in 20 ml acetone is added dropwise at 15°–20° C. while simultaneously maintaining the apparent pH of the reaction between 7 and 8 by the periodic addition of dilute NaOH. The reaction mixture is allowed to stir for 30 minutes, and is then concentrated in vacuo to remove most of the acetone. The aqueous solution is extracted twice with ethyl acetate and the extracts discarded. Fresh ethyl acetate (100 ml) is added to the water layer and the pH adjusted to 2 with dilute hydrochloric acid, with stirring. The organic layer is removed, washed with brine, dried over $Na_2SO_4$, and concentrated in vacuo to provide the title product.

B

Chloromethyl 6-alpha-(benzyloxycarbonylaminomethyl)-penicillanate 1,1-dioxide

The product of Part A, above, (1 g) is combined with 10 ml of methylene chloride and 2 ml of water and the pH adjusted to 8.0 with 40% tetrabutylammonium hydroxide over a period of 15 minutes. The methylene chloride layer is separated and the aqueous layer extracted with three 2 ml portions of fresh methylene chloride. The methylene chloride layers are combined, dried over $Na_2SO_4$, and concentrated in vacuo to yield tetrabutylammonium salt. The salt is combined with 10 ml of chloroiodomethane, the mixture stirred for 16 hours, and concentrated to dryness in vacuo to yield the desired ester.

C

The chloromethyl ester obtained in above (0.24 g) is combined with 3 ml of acetone and sodium iodide (0.58 g) and the mixture stirred for 16 hours. The reaction mixture is concentrated in vacuo and the residue distributed between 7.5 ml of ethyl acetate and 5.0 ml of water. The ethyl acetate is separated, washed in sequence with two 25 ml portions of water and one 25 ml portion of brine, dried over $Na_2SO_4$ and concentrated in vacuo to provide present title product.

By the above procedure the analogous compounds of the formula below are obtained in like manner.

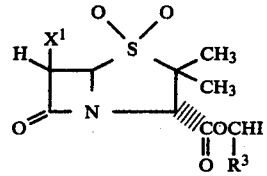

| $X^1$ | $R^3$ |
|---|---|
| beta-$CH_2NHCO_2CH_2C_6H_5$ | H |
| beta-$CH(CH_3)NHCO_2CH_2C_6H_5$ | $CH_3$ |
| alpha-$CH(CH_3)NHCO_2CH_2C_6H_5$ | $C_2H_5$ |
| alpha-$CH_2NHCO_2CH_2C_6H_5$ | n-$C_3H_7$ |
| beta-$CH_2NHCO_2CH_2C_6H_5$ | $CH_3$ |

EXAMPLE 59

1,1-Dioxo-6-alpha-(aminomethyl)penicillanoyloxymethyl Adipic Acid, Sodium Salt

A

Employing benzyl adipate half ester and iodomethyl 6-alpha-(benzyloxycarbonylaminomethyl)penicillanate 1,1-dioxide as reactants in the procedure of Example 3 affords benzyl 1,1-dioxo-6-alpha-(benzyloxycarbonylaminomethyl)penicillanoyloxymethyl adipate.

B

Hydrogenolysis and reaction of the resulting carboxylic acid with sodium-2-ethylhexanoate provides the title sodium salt. Use of potassium 2-ethylhexanoate affords the corresponding potassium salt.

C

In like manner employing the remaining iodoalkyl 6-benzyloxycarbonylaminomethyl (or benzyloxycarbonylaminoethyl)penicillanate 1,1-dioxides provided in Example 58, Part C, the corresponding salts of the formula below are obtained.

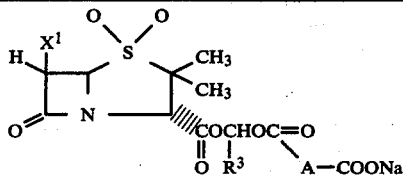

| A | $X^1$ | $R^3$ |
|---|---|---|
| $CH_2$ | beta-$CH_2NH_2$ | H |
| $(CH_2)_3$ | beta-$CH_2NH_2$ | H |
| trans-1,4-cyclohexylene | alpha-$CH_2NH_2$ | H |
| trans-1,4-cyclohexylene | beta-$CH_2NH_2$ | H |
| 1,4-phenylene | beta-$CH(CH_3)NH_2$ | $CH_3$ |
| 1,2-naphthalene | beta-$CH(CH_3)NH_2$ | $CH_3$ |
| 1,3-phenylene | beta-$CH(CH_3)NH_2$ | $CH_3$ |
| $(CH_2)_4$ | alpha-$CH(CH_3)NH_2$ | $C_2H_5$ |
| $(CH_2)_3$ | alpha-$CH(CH_3)NH_2$ | $C_2H_5$ |
| trans-1,4-cyclohexylene | alpha-$CH(CH_3)NH_2$ | $C_2H_5$ |
| $(CH_3)_2C$ | alpha-$CH_2NH_2$ | n-$C_3H_7$ |
| $(CH_2)_8$ | alpha-$CH_2NH_2$ | n-$C_3H_7$ |
| $(CH_2)_4$ | alpha-$CH_2NH_2$ | n-$C_3H_7$ |
| $(CH_2)_3$ | alpha-$CH_2NH_2$ | n-$C_3H_7$ |
| trans-1,4-cyclohexylene | alpha-$CH_2NH_2$ | n-$C_3H_7$ |
| trans-1,4-cyclohexylene | beta-$CH_2NH_2$ | $CH_3$ |
| $(CH_2)_3$ | beta-$CH_2NH_2$ | $CH_3$ |
| $(CH_2)_4$ | beta-$CH_2NH_2$ | $CH_3$ |
| $(CH_2)_8$ | beta-$CH_2NH_2$ | $CH_3$ |

61
-continued

![structure with H X¹, S(O)(O), CH3, CH3, COCHOC=O, O R³, A—COONa]

| A | X¹ | R³ |
|---|---|---|
| (CH2)12 | beta-CH2NH2 | CH3 |
| CH2 | beta-CH2NH2 | CH3 |
| (CH3)2C | beta-CH2NH2 | CH3 |
| trans-1,4-cyclohexylene | beta-CH2NH2 | CH3 |
| 1,4-phenylene | beta-CH2NH2 | CH3 |

EXAMPLE 60

6-[D-(2-Amino-2-phenylacetamido)]penicillanoyloxymethyl 1,1-dioxo-6-alpha-(aminomethyl)penicillanoyloxymethyl Adipate Hydrochloride Iodomethyl 6-alpha-(benzyloxycarbonylaminomethyl)-penicillanate 1,1-dioxide and tetrabutylammonium 6-[D-(2-benzyloxycarbonylamino-2-phenylacetamido)]-penicillanoyloxymethyl adipate are coupled by the procedure of Example 37 to afford the bis-benzyloxycarbonyl intermediate which is hydrogenated over palladium-on-carbon catalyst by the procedure of Example 40, Part B to obtain the free base which is taken up in ethyl acetate and acidified with ethanolic hydrogen chloride. Evaporation of solvent or addition of a non-solvent such as ethyl ether affords the title compound.

In like manner the compounds below are obtained by the above procedure.

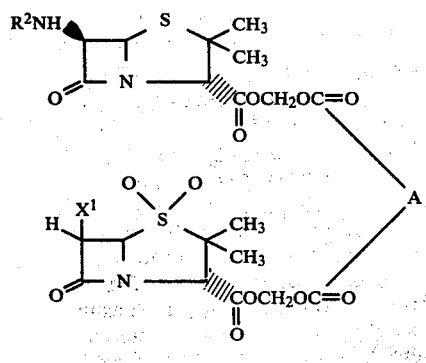

where A and X¹ are as defined in Example 59 and R² is as defined in Example 57 and is

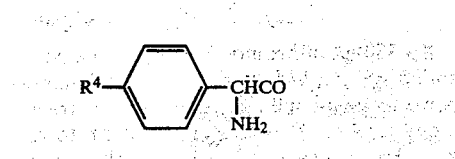

where R⁴ is as defined in Example 53.

EXAMPLE 61

Crystalline Acids of Formula V, $R^1=R^3=H$

A 1,1-Dioxopenicillanoyloxymethyl glutaric acid

Benzyl 1,1-dioxopenicillanoyloxymethyl glutarate is subjected to hydrogenolysis by the method of Example 4A. After evaporation of ethyl acetate from the filtrate, the residual oil is taken up in isopropanol, the mixture stirred at 22° C. for 60 minutes and held overnight at 50° C. The resulting solid is taken up in isopropanol, filtered and washed with cold isopropanol and hexane. The resulting crystals of 1,1-dioxopenicillanoyloxymethyl glutaric acid are vacuum dried at room temperature to obtain a 63% yield, m.p. 76°-78° C.

B 1,1-Dioxypenicillanoyloxymethyl diemethylmalonic acid

A solution of 10 g sodium 1,1-dioxopenicillanoyloxymethyl dimethylmalonate in 100 ml ethyl acetate is treated with hydrochloric acid (23 ml 1N in 50 ml water). The mixture is stirred, then allowed to stand. The organic layer is separated, dried, the solvent evaporated in vacuo and the residue chromatographed on 400 g silica gel, eluting with 1:1 ethyl acetate/acetone. The product fractions are combined and solvent evaporated. The resulting viscous oil is dissolved in ethyl ether, filtered to remove insolubles and the filtrate is evaporated to obtain an oil which crystallizes upon scratching, 7.2 g of white crystals, m.p. 121°-123° C.

Analysis: Calculated for $C_{14}H_{19}O_9NS$: C, 44.56; H, 5.07; N, 3.71. Found: C, 44.13; H, 5.19; N, 3.65.

PREPARATION A

Dibenzyl dimethylmalonate

To 75 ml water containing 4.0 g sodium hydroxide is added at 0° C., 17.0 g (0.05 mole) tetrabutylammonium hydrogen sulfate, the mixture is stirred 15 minutes, allowed to warm and 100 ml chloroform containing 14.2 g (0.05 mole) dibenzyl malonate and 6.6 ml (0.10 mole) methyl iodide is added. The mixture (initial pH>12) is stirred for 30 minutes at which time the mixture is pH ca. 8. Stirring is continued for ten minutes, the organic phase is separated. To the organic layer is added another charge of 4.0 g sodium hydroxide, 17.0 g tetrabutylammonium hydrogen sulfate in 75 ml water and 6.6 g methyl iodide. The resulting mixture is stirred at room temperature for 30 minutes, the chloroform layer is separated, dried (Na2SO4) and concentrated in vacuo. The resulting residual oil is triturated with 500 ml ethyl ether, the resulting solids are filtered, washed well with ether and the filtrate and washings evaporated to afford 15.0 g (96%) of product which is identified by ¹H-NMR spectrum.

PREPARATION B

Benzyl dimethylmalonate half ester

A solution of 3.12 g (48 mmole) of 85% potassium hydroxide in 75 ml benzyl alcohol is added to 15.0 g dibenzyl dimethylmalonate in 75 ml benzyl alcohol. The resulting solution is stirred for 60 hours, 1.5 liters of ethyl ether added and the resulting mixture extracted twice with 100 ml portions of water. The combined aqueous layers are washed with 100 ml ether. To the aqueous layer is added 100 ml ethyl ether and the mixture is acidified to pH 2.5 with 6N hydrochloric acid. The ether layer is separated and the aqueous phase extracted again with ether. The ether extracts are dried (Na$_2$SO$_4$) and solvent evaporated to afford the product as a colorless oil, 8.6 g (81%). R$_f$ 0.1 (TLC, 2:1 hexane/ethyl acetate). Structure verified by $^1$H-NMR.

PREPARATION C

Chloromethyl Penicillanate 1,1-Dioxide

A mixture of 4.66 g of penicillanic acid 1,1-dioxide, 50 ml of dichloromethane and 35 ml of water was treated with sufficient tetrabutylammonium hydroxide (40% in water) to give a pH of 6.0. The dichloromethane layer was separated and the aqueous phase extracted with fresh dichloromethane (2×50 ml). The organic layers were combined, dried over sodium sulfate and concentrated to give 10.1 g of the tetrabutylammonium salt of penicillanic acid 1,1-dioxide.

The above tetrabutylammonium penicillanate 1,1-dioxide was added to 50 ml of chloroiodomethane and the reaction mixture allowed to stir at ambient temperature overnight. The reaction mixture was concentrated to half volume in vacuo, and chromatographed on 200 g of silica gel using ethyl acetate/hexane as the eluant, 12 ml cuts being taken every 30 sec. Fractions 41–73 were combined and concentrated to dryness to give 3.2 g of the title compound.

The NMR spectrum (CDCl$_3$) showed absorptions at 1.5 (s, 3H), 1.66 (s, 3H), 3.42 (d, 2H), 4.38 (s, 1H), 4.6 (t, 1H) and 5.7 (dd, 2H) ppm.

PREPARATION D

Iodomethyl Penicillanate 1,1-Dioxide

To a solution of 7.9 g of chloromethyl penicillanate 1,1-dioxide in 100 ml of dry acetone maintained under a nitrogen atmosphere was added 21.0 g of sodium iodide, and the reaction mixture was allowed to stir overnight at room temperature. The reaction mixture was concentrated in vacuo, and the residue was dissolved in 150 ml ethyl acetate and 150 ml water. The organic layer was separated and the aqueous layer was extracted with fresh ethyl acetate. The organic extracts were combined, washed with water (1×500 ml) and brine (1×50 ml) and dried over sodium sulfate. Removal of the solvent gave 10.5 g of the title product, m.p. 100°–102° C.

The NMR spectrum (CDCl$_3$) showed absorptions at 1.55 (s, 3H), 1.68 (s, 3H), 3.5 (d, 2H), 4.4 (s, 1H), 4.65 (t, 1H) and 6.0 (dd, 2H) ppm.

PREPARATION E

Tetrabutylammonium 6-(2-Benzyloxycarbonylamino-2-[4-hydrophenyl]acetamido)penicillanate To a rapidly stirred mixture of 1.0 g of 6-(2-benzyloxycarbonylamino-2-[4-hydroxyphenyl]acetamide)penicillanic acid, 30 ml of dichloromethane and 20 ml of water was added 40% aqueous tetrabutylammonium hydroxide until a pH of 8.0 was obtained. Stirring was continued for 30 minutes at pH 8.0 and then the layers were separated. The aqueous layer was extracted with dichloromethane, and then the combined dichloromethane solutions were dried (Na$_2$SO$_4$) and evaporated in vacuo. This afforded 1.1 g of the title compound.

The NMR spectrum (in DMSO-d$_6$) showed absorptions at 0.70–1.80 (m, 34H), 2.90–3.50 (m, 8H), 3.93 (s, 1H), 5.10 (s, 2H), 5.23–5.50 (m, 3H), 6.76 (d, 2H), 7.20 (d, 2H), 7.40 (s, 5H), 7.76 (d, 1H) and 8.6 (d, 1H) ppm.

Tetrabutylammonium 6-(2-[4-nitrobenzyloxycarbonylamino]-2-[4-hydroxyphenyl]acetamido)penicillanate is obtained from 6-(2-[4-nitrobenzyloxycarbonylamino]-2-[4-hydroxyphenyl]acetamido)penicillanic acid and tetrabutylammonium hydroxide by the above method.

Tetrabutylammonium 6-[D-(2-benzyloxycarbonylamino-2-phenyl)acetamido]penicillanate and tetrabutylammonium-6-[D-2-(4-nitrobenzyloxycarbonylamino)-2-phenylacetamido]penicillanate are prepared in like manner.

PREPARATION F

Chloromethyl 6-[D-(2-azido-2-phenylacetamido)]penicillanate

A solution of 12.0 g (0.03 mole) 6-[D-(2-azido-2-phenylacetamido)]penicillanic acid sodium salt, 25 ml water is combined with 100 ml methylene chloride and 10.17 g (0.03 mole) tetrabutylammonium hydrogen sulfate. The mixture (pH 3.0) is adjusted to pH 7.5 with sodium bicarbonate, the organic layer is separated and the aqueous layer is extracted with 2×100 ml methylene chloride. The combined organic layers are dried (Na$_2$SO$_4$) and the solvent evaporated to yield a solid residue. The residue is triturated with ethyl acetate (300 ml), filtered, the cake washed with ethyl acetate followed by ethyl ether and dried under nitrogen to afford 16.5 g (89%) of tetrabutylammonium salt.

A mixture of 12.32 g (0.02 mole) of the above salt is combined with 70 ml chloroiodomethane and the mixture stirred overnight at ambient temperature. The reaction mixture is concentrated to dryness and the residue purified by chromatography on 600 g silica gel, eluting with 1:1 ethyl acetate/hexane by volume to afford 8.1 g (95%) of the desired chloromethyl ester as a pale yellow viscous oil.

Chloromethyl 6-[2-azido-2-(p-hydroxyphenyl)acetamido]penicillanate is obtained in like manner.

PREPARATION G

Iodomethyl 6-[D-(2-azido-2-phenylacetamido)]penicillanate

In a stoppered flask, 1.27 g (3 mmole) chloromethyl 6-[D-(2-azido-2-phenylacetamido)]penicillanate, 20 ml acetone and 2.25 g (15 mmole) sodium iodide are combined. The mixture is stirred overnight at room temperature, the resulting suspension is concentrated, the residue taken up in 100 ml ethyl acetate, washed with 3×30 ml water, 1×30 ml brine, dried (Na$_2$SO$_4$) and concentrated in vacuo to a pale yellow foam. The foam is purified by chromatography on 75 g silica gel, eluting with 1:1 by volume ethyl acetate/hexane, taking 20 ml fractions. Fractions 11–15 are combined and concentrated in vacuo to afford 1.18 g (76%) of the desired product as a pale yellow gum.

PREPARATION H

Benzyl chloromethyl adipate

To 350 ml of bromochloromethane cooled to 0° C. is added 67 g (0.14 mole) tetrabutylammonium salt of benzyl adipate half ester and the mixture is stirred overnight at 0° C. then allowed to warm to room temperature. The excess bromochloromethane is evaporated in vacuo, 400 ml ethyl ether is added to the residue and the mixture is stirred to form crystals of tetrabutylammonium bromide. The crystals are removed by filtration, washed with ether, stirred with ethyl acetate (300 ml) for one hour and refiltered and washed with ethyl acetate. The combined filtrates are evaporated in vacuo, the residue purified by chromatography on silica gel (1 kg), eluting with 2:1 hexane/ethyl acetate, to yield 19.1 g (48%) of the title compound. $^1$H-NMR (CDCl$_3$) ppm (delta): 1.58–1.9 (m, 4H), 2.2–2.62 (n, 4H), 5.13 (s, 2H), 5.68 (s, 2H), 7.38 (s, 5H).

The remaining benzyl chloromethyl esters of the formula below are prepared in like manner:

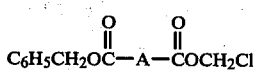

where A is as defined in the Examples.

PREPARATION I 6-alpha-Hydroxymethylpenicillanic Acid Sulfone

A.

Benzyl 6-bromo-6-hydroxymethylpenicillanate

A solution of 44.9 g of benzyl 6,6-dibromopenicillanate in 600 ml of dry tetrahydrofuran was cooled to −78° C. and 56.4 ml of t-butylmagnesium chloride was added dropwise with vigorous stirring under an inert atmosphere while maintaining the temperature at −60° C. After stirring 30 minutes at −78° C. the solution was treated with gaseous formaldehyde in a stream of nitrogen until five molar equivalents had been added. The reaction was quenched at −78° C. by the addition of 5.7 ml of acetic acid dropwise over a period of 25 minutes. The reaction solution was allowed to warm to room temperature and was concentrated in vacuo. To the residue was added 200 ml of water and 200 ml of ethyl acetate. The organic layer was separated and the water layer extracted again with ethyl acetate. The organic phases were combined, washed successively with water (200 ml), 5% aqueous sodium bicarbonate (200 ml) and brine (200 ml) and drive over magnesium sulfate. Removal of the solvent under reduced pressure provides 38.2 g of the desired product, epimeric at C-6.

B

Benzyl 6-bromo-6-hydroxymethylpenicillanate sulfone

To a solution of 500 mg of benzyl 6-bromo-6-hydroxymethylpenicillanate in 30 ml of methylene chloride, cooled in an ice bath at 0°–5° C., was added portionwise 633 mg of 85% m-chloroperbenzoic acid over a period of 20 minutes. The reaction mixture was allowed to warm to rooom temperature and allowed to stir for about 40 hours. The solvent was removed in vacuo and the residue treated with water and ethyl acetate. The pH of the mixture was adjusted to 7.4 with a saturated sodium bicarbonate solution, and the organic phase separated and treated with 30 ml of fresh water. The pH of the mixture was adjusted to 8.2 with saturated sodium bicarbonate and the ethyl acetate layer separated and washed with a saturated sodium bicarbonate solution and a brine solution. The ethyl acetate layer was separated, dried over magnesium sulfate and evaporated to an oil, 500 mg.

C 6-alpha-Hydroxymethylpenicillanic acid sulfone

A suspension of 500 mg of 5% palladium-on-charcoal and 500 mg of benzyl 6-bromo-6-hydroxymethylpenicillanate sulfone in 200 ml of 50% water-methanol was shaken in a hydrogen atmosphere at an initial pressure of 48 psi for 20 minutes. An additional 500 mg of fresh catalyst was added and the hydrogen pressure adjusted to 51 psi. After one hour of shaking the catalyst was filtered and the methanol removed in vacuo. The pH of the residual solution was adjusted to 8.0 and extracted with ethyl acetate. The aqueous layer was acidified to pH 2 with 6N hydrochloric acid and the product extracted with ethyl acetate. Removal of the solvent gave 100 mg of the desired product, which was crystallized from chloroformethyl acetate containing a drop of dimethyl sulfoxide, m.p. 211°–212° C.(dec.).

The NMR (100 MHz) spectrum (DMSO-D$_6$) showed absorption at 4.93 (d, 1H, J=2 Hz), 4.27 (s, 1H), 3.76 (m, 3H), 1.5 (s, 3H) and 1.4 (s, 3H) ppm.

PREPARATION J

Benzyl 6-alpha-bromo-6-beta-(benzyloxycarbonylaminomethyl)penicillanate and 6-beta-bromo-6-alpha-(benzyloxycarbonylaminomethyl)penicillanate To a solution of benzyl 6,6-dibromopenicillanate (108.73 g, 0.242 mole) in 600 ml dry tetrahydrofuran (THF), cooled to −78° C., was added an ether solution of methyl magnesium bromide (83.5 ml of 2.9M). After stirring for 15 minutes at −78° C., a solution of benzyloxycarboxamidomethyl acetate (27 g, 0.121 mole) in 200 ml dry THF was added over 10 minutes. After stirring for an hour at −78° C., the reaction was quenched by the addition of 14.52 ml of acetic acid. The mixture was warmed to room temperature and volatiles removed in vacuo at less than 35° C. Ethyl acetate was added to dissolve the residue, and the solution washed with water (100 ml), aqueous NaHCO$_3$ (100 ml), and 2×100 ml water, then dried over Na$_2$SO$_4$ and concentrated in vacuo to 113 g of oily product. The oil was column chromatographed on 1.2 kg silica gel, eluting first with 6 liters of 1:1 hexane:chloroform and then with chloroform. The first 6 liters of eluate was discarded. Further eluate was collected in 25 ml fractions. Fraction numbers 181–190 were concentrated. The pnmr spectrum of the residue in CDCl$_3$ revealed benzyl 6-alpha-bromo-6-beta-(benzyloxycarbonylaminomethyl)penicillanate: delta/TMS 1.37 (3H, s), 1.57 (3H, s), 3.86 (2H, d, J=6 Hz), 4.42 (1H, s), 5.06 (2H, s), 5.12 (1H, s), 7.25 (10H, s). Fraction numbers 201–249 were concentrated and the pnmr spectrum of this residue in CDCl$_3$ revealed benzyl 6-beta-bromo-6-alpha-(benzyloxycarbonylaminomethyl)penicillanate: delta/TMS 1.36 (3H, s), 1.60 (3H, s), 3.90 (2H, d, J=6.2 Hz), 4.47 (1H, s), 5.07 (2H, s), 5.14 (2H, s), 5.40 (1H, t, J=6.2), 5.47 (1H, s), 7.28 (5H, s), 7.30 (5H, s). The product from fraction numbers 171–240 was combined and concentrated to 22 of foam and used in the next experiment.

PREPARATION K

Benzyl 6-beta-(Benzyloxycarbonylaminomethyl)penicillanate

To a solution of title products (epimeric mixture) of Preparation J (22 g, 0.0413 mole) in 100 ml benzene was added tri-n-butyltin hydride (32.7 ml, 0.124 mole). The mixture was refluxed under $N_2$ for 2 hours, concentrated in vacuo to an oil and the oil triturated 4×100 ml hexane. The residual viscous oil was taken up in 70 ml of ether, from which title product crystallized over 1 hour [8.1 g in two crops] pnmr/CDCl$_3$/delta/TMS: 1.37 (3H, s), 1.57 (3H, s), 3.58 (3H, m), 4.34 (1H, s), 5.04 (2H, s), 5.12 (2H, s), 5.33 (1H, d, J=4 Hz), 7.32 (10H, s).

Benzyl 6-alpha-(benzyloxycarbonylaminomethyl)-pencillanate is recovered by concentration of mother liquors and chromatography.

PREPARATION L

Benzyl 6-beta-Benzyloxycarbonylaminomethyl)penicillanate 1-alpha-Oxide and Benzyl 6-beta-(Benzyloxycarbonylaminomethyl)-penicillanate 1-beta-Oxide To a solution of title product of the preceding Preparation (4.54 g, 0.01 mole) in 70 ml of ethyl acetate was added m-chloroperbenzoic acid (2.02 g, 0.01 mole) in 30 ml ethyl acetate. The mixture was stirred 30 minutes at room temperature, washed 1×50 ml saturated NaHCO$_3$ and 2×50 ml H$_2$O, dried over Na$_2$SO$_4$ and concentrated in vacuo to a viscous oil. The oil was dissolved in 50 ml of ether and 10 ml CHCl$_3$ and crystallization of title alpha-oxide induced by scratching (2.2 g, m.p. 123°–124° C., pnmr/CDCl$_3$/delta/TMS 1.22 (3H, s), 1.51 (3H, s), 3.7 (3H, m), 4.34 (1H, s), 4.63 (1H, d, J=4 Hz), 5.13 (2H, s), 5.22 (2H, s), 5.50 (1H, m), 7.34 (5H, s), 7.40 (5H, s)). Concentration of mother liquor to dryness in vacuo gave the title beta oxide as a viscous oil (2.5 g; pnmr/CDCl$_3$/delta/TMS 1.05 (3H, s), 1.60 (3H, s), 3.8 (3H, m) 4.63 (1H, s), 4.73 (1H, d, J=4 Hz), 5.13 (2H, s), 5.23 (2H, q), 5.70 (1H, m), 7.35 (5H, s), 7.39 (5H, s)).

PREPARATION M

Benzyl 6alpha-(Benzyloxycarbonylaminomethyl)penicillanate 1-beta-Oxide

To title beta-oxide of the preceding Preparation (2.3 g, 4.9 mmoles) in 100 ml CHCl$_3$ was added 1,5-diazabicyclo[4.3.0]non-5-ene (DBN, 0.607g, 4.9 mmoles). The mixture was stirred at room temperature for 15 minutes, diluted with 50 ml 1N HCl, and the layers separated. The organic layer was washed 2× 50 ml H$_2$O, dried over Na$_2$SO$_4$ and concentrated in vacuo to an oil (2.3 g). The oil was column chromatographed on 100 g silica gel, eluting with 4:1 CHCl$_3$:ethyl acetate in 20 ml fractions. Fractions 41–70 were combined and concentrated in vacuo to yield title product as a viscous oil (0.9 g; pnmr/CDCl$_3$/TMS 1.03 (3H, s), 1.60 (3H, s), 3.67 (3H, m), 4.46 (1H, s), 4.88 (1H, m) 5.08 (2H, s), 5.17 (2H, q), 5.39 (1H, m), 7.32 (5H, s), 7.37 (5H, s)).

PREPARATION N

Benzyl 6-beta-(Benzyloxycarbonylaminomethyl)penicillanate 1,1-Dioxide

To a solution of title product of Preparation K (8.0 g, 0.0176 mole) in 200 ml ethyl acetate cooled to 0°–5° C. was added m-chloroperbenzoic acid (10.68 g, 0.0528 mole). The mixture was warmed to room temperature, stirred for 6 hours, recooled to 0°–5° C. and diluted with 50 ml of saturated NaHSO$_3$. The organic layer was separated, washed 2×50 ml saturated NaHCO$_3$ and 2×50 ml H$_2$O, dried over Na$_2$SO$_4$ and concentrated in vacuo to a viscous oil (8.6 g). The oil was chromatographed on 250 g silica gel, eluting with 19:1 CHCl$_3$:ethyl acetate in 25 ml fractions. Fractions 44-150 were combined and concentrated in vacuo to yield title product as a white gummy foam (7.6 g; pnmr/CDCl$_3$/delta/TMS 1.25 (3H, s), 1.49 (3H, s) 3.98 (3H, m), 4.45 (1H, s), 4.59 (1H, d, J=4 Hz), 5.09 (2H, s), 5.19 (2H, q), 5.36 (1H, br), 7.36 (10H, s)).

PREPARATION O

Benzyl 6-alpha-(Benzyloxycarbonylaminomethyl)penicillanate 1,1-Dioxide

By the procedure of Preparation M, the title 1,1-dioxide of the preceding Preparation (3.3 g, 6.79 mmoles) was converted to present title product (3.1 g crude), and purified by column chromatography on 150 g silica gel, eluting with 1:9 ethyl acetate:CHCl$_3$ in 20 ml fractions. Fractions 26-37 were combined and concentrated in vacuo to yield purified title product, as a viscous oil which crystallized on standing (1.9 g; m.p. 112°–113° C.; pnmr/CDCl$_3$/delta/TMS 1.20 (3H, s), 1.49 (3H, s), 3.65 (3H, m), 4.32 (1H, s), 4.59 (1H, m), 5.07 (2H, s), 5.14 (2H, q), 5.30 (1H, br), 7.32 (10H, s)).

Present title product was also obtained by the further oxidation of the title product of Preparation M with excess m-chloroperbenzoic acid according to the method of Preparation N.

PREPARATION P

6-beta-(Aminomethyl)penicillanic Acid 1,1-Dioxide

Title product of Preparation N (1.9 g), THF (40 ml), H$_2$O (40 ml) and 10% Pd/C (1.9 g) were combined and hydrogenated at 50 psig for 1 hour. Catalyst was recovered by filtration and THF removed from the filtrate in vacuo. The aqueous layer was washed with 30 ml ethyl acetate, freeze dried to a white powder and a first crystalline crop (0.26 g) obtained by trituration of the powder with 5 ml water. A second crop (0.14 g) crystallized on addition of 10 ml of acetone to the mother liquor and a third crop (0.35 g) by evaporating the second mother liquor to 2 ml and adding 50 ml of acetone. Total yield of title product was 0.75 g (pnmr/250 MHz/D$_2$O/delta/DSS 1.47 (3H, s), 1.59 (3H, s), 3.74 (2H, m), 4.36 (1H, td, J=4, 5.5 Hz), 4.45 (1H, s), 5.17 (1H, d, J=4 Hz).

To obtain the potassium salt, title product (1.0 g) is dissolved in 30 ml of water and cooled in an ice water bath, one equivalent of 1N KOH is added dropwise to the well-stirred solution, and the resulting solution freeze dried.

PREPARATION Q

6alpha-(Aminomethyl)-penicillanic Acid 1,1-Dioxide

By the method of the preceding experiment, title product of Preparation O (1.7 g) was converted to present title product, except that crystalline product was obtained directly by concentration in vacuo following the ethyl acetate extraction (0.7 g; pnmr/250 MHz/D$_2$O/DSS 1.44 (3H, s), 1.59 (3H, s), 3.63 (2H, d, J=5.5 Hz) 4.07 (1H, td, J=2, 5.5 Hz) 4.31 (1H, s), 5.06 (1H, d, J=2)).

To obtain the hydrochloride salt, product (0.7 g) is dissolved in water (30 ml), an equivalent of dilute hydrochloride acid is added dropwise, and the resulting solution freeze dried.

To obtain the sodium salt, product (0.7 g) is dissolved in water (30 ml). At 0°-5° C., one equivalent of dilute sodium hydroxide is added with vigorous stirring and the solution freeze dried.

PREPARATION R

Employing 1-benzyloxycarboxamidoethyl acetate in place of benzyloxycarboxamidomethyl acetate in the procedure of Preparation J affords a mixture of isomers of benzyl 6-bromo-6-(1-benzyloxycarboxamidoethyl)-penicillanate which are separated as described in Preparation J. The purified products are then carried through the procedures of Preparations K, N, O, P and Q to afford the corresponding 6-alpha and 6-beta isomers of the compound below.

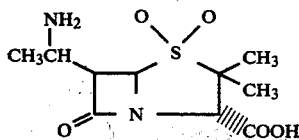

PREPARATION S

Potassium 2-beta-Chloromethyl-2-alpha-methyl-3-alpha-carboxylate 1,1-Dioxide

A 6-alpha-Bromopenicillanic acid 1-oxide 6-alpha-Bromopenicillanic acid N,N'-dibenzylethylenediamine (DBED) salt (Nature, 201, 1124 (1964); J. Org. Chem., 27, 2668 (1962)), 30 g (37.5 mmole) is dissolved in 330 ml methylene chloride and cooled to 0° C. Slowly, 13 ml (156 mmole) concentrated hydrochloric acid is added and the mixture stirred for 10 minutes at 0°-5° C. The precipitated DBED.HCl salt is removed by filtration, washing with 150 ml methylene chloride. As quickly as possible the combined filtrate and washings are washed with cold water (60 ml), stirring for five minutes before separating layers. The organic phase is concentrated in vacuo to 65-80 ml and the concentrate cooled with stirring to 5° C. Over a 30 minute period, 13 ml (86.9 mmole) of 40% peracetic acid is added at 15° to 18° C. (ice bath). The resulting mixture is stirred two hours at 0°-5° C., filtered and the cake washed with 5° C. water (10 ml), methylene chloride at 0°-5° C. and heptane. The washed solid is dried to obtain 16.26 g (73%) of bromosulfone.

B.

p-Nitrobenzyl 6-alpha-bromopenicillanate 1-oxide

To a solution of the product of Part A, 12 g (0.04 mole) in 100 ml acetone is added 7.5 g (0.041 mole) potassium 2-ethylhexanoate. The precipitated salt is collected by filtration, washed with cold acetone and air dried. The potassium salt (10 g) is dissolved in 75 ml N,N-dimethylacetamide and 7.8 g (0.04 mole) p-nitrobenzyl bromide is added and the mixture stirred at 23° C. for 24 hours, diluted with water (500 ml) and extracted with ethyl acetate. The organic extracts are washed with water, dried (MgSO4) and evaporated at reduced pressure to afford an oil that crystallizes upon standing. After slurring with ether and filtering, 9 g (70%) of the ester is obtained, m.p. 124°-125° C. (dec.).

C.

p-Nitrobenzyl-2-beta-chloromethyl-2-alpha-methyl 6-bromopenam-3-alpha-carboxylate A solution of 5 g (0.012 mole) of the above ester in 120 ml anhydrous dioxane is heated at reflux under nitrogen with 1.5 g (0.012 mole) quinoline and 1.6 g (0.012 mole) benzoyl chloride for 4 hours. The mixture is diluted with 600 ml water and extracted with ethyl acetate. The extracts are washed with 5% sodium bicarbonate solution, 5% phosphoric acid and finally with water. The organic layer is dried (MgSO4) and the solvent evaporated. The residual oil is washed with ethyl ether and cold toluene to obtain crystals, 3.5 g, m.p. 130°-135° C. (dec.).

D p-Nitrobenzyl 2-beta-chloromethyl-2-alpha-methyl-6-bromopenam-3-alpha-carboxylate 1-oxide To a solution of 1 g (0.0022 mole) of the product of Part C, in 50 ml methylene chloride is added 473 mg (0.0022 mole) m-chloroperbenzoic acid and the solution stirred at 23° C. for three hours. The solvent is evaporated to 20 ml, the concentrate diluted with heptane (50 ml) and the solvent decanted. The residue is slurried with ethyl ether to afford crystals, 250 mg (24%) m.p. 136°-137° C. (dec).

E.

To a solution of 7 g (0.015 mole) of the product of Part D in 150 ml ethyl acetate is added a suspension of 4 g of 30% palladium on diatomaceous earth and 2.8 g sodium bicarbonate in 150 ml water. The mixture is hydrogenated at 50 psi (3.52 kg/cm$^2$) for three hours. The mixture is filtered, the aqueous filtrate is separated and treated with 1.5 g potassium permanganate in 50 ml water. The mixture is stirred for one hour, 250 mg sodium bisulfite added and filtered. The filtrate is adjusted to pH 2 with concentrated hydrochloric acid and lyophilized to give an amorphous powder. The powder is extracted with ethyl acetate, the extracts concentrated to 20 ml and diluted with 100 ml heptane to precipitate solid 2-beta-chloromethyl-2-alpha-methylpenam-3-alpha-carboxylic acid 1,1-dioxide. The collected acid is dissolved in acetone, treated with solid potassium 2-ethylhexanoate and the precipitated crystalline title compound collected by filtration, 170 mg, m.p. 140° C. (dec.).

Analysis: Calculated for $C_8H_7ClKNO_5S \cdot 2H_2O$: C, 28.27; H, 3.24; N, 4.12. Found: C, 28.27; H, 3.69; N, 3.84.

$^1$H-NMR (D$_2$O) ppm (delta): 1.68 (s, 3H), 3.2–3.9 (m, J~2 Hz, J~4 Hz, J~6 Hz, 2H), 4.0–4.4 (m, 2H), 4.3 (s, 1H), 5.02 (dd, J~4 Hz, J~2 Hz, 1H).

We claim:
1. A compound of the formula

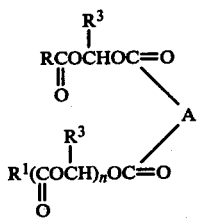

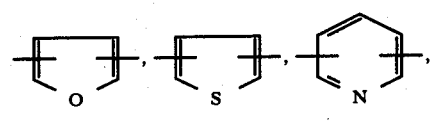

or a pharmaceutically acceptable cationic or acid addition salt thereof, wherein A is $(C_1-C_{12})$alkylene, $(C_1-C_{12})$alkylidene, $(C_3-C_7)$cycloalkylene, phenylene, naphthalene,

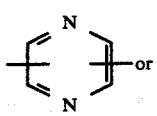

said alkylene or alkylidene substituted by phenyl or carboxy;
$R^3$ is H or $(C_1-C_3)$alkyl,
n is zero or 1,
R and $R^1$ are different and
R is P or B,
when n is zero, $R^1$ is H, $(C_1-C_4)$alkyl, benzyl, $CH(R^3)Cl$, $CH(R^3)I$ or tetrabutylammonium, and when n is 1, $R^1$ is P or B;
P is

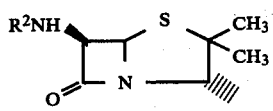

where $R^2$ is H,

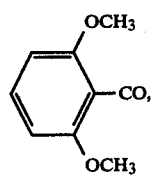

$C_6H_5OCH_2CO$ or

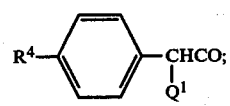

$Q^1$ is H, $NH_2$, $N_3$, benzyloxycarbonylamino, 4-nitrobenzyloxycarbonylamino or 1-methyl-2-methoxycarbonylvinylamino; $R^4$ is H, OH, $(C_2-C_7)$alkanoyloxy, $(C_2-C_7)$alkoxycarbonyloxy or $R^5C_6H_4COO$, and $R^5$ is H, $(C_1-C_4)$alkyl, $(C_1-C_4)$alkoxy, F, Cl, Br or CN; and B is

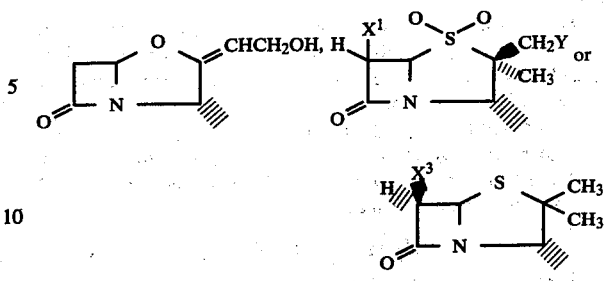

where, when Y is H, $X^1$ is H, $CH_2OH$ or $CH(R^8)NH_2$ where $R^8$ is H or $CH_3$;
when Y is Cl or $CH_3COO$, $X^1$ is H;
and $X^3$ is Cl, Br or I.

2. A compound according to claim 1 wherein when n is zero, $R^1$ is $(C_1-C_4)$alkyl, H or a sodium or potassium salt thereof, and when n is 1, R is B and $R^1$ is P where $R^2$ is H,

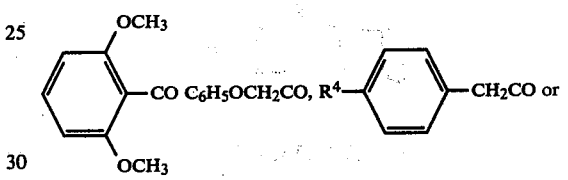

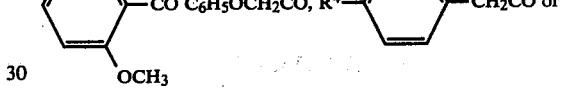

3. A compound according to claim 2 wherein when n is zero, $R^1$ is H or a sodium or potassium salt thereof and when n is 1, $R^2$ is $4-R^4C_6H_5CH(NH_2)CO$.

4. A compound according to claim 1 wherein A is $(C_1-C_{12})$alkylene, $(C_1-C_{12})$alkylidene, $(C_3-C_7)$cycloalkylene or phenylene.

5. A compound according to claim 4 wherein n is zero, R is P and $R^1$ is $(C_1-C_4)$alkyl, benzyl, $CH_2Cl$, $CH_2I$, H or a carboxylate salt forming cation selected from the group consisting of sodium, potassium or tetrabutylammonium.

6. A compound according to claim 5 wherein A is $(CH_2)_m$,

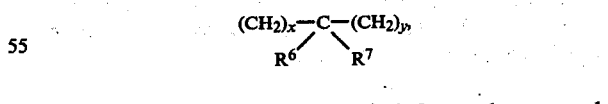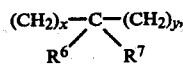

phenylene or cyclohexylene, m is 1–8, x and y are each zero or 1–6, $R^6$ is H or $(C_1-C_4)$alkyl and $R^7$ is $(C_1-C_4)$alkyl.

7. A compound according to claim 6 wherein $Q^1$ is $N_3$, $NH_2$ or 1-methyl-2-methoxycarbonylvinylamino, $R^1$ is benzyl, H or a carboxylate salt forming cation selected from the group consisting of sodium, potassium and tetrabutylammonium, and A is $CH_2$, $(CH_2)_2$, $(CH_2)_3$, $(CH_2)_4$, $(CH_2)_8$, phenylene or cyclohexylene.

8. A compound according to claim 7 wherein $R^2$ is

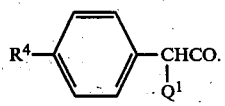

9. A compound according to claim 8 wherein $Q^1$ is $N_3$ and $R^4$ is H.

10. The compound according to claim 9 wherein A is $(CH_2)_4$ and $R^1$ is benzyl.

11. A compound according to claim 9 wherein $Q^1$ is $NH_2$ or 1-methyl-2-methyoxycarbonylvinylamino and $R^4$ is H or OH.

12. A compound according to claim 11 wherein A is $C(CH_3)_2$, $(CH_2)_3$, $(CH_2)_4$, 1,4-phenylene or trans-1,4-cyclohexylene.

13. A compound according to claim 12 wherein $R^4$ is H and A is $C(CH_3)_2$, $(CH_2)_3$, $(CH_2)_4$ or trans-1,4-cyclohexylene.

14. A compound according to claim 12 wherein $R^4$ is OH and A is $C(CH_3)_2$ or trans-1,4-cyclohexylene.

15. The compound according to claim 14 wherein $Q^1$ is $NH_2$, A is $C(CH_3)_2$ and $R^1$ is hydrogen or the hydrochloride salt thereof.

16. A compound according to claim 14 wherein $Q^1$ is $NH_2$, A is trans-1,4-cyclohexylene and $R^1$ is H, or the hydrochloride salt thereof.

17. The compound according to claim 13 wherein $Q^1$ is $NH_2$, A is $(CH_2)_4$ and $R^1$ is H or the hydrochloride salt thereof.

18. A compound according to claim 13 wherein $Q^1$ is $NH_2$, A is trans-1,4-cyclohexylene and $R^1$ is H or the hydrochloride salt thereof.

19. A compound according to claim 5 wherein $R^2$ is

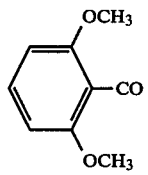

and A is $C(CH_3)_2$, $(CH_2)_3$ or trans-1,4-cyclohexylene.

20. A compound according to claim 5 wherein $R^2$ is $C_6H_5OCH_2CO$, A is $C(CH_3)_2$, $(CH_2)_3$, or trans-1,4-cyclohexylene.

21. A compound according to claim 4 wherein n is zero, R is B as defined above and $R^1$ is H, $(C_1-C_4)$alkyl, benzyl, $CH_2Cl$, $CH_2I$ or a carboxylate salt forming cation selected from the group consisting of sodium, potassium or tetrabutylammonium.

22. A compound according to claim 21 wherein B is

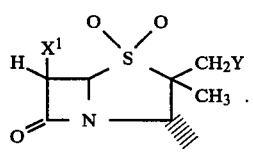

23. A compound according to claim 22 wherein Y and $X^1$ are each H.

24. A compound according to claim 23 wherein A is $(CH_2)_m$,

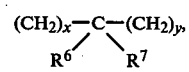

phenylene or cyclohexylene, m is 1–8, x and y are each zero or 1–6, $R^6$ is H or $(C_1-C_4)$alkyl and $R^7$ is $(C_1-C_4)$alkyl.

25. A compound according to claim 24 wherein A is $C(CH_3)_2$, $(CH_2)_3$, $(CH_2)_4$, $(CH_2)_8$, phenylene or trans-1,4-cyclohexylene.

26. A compound according to claim 25 wherein $R^1$ is benzyl, H or a carboxylate salt forming cation selected from the group consisting of sodium, potassium and tetrabutylammonium.

27. The compound according to claim 26 wherein A is $C(CH_3)_2$ and $R^1$ is H or sodium.

28. A compound according to claim 26 wherein A is $(CH_2)_3$ or $(CH_2)_4$ and $R^1$ is H or sodium.

29. A compound according to claim 26 wherein A is 1,4-phenylene and $R^1$ is H or sodium.

30. A compound according to claim 26 wherein A is trans-1,4-cyclohexylene and $R^1$ is H or sodium.

31. A compound according to claim 4 wherein n is 1, R is B and $R^1$ is P.

32. A compound according to claim 31 wherein P is

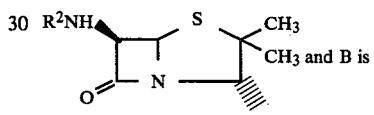

and B is

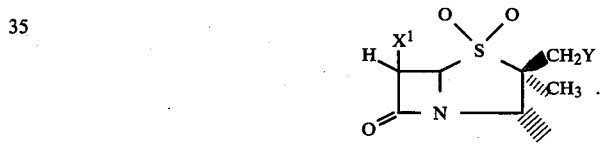

33. A compound according to claim 32 wherein $X^1$ and Y are each H.

34. A compound according to claim 33 wherein A is $(CH_2)_m$,

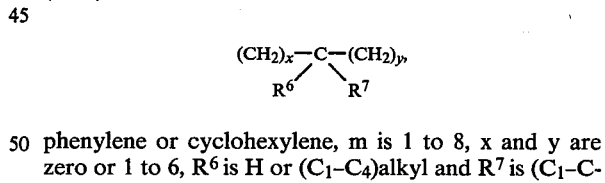

phenylene or cyclohexylene, m is 1 to 8, x and y are zero or 1 to 6, $R^6$ is H or $(C_1-C_4)$alkyl and $R^7$ is $(C_1-C_4)$alkyl.

35. A compound according to claim 34 wherein $R^2$ is H.

36. A compound according to claim 34 wherein $R^2$ is

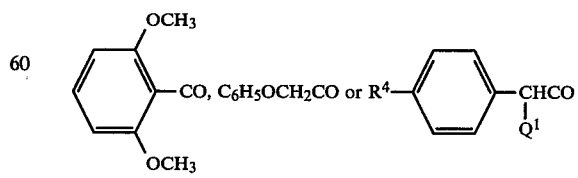

37. A compound according to claim 36 wherein A is $(CH_2)_2$, $(CH_2)_3$, $(CH_2)_4$, $(CH_2)_8$, $C(CH_3)_2$, 1,4-phenylene or trans-1,4-cyclohexylene and $R^2$ is

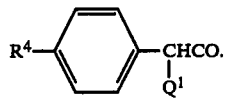

38. A compound according to claim 37 wherein $Q^1$ is $NH_2$.

39. A compound according to claim 38 wherein $R^4$ is H and A is $(CH_2)_2$, $(CH_2)_3$, $(CH_2)_4$, $C(CH_3)_2$ or trans-1,4-cyclohexylene.

40. The compound according to claim 39 wherein A is $(CH_2)_4$.

41. The compound according to claim 39 wherein A is trans-1,4-cyclohexylene.

42. A compound according to claim 38 wherein $R^4$ is OH and A is $(CH_2)_3$, $(CH_2)_4$, $C(CH_3)_2$ or trans-1,4-cyclohexylene.

43. A compound according to claim 38 wherein $R^4$ is $CH_3COO$ or $(CH_3)_3CCOO$ or $(CH_3)_2CHCH_2COO$ and A is $C(CH_3)_2$, $(CH_2)_3$, $(CH_2)_4$ or trans-1,4-cyclohexylene.

44. A method of treating a bacterial infection in a mammalian subject in need of such treatment, which comprises administering thereto an antibacterially effective amount of a compound according to claim 2.

45. A pharmaceutical composition suitable for treating a bacterial infection in a mammalian subject, which comprises an antibacterially effective amount of a compound according to claim 2 and a pharmaceutically acceptable carrier.

46. Crystalline tetrabutylammonium 6-[D-(2-[1-methyl-2-methoxycarbonylvinylamino]-2-phenylacetamido)]-penicillanate.

47. Crystalline tetrabutylammonium 6-[D-(2[1-methyl-2-methoxycarbonylvinylamino]-2-[4-hydroxyphenyl]-acetamido)]penicillanate.

48. The compound according to claim 30: 1,1-dioxopenicillanoyloxymethyl trans-1,4-cyclohexanecarboxylic acid.

49. The compound according to claim 28: 1,1-dioxopenicillanoyloxymethyl glutaric acid.

50. The compound according to claim 28: 1,1-dioxopenicillanoyloxymethyl adipic acid and hydrates thereof.

51. A crystalline monohydrate according to claim 50.

52. The compound according to claim 40; 6-[D-(2-amino-2-phenylacetamido)]-penicillanoyloxymethyl 1,1-dioxopenicillanoyloxymethyl adipate hydrochloride.

* * * * *